United States Patent
Rockson et al.

(10) Patent No.: US 10,500,178 B2
(45) Date of Patent: Dec. 10, 2019

(54) LTB4 INHIBITION TO PREVENT AND TREAT HUMAN LYMPHEDEMA

(71) Applicant: The Board of Trustees of the Leland Stanford Junior University, Stanford, CA (US)

(72) Inventors: Stanley G. Rockson, Stanford, CA (US); Mark R. Nicolls, Palo Alto, CA (US); Wen A. Tian, Redwood City, CA (US); Xinguo Jiang, Palo Alto, CA (US); Jeanna Kim, Daly City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/554,931

(22) PCT Filed: Mar. 11, 2016

(86) PCT No.: PCT/US2016/022132
§ 371 (c)(1),
(2) Date: Aug. 31, 2017

(87) PCT Pub. No.: WO2016/149126
PCT Pub. Date: Sep. 22, 2016

(65) Prior Publication Data
US 2018/0193296 A1 Jul. 12, 2018

Related U.S. Application Data

(60) Provisional application No. 62/133,086, filed on Mar. 13, 2015.

(51) Int. Cl.
*A61K 31/198* (2006.01)
*A61K 45/06* (2006.01)
*A61P 29/00* (2006.01)

(52) U.S. Cl.
CPC ............ *A61K 31/198* (2013.01); *A61K 45/06* (2013.01); *A61P 29/00* (2018.01)

(58) Field of Classification Search
CPC ........ A61K 31/198; A61K 45/06; A61P 29/00
USPC ....................................................... 514/563
See application file for complete search history.

(56) References Cited

U.S. PATENT DOCUMENTS

| | | |
|---|---|---|
| 8,965,708 B2 | 2/2015 | Tabibiazar et al. |
| 9,233,089 B2 | 1/2016 | Nicolls et al. |
| 2012/0076731 A1* | 3/2012 | Tabibiazar ............. A61B 5/411 424/9.2 |

OTHER PUBLICATIONS

Ionue, H et al, Br J. Pharmacology (1993), vol. 110(4), pp. 206-212. (Year: 1993).*

(Continued)

*Primary Examiner* — Craig D Ricci
*Assistant Examiner* — Janet L. Coppins
(74) *Attorney, Agent, or Firm* — Pamela J. Sherwood; Bozicevic, Field & Francis LLP

(57) ABSTRACT

Provided are therapeutic methods for treating a patient with lymphedema, or prophylactically treating an individual susceptible to lymphedema, by inhibiting synthesis activity of leukotriene $B_4$.

12 Claims, 19 Drawing Sheets
(8 of 19 Drawing Sheet(s) Filed in Color)
Specification includes a Sequence Listing.

(56) References Cited

OTHER PUBLICATIONS

Inoue et al., "Profile of capsaicin-induced mouse ear oedema as neurogenic inflammatory model: comparison with arachidonic acid-induced ear oedema", Br. J. Pharmacal. Dec. 1993, pp. 1614-1620, vol. 110, No. 4, John Wiley & Sons, Inc., Hoboken, NJ.
Ino et al.,"Monocyte activation by an oral immunomodulator (bestatin) in lymphoma patients following autologous bone marrow transplantation", Cancer Immunol Immunother. Dec. 1996, pp. 206-212, vol. 43, No. 4, Springer International Publishing AG, Cham, Switzerland.
Tatnall et al., "Non-Hodgkin's lymphoma of the skin associated with chronic limb lymphoedema", British Journal of Dermatology, Dec. 1985, pp. 751-756, vol. 113, No. 6, John Wiley & Sons, Inc., Hoboken, NJ.
Wang et al., "Current views on the function of the lymphatic vasculature in health and disease", Genes Dev.,Oct. 2010, pp. 2115-2126, vol. 24, No. 19, Cold Spring Harbor Laboratory Press, Cold Spring Harbor, NY.
Mortimer et al., "New developments in clinical aspects of lymphatic disease", The Journal of Clinical Investigation, Mar. 2014, pp. 915-921, vol. 124, No. 3, American Society for Clinical Investigation, Ann Arbor, MI.
Rockson, "The lymphatics and the inflammatory response: lessons learned from human lymphedema", Lymphatic research and biology, 2013, pp. 117-120, vol. 11, No. 3, Mary Ann Liebert, Inc., New Rochelle, NY.
Nakamura et al., "Anti-Inflammatory Pharmacotherapy with Ketoprofen Ameliorates Experimental Lymphatic Vascular Insufficiency in Mice", PloS one, Dec. 2009, p. 1-7, vol. 4,Issue 12, e8380, PLOS, San Francisco, CA.
Tian et al., "Blocking macrophage leukotriene b4 prevents endothelial injury and reverses pulmonary hypertension", Science translational medicine, Aug. 28, 2013, pp. 1-32, vol. 5, Issue 200, American Association for the Advancement of Science, Washington, D.C.
Yoon et al., "Sphingosine-1-phosphate promotes lymphangiogenesis by stimulating S1P1/G i/PLC/Ca 2+ signaling pathways", Blood, Aug. 15, 2008, pp. 1129-1138, vol. 112, No. 4, American Society of Hematology, Washington, D.C.
Pham et al., "Lymphatic endothelial cell sphingosine kinase activity is required for lymphocyte egress and lymphatic patterning", The Journal of experimental medicine, Jan. 18, 2010, pp. 17-27, Vol., The Rockefeller University Press, Birmingham, Alabama.
Zheng et al., "Lymphangiogenic factors, mechanisms, and applications", The Journal of clinical investigation, Mar. 2014, pp. 878-887, vol. 124 No. 3, American Society for Clinical Investigation, Ann Arbor, MI.
Anelli et al., "Role of sphingosine kinase-1 in paracrine/transcellular angiogenesis and lymphangiogenesis in vitro", FASEB journal, Mar. 24, 2010, pp. 2727-2738, vol. 24 No. 8, Federation of American Societies for Experimental Biology.
Fatima et al., "Murine Notch1 is required for lymphatic vascular morphogenesis during development", Developmental dynamics, Jul. 2014, pp. 957-964, vol. 243, Issue 7, Wiley, Hoboken, NJ.
Kunkel et al., "Targeting the sphingosine-1-phosphate axis in cancer, inflammation and beyond", Nature reviews Drug discovery, Sep. 2013, pp. 688-702, 12(9), Macmillan Publishers Limited, Basingstoke, United Kingdom.

\* cited by examiner

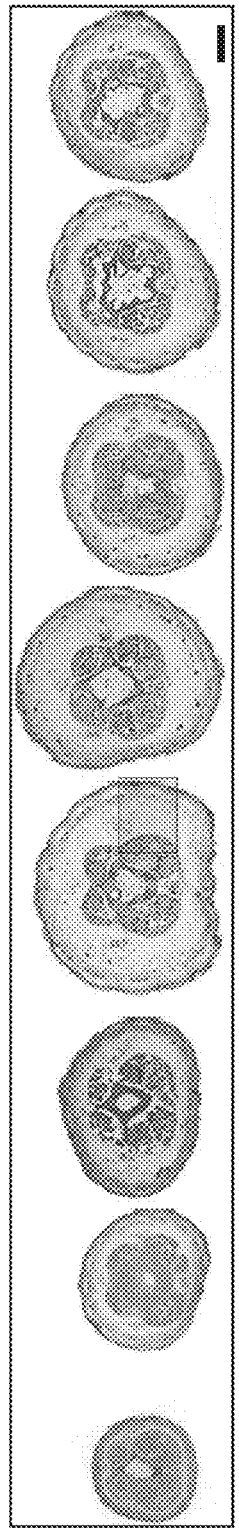
FIG. 1E
FIG. 1F
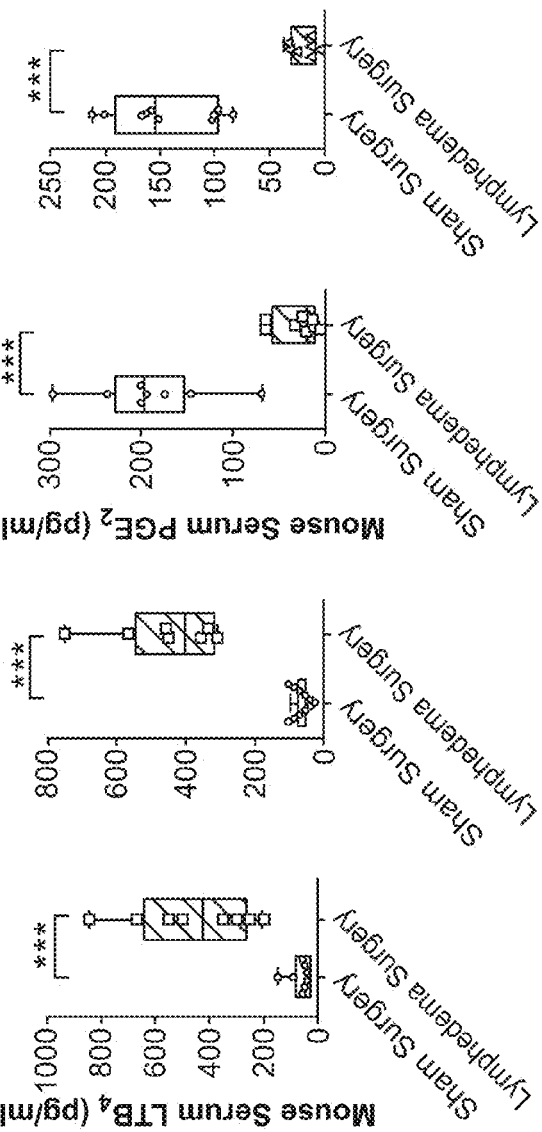
FIG. 1G
FIG. 1H

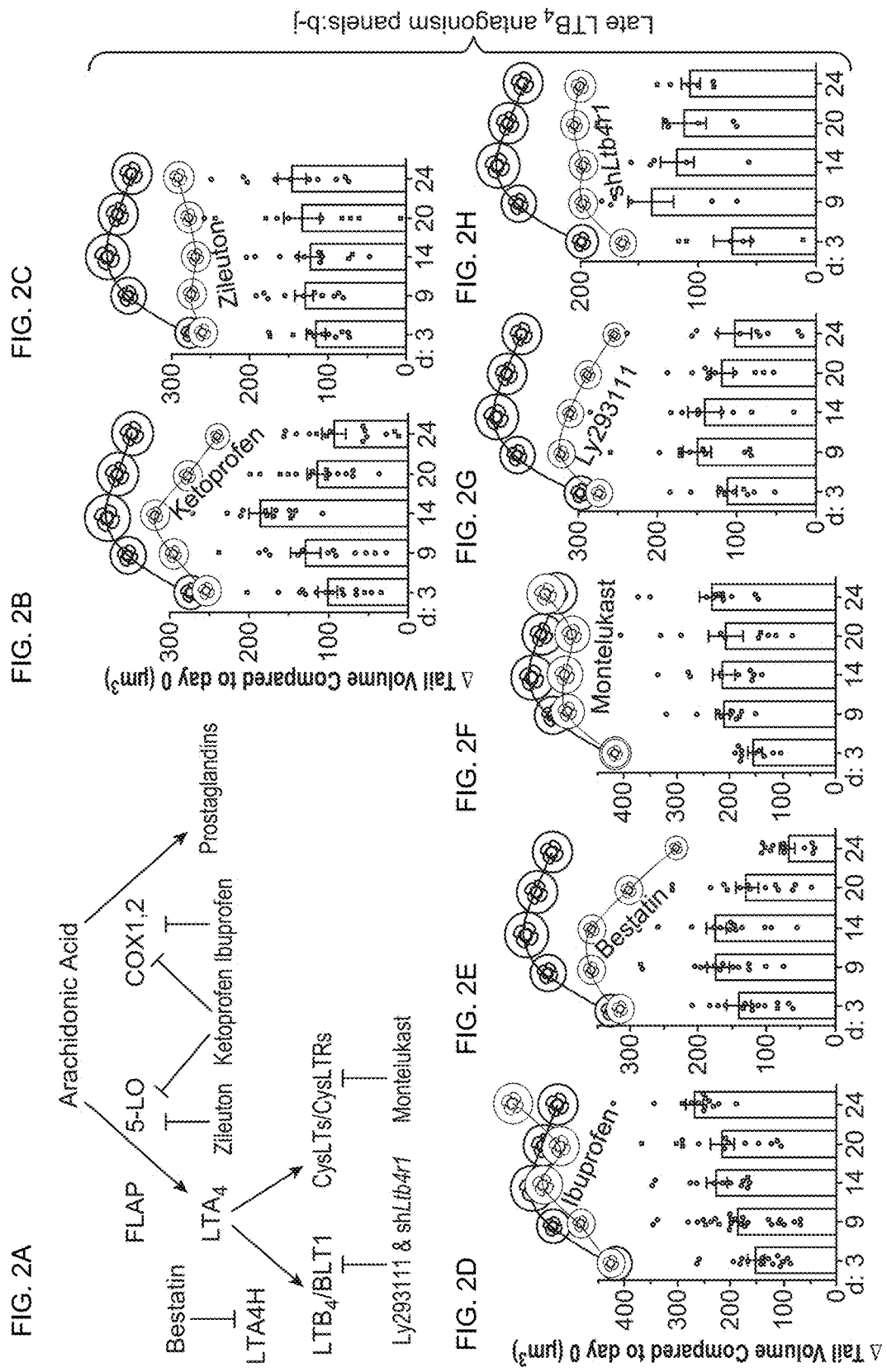

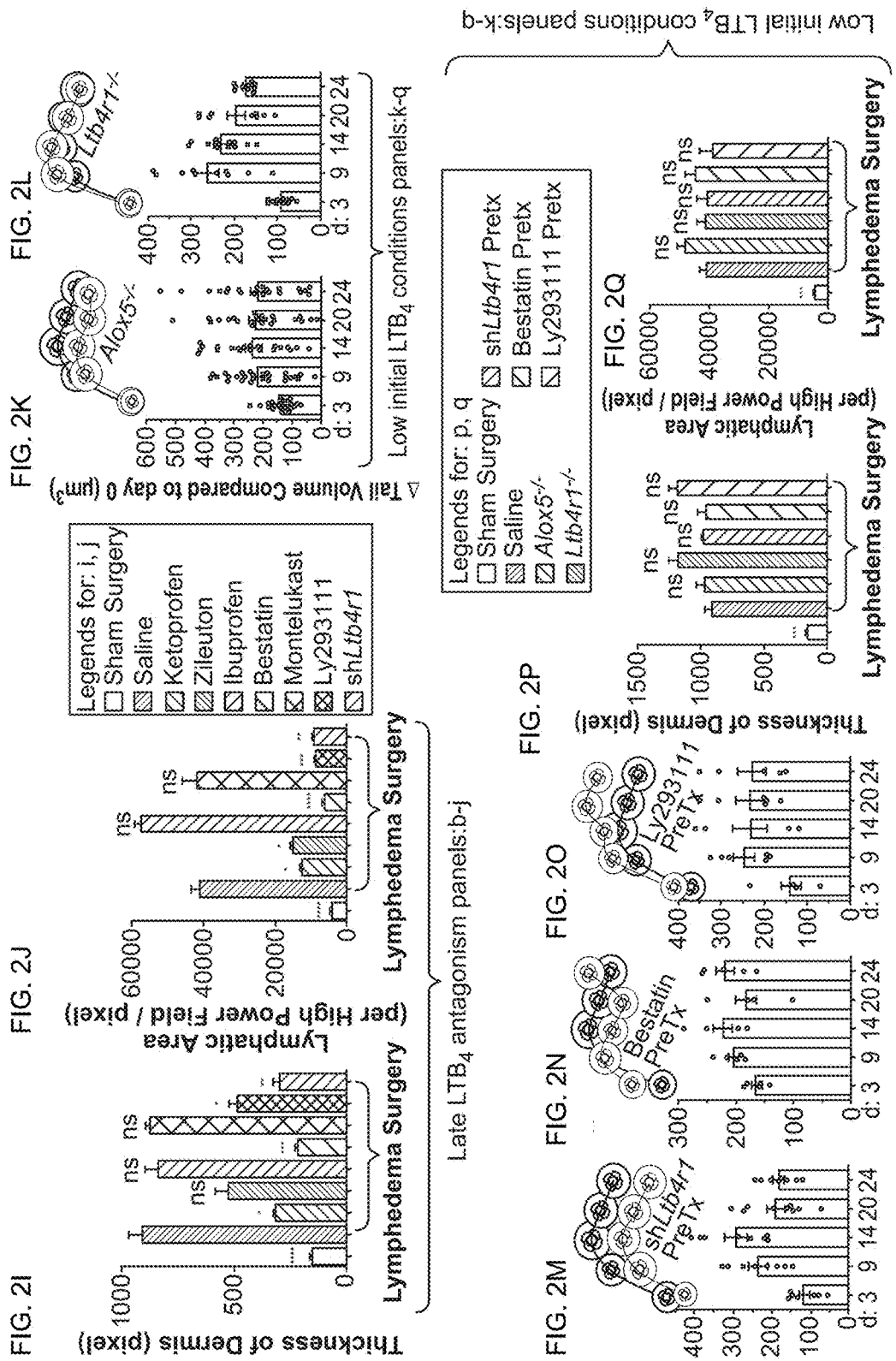

FIG. 2R

Importance of Timing of LTB$_4$ Antagonism on Mouse Tail Skin Angiogenic and Inflammatory Related Genes

| Group | | Fold Change |||||||||||| |||||
|---|---|---|---|---|---|---|---|---|---|---|---|---|---|---|---|---|
| | | Angiogenesis |||||||||| | Inflammation |||||
| | | Mmp9 | ANGPT1 | ANG | Vegfr1 | ENG | Nrp1 | Fn1 | Pdgfrβ | Tie2 | ANGPT2 | Vegfr2 | Vegfa | S1pr1 | Cxcl1 | Cxcl2 | Cxcl5 | Il1β | Stat6 | Tnfα |
| Late LTB$_4$ antagonism | Bestatin | 4.6 | 1.9 | 1.5 | 2.8 | 2.3 | 2.6 | 3.0 | 2.7 | 2.3 | 1.5 | 2.9 | 1.4 | 2.1 | -2.0 | -4.8 | -5.2 | -1.0 | -5.7 | -1.2 |
| | shLtb4r1 | 3.8 | 2.0 | 1.1 | 1.9 | 2.3 | 1.8 | 2.1 | 1.4 | 1.5 | 1.9 | 2.8 | 1.7 | 1.9 | -2.7 | -1.4 | -4.7 | -1.2 | -3.6 | -1.1 |
| Low initial LTB$_4$ conditions | Alox5-/- | -64.7 | -8.3 | -5.3 | -3.9 | -3.2 | -2.8 | -12.5 | -4.1 | -20.0 | -2.4 | -6.6 | -4.5 | 2.9 | 4.0 | 4.5 | 4.5 | 4.6 | 2.4 | 1.5 |
| | shLtb4r1 Pretx | -13.1 | -8.5 | -10.1 | -4.0 | -3.6 | -3.8 | -9.6 | -5.9 | -7.9 | -1.9 | -4.4 | -4.6 | 2.4 | 2.7 | 4.8 | 4.6 | 9.5 | 2.8 | 2.0 |

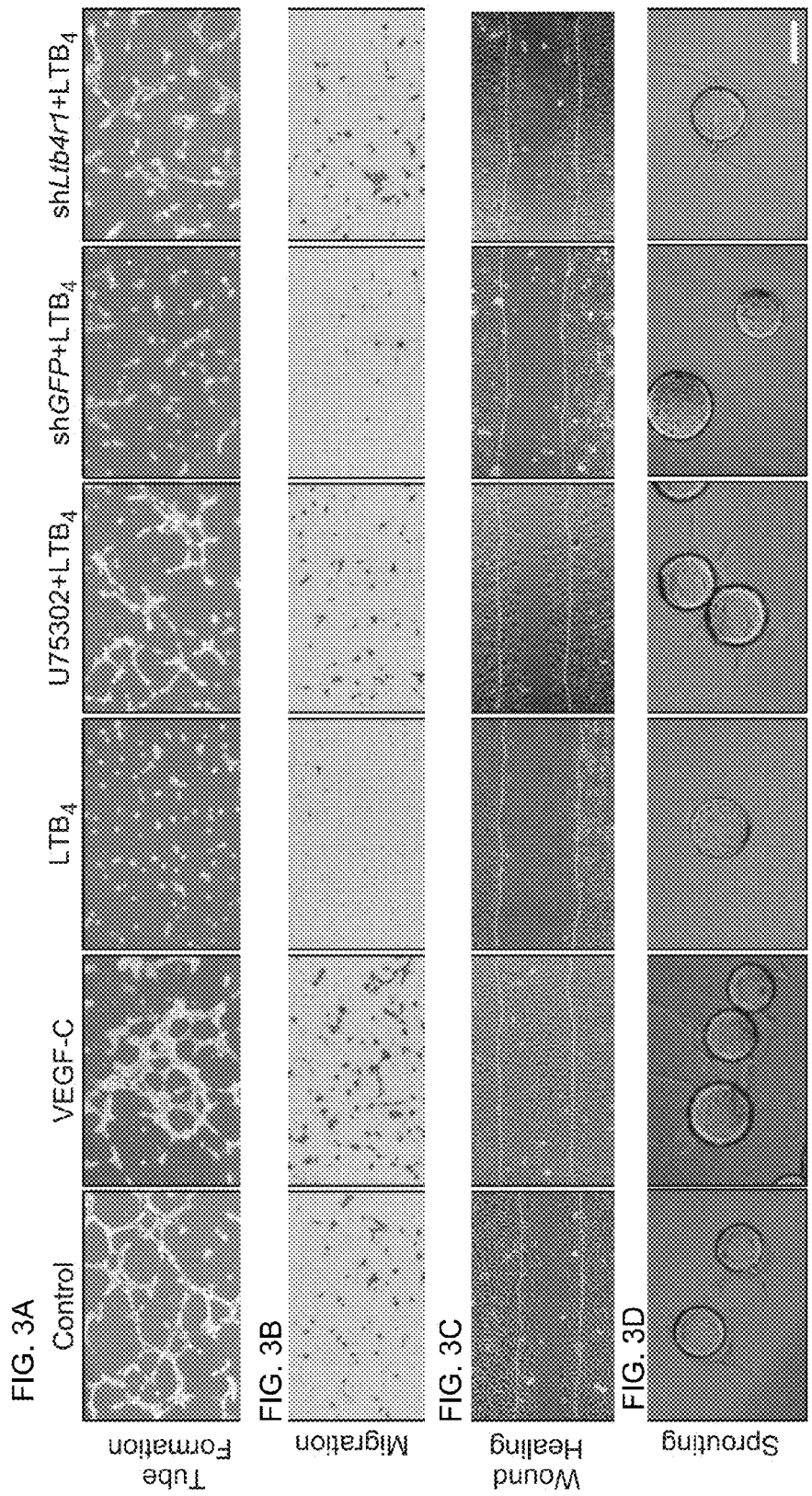

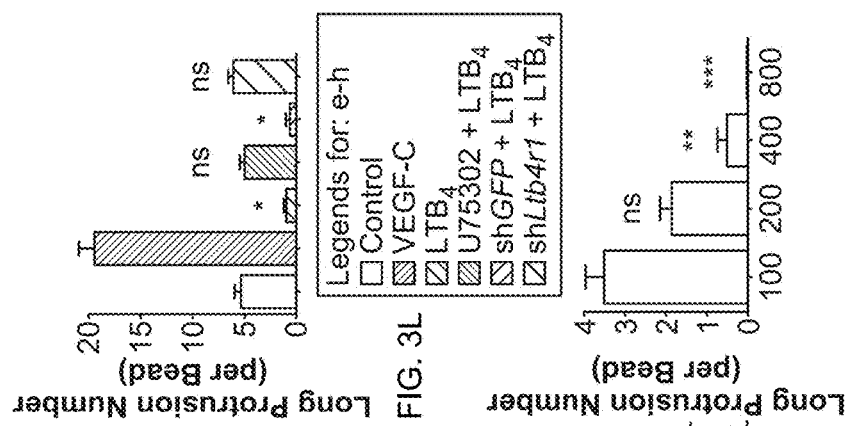
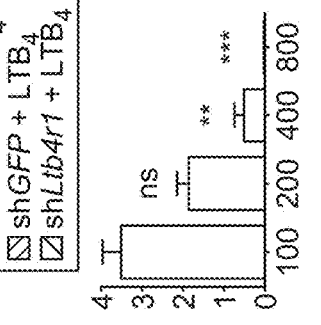
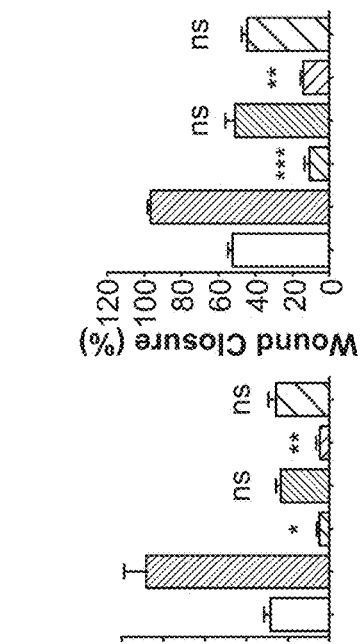
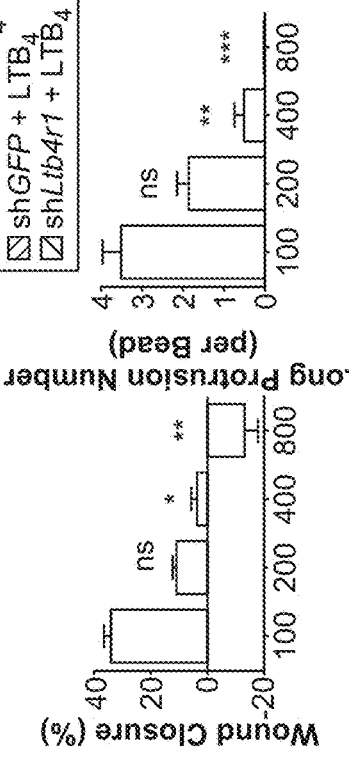
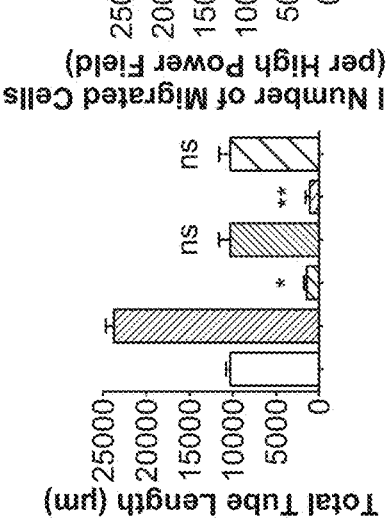
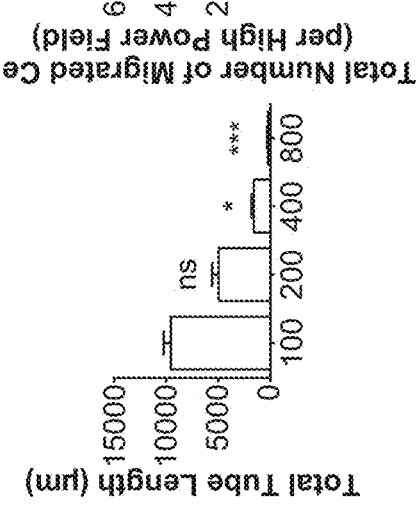
FIG. 3E  FIG. 3F  FIG. 3G  FIG. 3H
FIG. 3I  FIG. 3J  FIG. 3K  FIG. 3L Legends for: m,n,o,p
☐ Control
▨ LTB$_4$
▨ LTB$_4$ + S1P
▨ S1P
▨ sh$S1pr1$ + S1P
▨ sh$Dll4$ + S1P
▨ DAPT + S1P

*In vitro* lymphangiogensis

FIG. 5D
FIG. 5E
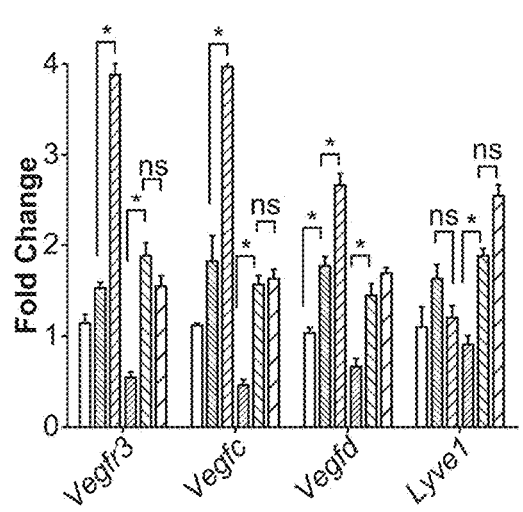
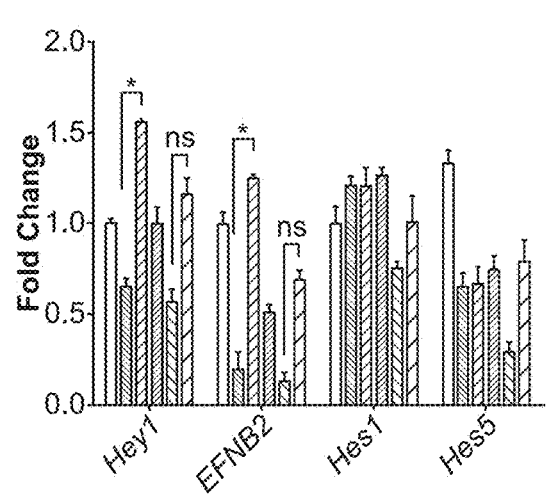
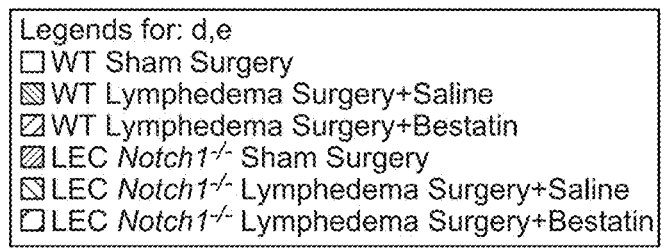

FIG. 6A

Demographics of the controls and patients - $LTB_4$ and $PGE_2$ analysis

| Patient ID: | Age: | Sex: | BMI | WHO Class (1-3) | Primary /Secondary | Duration of Disease (year) | $LTB_4$ LC-MS/MS (pg/ml) | $LTB_4$ ELISA (pg/ml) | $PGE_2$ LC-MS/MS (pg/ml) | $PGE_2$ ELISA (pg/ml) |
|---|---|---|---|---|---|---|---|---|---|---|
| C1 | 84 | M | n/a | n/a | n/a | n/a | 101.5 | 54.1 | 101.2 | 56.3 |
| C2 | 31 | M | n/a | n/a | n/a | n/a | 56.1 | 12.2 | 141.1 | 48.3 |
| C3 | 27 | F | n/a | n/a | n/a | n/a | 15.2 | 66.0 | 85.1 | 113.5 |
| C4 | 21 | M | n/a | n/a | n/a | n/a | 100.1 | 28.0 | 400.2 | 353.4 |
| C5 | 31 | M | n/a | n/a | n/a | n/a | 78.5 | 52.6 | 90.1 | 64.9 |
| C6 | 33 | M | n/a | n/a | n/a | n/a | 165.0 | 117.4 | 150.2 | 208.5 |
| C7 | 32 | M | n/a | n/a | n/a | n/a | 46.1 | 106.5 | 955.8 | 868.2 |
| C8 | 30 | F | n/a | n/a | n/a | n/a | 101.2 | 124.6 | 758.6 | 658.7 |
| C9 | 60 | M | n/a | n/a | n/a | n/a | 166.7 | 162.5 | 1574.4 | 1049.8 |
| C10 | 61 | M | n/a | n/a | n/a | n/a | 89.7 | 77.1 | 367.1 | 274.3 |
| C11 | 34 | M | n/a | n/a | n/a | n/a | 269.0 | 203.9 | 50.7 | 43.3 |
| C12 | 78 | M | n/a | n/a | n/a | n/a | 144.1 | 158.3 | 30.1 | 49.9 |
| C13 | 23 | M | n/a | n/a | n/a | n/a | 98.5 | 71.0 | 556.2 | 33.5 |
| C14 | 24 | F | n/a | n/a | n/a | n/a | 80.4 | 104.7 | 240.5 | 142.6 |
| C15 | 23 | M | n/a | n/a | n/a | n/a | 190.5 | 120.6 | 151.5 | 233.3 |
| C16 | 37 | M | n/a | n/a | n/a | n/a | 135.4 | 103.3 | 200.2 | 198.6 |
| C17 | 25 | M | n/a | n/a | n/a | n/a | 199.6 | 50.8 | 166.0 | 227.0 |
| C18 | 55 | F | n/a | n/a | n/a | n/a | 213.2 | 215.4 | 279.7 | 692.2 |
| C19 | 60 | F | n/a | n/a | n/a | n/a | 48.2 | 105.1 | 258.1 | 457.6 |
| C20 | 58 | F | n/a | n/a | n/a | n/a | 40.2 | 50.1 | 386.7 | 201.2 |
| C21 | 52 | F | n/a | n/a | n/a | n/a | 49.5 | 35.4 | 366.3 | 135.3 |
| P1 | 77 | F | 37.68 | 2 | Secondary | 5 | 566.2 | 498.2 | 28.4 | 7.8 |
| P2 | 27 | M | 22.97 | 2 | Primary | 8 | 412.1 | 1327.5 | 26.5 | 6.1 |
| P3 | 44 | F | 24.58 | 2 | Secondary | 38 | 679.9 | 1094.7 | 56.9 | 78.4 |
| P4 | 85 | F | 26.18 | 2 | Secondary | 4 | 245.2 | 146.7 | 94.9 | 84.9 |
| P5 | 59 | F | 29.27 | 2 | Secondary | 22 | 510.2 | 1486.3 | 16.4 | 210.8 |
| P6 | 62 | F | 33.08 | 2 | Secondary | 5 | 857.1 | 854.9 | 108.2 | 31.8 |
| P7 | 68 | F | 26.19 | 2 | Secondary | 4 | 955.2 | 1015.6 | 12.0 | 26.1 |
| P8 | 69 | M | 51.35 | 2 | Secondary | 13 | 561.3 | 756.0 | 15.2 | 101.9 |
| P9 | 76 | F | 48.53 | 3 | Primary | childhood | 987.1 | 812.2 | 58.3 | 2.0 |
| P10 | 71 | F | 23.67 | 2 | Secondary | 4 | 847.2 | 916.4 | 54.1 | 6.2 |
| P11 | 40 | M | 21.7 | 1 | Secondary | 6 | 821.1 | 900.6 | 39.1 | 80.4 |
| P12 | 53 | M | 28.4 | 2 | Secondary | 3 | 311.1 | 208.6 | 50.2 | 45.0 |
| P13 | 65 | F | 23.67 | 2 | Secondary | 10 | 401.1 | 375.1 | 39.5 | 33.4 |
| P14 | 47 | F | 27.03 | 2 | Secondary | 5 | 495.2 | 153.0 | 26.5 | 3.5 |
| P15 | 73 | F | 23.92 | 2 | Secondary | 14 | 645.1 | 531.0 | 48.4 | 12.3 |
| P16 | 61 | F | 26.87 | 2 | Secondary | 7 | 600.1 | 505.8 | 65.1 | 48.2 |
| P17 | 42 | F | 20.81 | 2 | Secondary | 14 | 991.1 | 827.6 | 95.5 | 105.7 |
| P18 | 69 | F | 24.2 | 2 | Secondary | 18 | 500.1 | 487.4 | 36.0 | 158.6 |
| Statistics | $P<0.01$ | n/a | n/a | n/a | n/a | n/a | $P<0.0001$ | $P<0.0001$ | $P<0.0001$ | $P<0.0001$ |

LTB4 INHIBITION TO PREVENT AND TREAT HUMAN LYMPHEDEMA

CROSS-REFERENCE

This application claims the benefit and is a 371 application of PCT Application No. PCT/US2016/022132, filed Mar. 11, 2016, which claims benefit of U.S. Provisional Patent Application No. 62/133,086, filed Mar. 13, 2015, which application is incorporated herein by reference in its entirety.

BACKGROUND OF THE INVENTION

Lymphedema occurs with obstruction, destruction, or functional inadequacy of lymph vessels. The resultant accumulation of interstitial fluid, containing high molecular weight proteins and other cellular debris, produces a condition with a complex biology that extends far beyond edema. Lymphedema may be primary or secondary (acquired). Primary lymphedema can be present from birth (congenital lymphedema), may occur during puberty (lymphedema praecox), and less often presents later in life (lymphedema tarda). Acquired lymphedema is a common, important and often devastating consequence of successful surgical and radiotherapy of breast cancer and many other malignancies. It is characterized by the impaired transport and consequent accumulation of interstitial fluid, with accompanying swelling of subcutaneous tissues. Secondary lymphedema can also result from trauma or infection, including dermatophytosis in the foot.

Lymphedema may be complicated by direct infection of the vascular channels (lymphangitis), which is manifested by chills, high fever, toxicity, and a red, hot, swollen extremity. Lymphangitic streaks may be seen in the skin, and the recipient lymph nodes are usually enlarged and tender. These features differentiate lymphangitis from acute thrombophlebitis. Lymphedema patients are also prone to recurrent attacks of soft tissue bacterial infection (cellulites or erysipelas); the accompanying systemic signs of infection are often blunted. These recurrent infections are the source of substantial morbidity and are difficult to prevent or eradicate.

In lymphedema, the lymphatic transport capacity is not sufficient to offset the lymphatic load. This causes the normal volume of interstitial fluid formation to exceed the rate of lymphatic return, resulting in the accumulation of interstitial fluid, enriched by the content of high molecular weight proteins. The result is a high-protein edema, or lymphedema, with protein concentrations of 1.0-5.5 g/mL. The high oncotic pressure in the interstitium favors the continued accumulation of water.

Accumulation of interstitial fluid leads to massive dilatation of the remaining outflow tracts, along with valvular incompetence that causes reversal of flow from subcutaneous tissues into the dermal plexus. A marked inflammatory reaction is initiated. Macrophage activity is increased, resulting in destruction of elastic fibers and production of fibrosclerotic tissue. Tissue inflammation in lymphedema may reflect either an active or passive consequence of impaired immune traffic. The result of this inflammatory reaction is a change from the initial pitting edema to the increasingly brawny non-pitting edema characteristic of the later stages of lymphedema. The overlying skin becomes thickened, forming thick scaly deposits of keratinized debris, and may display a warty verrucosis. Cracks and furrows often develop and accommodate debris and bacteria, facilitating soft tissue infection and leading to lymphorrhea, the external leakage of lymph through the skin.

In the United States, the highest incidence of lymphedema is observed following breast cancer surgery, particularly among those who undergo radiation therapy following axillary lymphadenectomy. Among this population, 10-40% develop some degree of ipsilateral upper extremity lymphedema. Worldwide, 90 million cases of lymphedema are estimated to exist, with filariasis being the most common cause. Prevalence estimates of lymphedema, both in the United States and worldwide, are indirect, and likely reflect an underestimation of the burden of disease.

Patients with chronic lymphedema for more than 10 years have a small, but identifiable, risk of developing lymphangiosarcoma. Patients with this tumor commonly present with a reddish purple discoloration or nodule that tends to form satellite lesions. This tumor is highly aggressive, requires radical amputation of the involved extremity, and has a very poor prognosis because of its propensity for early, aggressive metastasis. Other complications of lymphedema include recurrent bouts of cellulitis and/or lymphangitis, severe functional impairment, and, rarely, the need for amputation. Complications following surgery are common and include partial wound dehiscence, seroma, hematoma, skin necrosis, and exacerbation of foot or hand edema.

Surgical treatment is palliative, not curative, and it does not obviate the need for continued medical therapy. Moreover, it is rarely indicated as the primary treatment modality. Many surgical procedures have been advocated. None of the surgical interventions has a clearly documented favorable long-term results.

Improved treatment of lymphedema, both primary and secondary (or acquired), is of great clinical and scientific interest. The present invention addresses this need by providing new methods for treating lymphedema, for reducing the risk of incurring the complications of lymphedema, for preventing or at least slowing the progression of lymphedema, for reversing the fluid accumulation or, in later stages of the disease, tissue architecture changes that accompany disease progression, and for preventing the disease from developing in patients likely to develop it.

Publications of interest, each specifically incorporated by reference, for the artisan contemplating this disclosure may include Mortimer & Rockson *The Journal of Clinical Investigation* 124, 915-921 (2014); Rockson *Lymphatic research and biology* 11, 117-120 (2013); Nakamura et al. *PloS one* 4, e8380 (2009); Tian, W., et al. *Science translational medicine* 5, 200ra117 (2013); Yoon, C. M., et al. *Blood* 112, 1129-1138 (2008); Pham, et al. *The Journal of experimental medicine* 207, 17-27 (2010); Zheng et al. *The Journal of clinical investigation* 124, 878-887 (2014); Anelli et al. *FASEB journal* 24, 2727-2738 (2010); Fatima, et al. *Developmental dynamics* 243, 957-964 (2014); Kunkel, et al. *Nature reviews. Drug discovery* 12, 688-702 (2013).

SUMMARY OF THE INVENTION

Compositions and methods for the prevention or treatment of lymphedema are provided. In the methods of the invention, therapeutic compositions are administered to an individual suffering from lymphedema, or at risk of developing lymphedema, which therapeutic compositions inhibit the synthesis or activity of $LTB_4$.

In some embodiments, an effective dose of an inhibitor of $LTB_4$ is administered to an individual having lymphedema, including without limitation established lymphedema, for a period of time sufficient to decrease or reverse tissue pathology of the affected (lymphadematous) tissue relative to an untreated control group. Treatment may be continued as required for maintenance of the therapeutic benefit: where required, maintenance therapy may be maintained at the same dosage and schedule as previous treatment or may be achieved by transitioning to an alternative maintenance schedule, e.g. at a lower dose, less frequent dose, and the like. In some embodiments, the treating physician can determine that the treatment is efficacious by verifying a change in the architecture of the affected tissue. The tissue may be assayed by any number of means as described herein to verify therapeutic benefit, if visual inspection alone is insufficient. A convenient measure of efficacy in some applications is dermal thickness, although those of skill in the art will understand upon contemplation of this disclosure that various indicia can be used to monitor treatment and determine efficacy.

The present invention represents a significant advance in the treatment of lymphedema. In some embodiments, the patient treated has established lymphedema, and treatment results in changes to the architecture of the affected tissue such that, after treatment, the affected tissue more closely resembles the architecture of unaffected tissue than prior to (or without any) treatment. In some embodiments, one or more clinical indicia of lymphedema are assayed over the period of time for treatment. The time period may be about 1 week, about 2 weeks, about 3 weeks, about 1 month, about 2 months, about 3 months, about 4 months, about 6 months, or longer.

It is anticipated that practice of the invention will initially be largely to the advantage of patients with established lymphedema and that, as treatment proves efficacious in slowing disease progression and reversing the tissue architecture changes that accompany advanced disease, physicians will apply these methods to patients ever earlier in the disease process. With safe and highly efficacious agents, such as ubenimex which is described and exemplified herein, physicians may one day employ them largely as prophylactic or early disease treatment agents, thus offering the promise of one day largely eliminating this debilitating disease.

Thus, in some embodiments of the invention, an individual with established lymphedema is treated with an effective dose of an inhibitor of LTB4 such as ubenimex for a period of time sufficient to stabilize or reverse the disease. Such individuals may have pathological alterations of the skin characteristic of established disease, e.g. stage 1, 2 or 3 lymphedema. The methods of treatment according to the present invention can result in reversal of disease conditions, exemplified by partial or complete reversal of skin pathologies in affected tissues. The therapy may be maintained after partial or complete reversal of skin pathologies.

In some embodiments, the volume of the affected limb(s), may be measured over the time period, e.g. to monitor treatment, determine efficacy, etc. In some embodiments, where the volume is largely due to fluid accumulation, more typical of very early stages of the disease, volume may decrease by 10 milliliters to 100 milliliters or more from the affected tissue following treatment.

In some embodiments, an effective dose of an inhibitor of $LTB_4$ is provided to an individual susceptible to lymphedema, including without limitations individuals that have undergone surgery or radiation for cancer. As noted, secondary, or acquired lymphedema, is typically acquired as a result of cancer treatment and is much more common than primary lymphedema.

In some embodiments, therefore, the individual to be treated has, or has been, or is being treated for cancer but has not yet developed lymphedema. In other embodiments, the patient has lymphedema (stage 0 to 3) as a result of cancer therapy, e.g. surgery or radiotherapy or other therapy damaging to the lymphatic system. In some embodiments, the individual has been treated with surgery, typically as a result of cancer diagnosis and treatment but other surgeries affecting the lymph nodes can cause lymphedema treatable in accordance with the invention. In such embodiments, treatment with an inhibitor of $LTB_4$ may commence immediately following surgical wound healing, or may commence at a time following surgical wound healing, including after some or even substantial wound healing has occurred, e.g., 3-14 days after surgery, but before a patient has been diagnosed as having stage 0 lymphedema.

In some embodiments the individual has been treated with radiotherapy, which itself may follow surgery for cancer therapy. In such embodiments, treatment with an inhibitor of $LTB_4$ may commence immediately during radiotherapy, following radiotherapy, or may commence at a time following radiotherapy, including after some or even substantial wound healing has occurred, as above, but before a patient has been diagnosed as having stage 0 lymphedema.

The invention can also be practiced in other prophylactic modes, including after successful treatment. Some patients may be treated in accordance with the invention and obtain complete or significantly complete recovery and not benefit from further treatment. Other patients, however, may benefit from continued administration of an LTB4 inhibitor after treatment has been successful to prevent recurrence of the disease. Thus, for prophylactic purposes of lymphedema prevention, following treatment by the methods of the invention, the architecture of the skin of the affected patient, e.g. skin of the extremities, remains with a substantially normal architecture consistent with successful treatment. Following prophylactic treatment with the methods of the invention, the volume of tissue, e.g. upper extremities, lower extremities, etc. should be stable over time, relative to a control group in the absence of treatment. The time period in which to see treatment benefit may be about 1 week, about 2 weeks, about 3 weeks, about 1 month, about 2 months, about 3 months, about 4 months, or more. In some embodiments, the volume and/or structure of the affected or at risk tissue, i.e. the lymphadematous tissue, is measured or otherwise assayed or assessed at various points over the time period, e.g. at least at the beginning and some designated endpoint for testing. In some embodiments, the architecture of the affected tissue is assayed by bioimpedence or dermal thickness measurements or by histological assessment. In some embodiments, the architecture of the affected tissue after treatment resembles or more closely resembles the architecture of unaffected tissue.

In some embodiments, the inhibitor of $LTB_4$ is an inhibitor of leukotriene $A_4$ hydrolase ($LTA_4H$), which has an epoxide hydrolase activity that converts leukotriene $A_4$ ($LTA_4$) into $LTB_4$. In such embodiments, the leukotriene inhibitor is a selective or competitive inhibitor of $LTA_4H$. The leukotriene inhibitor can also be a pharmaceutically acceptable salt thereof a $LTA_4H$ inhibitor. In various embodiments, the $LTA_4H$ inhibitor is selected from the group consisting of ubenimex (bestatin), CTX4430, JNJ26993135, JNJ40929837, DG051, BI 691751, 4-(4-benzylphenyl)thiazol-2-amine, SC-57461A, and analogs of any of the foregoing with $LTA_4H$ inhibitory activity.

In other embodiments, the $LTB_4$ inhibitor is an antagonist of an $LTB_4$ receptor, e.g. $LTB_4$ receptor 1 (BLT1) or $LTB_4$ receptor 2 (BLT2). In various embodiments, the BLT1/BLT2 antagonist is selected from the group consisting of LY293111, ONO4057, CP195543, CGS25019C, Biomed 101, BIIL284BS, DW1350, LY255283, and analogs of any of the foregoing with BLT1/BLT2 antagonist activity.

In another embodiment, the $LTB_4$ inhibitor is an inhibitor of arachidonate 5-lipoxygenase (5-LO) or 5-LO activating protein (FLAP). 5LO acts upstream of $LTA_4H$, and catalyzes oxidation of arachidonic acid to yield 5-HpETE, which is then converted to $LTA_4$. In various embodiments, the 5-LO/FLAP inhibitor is a 5-LO inhibitor. In various embodiments, the 5-LO inhibitor is selected from the group consisting of zileuton, MK0633, ZD2138, and VIA2291591, and analogs of any of the foregoing with 5-LO inhibitory activity. In various embodiments, the 5-LO/FLAP inhibitor is a FLAP inhibitor. In various embodiments, the FLAP inhibitor is selected from the group consisting of DG031, MK886, GSK MK591, and analogs of any of the foregoing with FLAP inhibitory activity. In some embodiments, the 5-LO inhibitor is not ketoprofen.

In various embodiments, the $LTB_4$ inhibitor, or pharmaceutically acceptable salt thereof, is administered orally. In one important embodiment, the LTB4 inhibitor is orally administered ubenimex delivered in a daily dose ranging from 10 to 500 mg administered once, twice, or no more than thrice daily (e.g., 150 mg TID; 500 mg QD; 250 mg BID are all daily doses within this range). In some embodiments the therapeutically effective dose of a $LTA_4H$ inhibitor, or an analog or pharmaceutically acceptable salt thereof, is administered orally. In various of these embodiments, the therapeutically effective dose is administered once daily. In some embodiments administered twice daily. In some embodiments the therapeutically effective dose is administered 3 times day. In some embodiments the therapeutically effective dose is administered 4 times a day. In various of these embodiments, the therapeutically effective dose is administered on consecutive days for at least a week, at least a month, at least a year, or on an as needed basis for the rest of the patient's life.

The therapeutically effective dose of a $LTA_4H$ inhibitor, including without limitation ubenimex or analog of ubenimex, or pharmaceutically acceptable salt thereof, can be about 10-500 mg/day, about 10-1500 mg/day, about 10-1000 mg/day, about 10-500 mg/day, about 50-500 mg/day, about 100-500 mg/day, about 200-500 mg/day, about 50-400 mg/day, about 100-200 mg/day, or about 120-180 mg/day. A $LTA_4H$ inhibitor (e.g., ubenimex or analog or ubenimex) or pharmaceutically acceptable salt thereof, can be administered to a subject at about 20-80 mg twice a day or about 20-80 mg three times a day. A $LTA_4H$ inhibitor (e.g., ubenimex or analog or ubenimex) or pharmaceutically acceptable salt thereof, can be administered to a subject at about 20 to 500 mg twice or three times a day, about 20-400 mg twice or three times a day, about 20-300 mg twice or three times a day, about 20-250 mg twice or three times a day, about 20-200 mg twice or three times a day, about 20-180 mg twice or three times a day, about 50-180 mg twice or three times a day. For example, a $LTA_4H$ inhibitor (e.g., ubenimex or an analog of ubenimex) or pharmaceutically acceptable salt thereof, is administered at about 60 mg twice a day or about 60 mg three times a day. In some embodiments the $LTA_4H$ inhibitor may be administered at higher doses, e.g., 150 mg twice or three times a day, or at intermediate doses in between, in others.

The methods of the invention include administration of a therapeutically effective amount of at least one additional active agent other than a $LTA_4H$ inhibitor. In some embodiments the additional agent is a diuretic. Also, the invention provides a pharmaceutical formulation containing ubenimex and an additional active agent, such as a diuretic; antibiotics, retinoids, etc. The invention includes a method of treating lymphedema, where the method includes a combination therapy in which a patient in need of treatment is administered an effective dose of an $LTB_4$ inhibitor, e.g., a $LTA_4H$ inhibitor, such as ubenimex, in combination with one or more drugs or other therapies approved for the treatment of lymphedema.

In various embodiments, the $LTB_4$ inhibitor is administered in combination with one or more other drugs useful in preventing or treating lymphedema. In some of these embodiments, two or more $LTB_4$ inhibitors are administered in accordance with the invention. For example, inhibitors from the $LTA_4H$ inhibitor and BLT1/BLT2 antagonist classes of $LTB_4$ inhibitors can be administered in combination in accordance with the invention.

In other aspects, the compounds provided by the invention are used in the manufacture of a medicament for the treatment or prevention of lymphedema, wherein said medicament is a $LTB_4$ inhibitor (e.g., a $LTA_4H$ inhibitor, or pharmaceutically acceptable salt thereof). In various embodiments, the medicament is formulated for oral administration, including both immediate release and sustained release pharmaceutical formulations. In all of these embodiments, the invention provides unit dose forms of the medicament.

The methods can further comprise continuing the therapy if the therapy is determined to be efficacious. The methods can comprise maintaining, tapering, reducing, or stopping the administered amount of a compound or compounds in the therapy if the therapy is determined to be efficacious. The methods can comprise increasing the administered amount of a compound or compounds in the therapy if it is determined not to be efficacious or likely to be more efficacious if dosing is increased in daily amount or via a change in the administration schedule. Alternatively, the methods can comprise stopping therapy if it is determined not to be efficacious.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1J: 5-LO/$LTB_4$ signaling is increased in human and mouse lymphedema. (FIG. 1A) Overview of the eicosanoid pathway. Arachidonic acid is metabolized into LTs through the 5-LO pathway or into prostaglandins via the COX1/COX2 pathway. Ketoprofen is a dual-functional inhibitor of both pathways. (FIG. 1B,1C) Serum LTB4 and PGE2 were measured in healthy controls (n=21) and in lymphedema (n=18) patients by LC-MS/MS and ELISA. (FIG. 1D) Natural progression of the mouse-tail model of acquired lymphedema. Tail volume at each measurement time point was calculated as Δ volume from d0. Cartoon representations of the cross-sectional view of lymphedematous tails were created to illustrate lymphedema progression.

Data are presented in scatter-dot plots showing mean and SEM; ns, not significant, *P<0.001, P<0.0001 by the Kruskal-Wallis test followed by the Dunn's multiple comparisons test for post hoc analyses. (FIG. 1E) Representative histologies of mouse tails at designated time points of lymphedema evolution. Scale bar, 500 µm; n=5. (FIG. 1F) Inset of d14 H&E image of panel e. Lymphatic dilation and dermal thickening are indicated. Scale bar, 200 µm. (FIG. 1G, 1H) Circulating LTB4 or PGE2 levels were measured in mice after sham surgery or lymphedema surgery by LC-MS/MS and ELISA. n=8. (FIG. 1I) Representative immunofluorescent staining of VEGFR3 in Prox1-Cre-ER-tdTomato mouse tail skin on d24 following sham or lymphedema surgery. DAPI stains nuclei; scale bar, 20 µm; white arrows indicate dilated lymphatics; n=5. (FIG. 1J) Representative microlymphangiography. Scale bars, 100 µm. For panels b, c, g and h, data are presented in box-and-whiskers plots showing minimal to maximal values and all data points, *P<0.001, ****P<0.0001 by the Mann-Whitney test.

FIG. 2A-2R: Blocking late, but not early, $LTB_4$ signaling ameliorates experimental lymphedema. (FIG. 2A) Schematic summary of therapies (blue), targeting different eicosanoid pathways, tested in the study. (FIG. 2B-2H) Serial tail-volume measurements at each time point over 24d. To block $LTB_4$ signaling after wound closure (late $LTB_4$ antagonism), all therapies were started on post-surgery d3. Treatments targeting both 5-LO and COX1/COX2 (ketoprofen, FIG. 2B, n=15), 5-LO (zileuton, FIG. 2C, n=10), $LTA_4H$ (bestatin, FIG. 2E, n=14), BLT1 (Ly293111, FIG. 2G, n=10) or Ltb4r1 (local administration of lentivirus expressing shLtb4r1, FIG. 2H, n=6) demonstrated therapeutic amelioration of lymphedema. Ibuprofen (inhibits COX1, 2, FIG. 2D, n=13) and montelukast (antagonizes CysteinlyLT, FIG. 2F, n=10) did not have beneficial effects. Quantifications of dermal skin thickness (FIG. 2I) and lymphatic area (FIG. 2J) in the d24 mouse tail skin for FIGS. 2B-2H. n=5. (FIG. 2K-2O) Serial tail-volume measurements of conditions with low initial $LTB_4$ signaling before surgery including: $Alox5^{-/-}$ (FIG. 2K, n=25), $Ltb4r1^{-/-}$ (FIG. 2L, n=10), local shLtb4r1 lentivirus injection on d(−7) (shLtb4r1 pretx, FIG. 2M, n=8), bestatin treatment started on d0 (bestatin pretx, FIG. 2N, n=6) and Ly293111 treatment started on d0 (Ly293111 pretx, FIG. 2O, n=6). Quantifications of dermal thickness (FIG. 2P) and lymphatic area (FIG. 2Q) in the d24 tail skin for FIG. 2K-2O. n=5. (FIG. 2R) qRT-PCR measuring transcription of key angiogenic and inflammatory factors in the mouse tail skin. Samples were harvested on d24 following lymphedema surgery from representative late $LTB_4$ antagonist groups (bestatin and shLtb4r1 started on d3) and representative low initial $LTB_4$ conditions ($Alox5_{-/-}$ and shLtb4r1 started on d(−7)). n=5. Data are presented as mean±SEM. For panels FIG. 2B-2H, FIG. 2K-2O, data are presented in scatter-dot plots showing mean and SEM. For panels FIGS. 2I, 2J, 2P, and 2Q, data are presented as mean and SEM. ns, not significant, P<0.01, *P<0.001, ****P<0.0001 compared with saline-treated group (n=14) by the Kruskal-Wallis test followed by the Dunn's multiple comparisons test for post hoc analyses.

FIG. 3A-3L: $LTB_4$ blocks in vitro lymphangiogenesis in a BLT1-dependent manner Representative tube formation assay images (FIG. 3A) and quantitative analysis of total tube length (FIG. 3E) of HLECs cultured with 50 ng/ml VEGF-C, 400 nM $LTB_4$, 10 µM U75302 (a BLT1 inhibitor)+$LTB_4$, or shLtb4r1 expressing lentivirus+$LTB_4$. Representative trans-well migration assay images (FIG. 3B) and quantification of total number of migrated HLECs (-FIG. 3F). Representative wound healing assay images (FIG. 3C) and quantification of invaded area percentage of HLECs (FIG. 3G). Representative fibrin gel sprouting assay images (FIG. 3D) and quantification of long sprouts per bead (FIG. 3H). (FIG. 3I-3L) Quantitative analysis of HLECs cultured with 100 nm, 200 nm, 400 nm or 800 nm $LTB_4$ in tube formation (FIG. 3I), migration (FIG. 3J), wound healing (FIG. 3K) and sprouting (FIG. 3L) assays. Non-target shRNA control transduction particles containing shRNA sequence targeting tGFP (shGFP) were used as control viral particles; scale bar, 100 µm; n=6; data are presented as mean±SEM; ns, not significant, *P<0.05, P<0.01, *P<0.001, ****P<0.0001 compared with control in e-h or compared with $LTB_4$ 100 nm in i-l by the Kruskal-Wallis test followed by the Dunn's multiple comparisons test for post hoc analyses.

(FIG. 4A) Schematic summary of S1P and Notch signaling pathways in reparative lymphangiogenesis. Black arrows show existing pathways. Question mark indicates the unknown relationship between S1P and Notch. (FIG. 4B, 3C) LC-MS/MS analysis quantified S1P concentration in human serum (controls, n=10; lymphedema, n=10) (FIG. 4B) and in mouse blood (sham surgery, n=10; untreated lymphedema, n=10; bestatin-treated lymphedema, n=10) (-FIG. 4C). Data are presented in box-and-whiskers plots showing minimal to maximal values and all data points; *P<0.001, **P<0.0001 by the Mann-Whitney test for b and by the Kruskal-Wallis test followed by the Dunn's multiple comparisons test for post hoc analyses for c. (FIG. 4Q) A schematic representation of proposed molecular mechanisms: the inhibitory effects of $LTB_4$ are indicated. In panels e-g, i-k and m-p, data are presented as mean±SEM; n=5; ns, not significant, *P<0.05, P<0.01, *P<0.001, ****P<0.0001 compared with 100 nm $LTB_4$ in i or as indicated in the figure by the Kruskal-Wallis test followed by the Dunn's multiple comparisons test for post hoc analyses.

FIGS. 5A-5J: Notch and S1P signaling are required for reparative lymphangiogenesis and lymphedema resolution. (FIG. 5A) Tail-volume changes in lymphatic endothelial cell-specific-Notch1-deficient (LEC $Notch1^{-/-}$) mice subjected to lymphedema surgery on d24, treated with saline (n=7), or bestatin (n=7), compared with sham surgery controls (n=7). Data are presented in box-and-whiskers plots showing minimal to maximal values and all data points. Quantification of dermal skin thickness (FIG. 5B) and lymphatic dilation (FIG. 5C) of WT or LEC Notch1$^{-/-}$ mice in (FIG. 5A). (FIG. 5D) Relative whole tail gene transcripts of Vegfr3, Vegfc, Vegfd and Lyve1 of WT or LEC Notch1$^{-/-}$ mice in (FIG. 5A). (FIG. 5E) Relative whole tail gene transcripts of Hey1, EFNB2, Hes1, and Hes5 of WT or LEC Notch1$^{-/-}$ mice in (FIG. 5A). (FIG. 5F-5G) Representative immunofluorescent images of tail skin stained with EphrinB2 and Prox1 from WT (FIG. 5F) or LEC Notch1$^{-/-}$ (FIG. 5G) mice. DAPI stains nuclei; white arrows indicate co-staining; scale bar, 20 µm; n=5. (FIG. 5H) Tail-volume changes in lymphatic endothelial cell-specific-S1pr1-deficient (LEC S1pr1$^{-/-}$) mice subjected to lymphedema surgery on d24, treated with saline (n=6), or bestatin (n=6), compared with sham surgery controls (n=6). Data are presented in box-and-whiskers plots showing minimal to maximal values and all data points. Quantification of dermal skin thickness (FIG. 5I) and lymphatic dilation (FIG. 5J) of WT or LEC S1pr1$^{-/-}$ mice in (FIG. 5D). In panels FIG. 5A and FIG. 5H, mice expressing Prox1-Cre-ER were used as WTs, n=6 for sham surgery, n=8 for lymphedema surgery+saline, n=8 for lymphedema surgery+bestatin. In panels FIG. 5B-5E, FIG. 5I and FIG. 5J, data are presented as mean±SEM; n=5. ns, not significant, *P<0.05, P<0.01, *P<0.001, ****P<0.0001 by the Kruskal-Wallis test followed by the Dunn's multiple comparisons test for post hoc analyses.

FIG. 6A-6B; FIG. 6A is a table of patient demographics. FIG. 6B provides graphs showing serum concentrations of LTB$_4$ and PGE$_2$.

DETAILED DESCRIPTION OF THE EMBODIMENTS

Figure 1A:
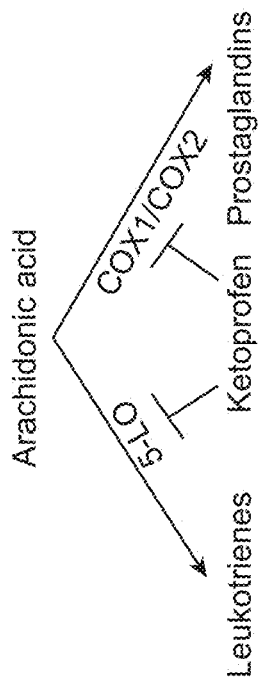

The lymphatic vascular system is crucial for the regulation of tissue fluid homeostasis, immune function, inflammatory response, and fat absorption and tissue disposition. Lymphatic dysfunction, either due to gene mutations, developmental disorders, or much more commonly secondary to damage to the lymphatic anatomy, can lead to lymphedema, a debilitating condition characterized by chronic tissue edema, impaired regional immunity, and regional accumulation of subcutaneous fat.

Physiological lymphangiogenesis is primarily a developmental process and occurs with lesser frequency in post-natal tissues. However, new lymphatic vessels form in post-natal tissues during ovarian oogenesis and wound healing. Therapeutic agents that can promote lymphangiogenesis (regenerative lymphatic repair) can reduce or prevent lymphedema.

However, many regulatory factors are shared between angiogenesis and lymphangiogenesis, such as vascular endothelial growth factor, VEGF-A, -B, -C, and -D. Developing selective therapies to promote lymphangiogenesis in the absence of effects on angiogenesis is desirable. In particular, there are no therapies currently approved and known to prevent lymphedema from occurring or, once it has occurred (stage 0 to 3), slow or stop its progression, much less reverse the incredibly debilitating and quality of life destroying manifestations in those patients with the most severe forms of established disease. The present invention provides methods and compositions that can be used to prevent and treat lymphedema and slow, stop, and even reverse its progression, and therefore represents a significant advance in the important goal of reducing the impact of this disease in patients and on our health care system.

Definitions

Acronyms. The following acronyms are used throughout the specification and defined as follows: 5-LO: 5-lipoxygenase; BEC: blood vascular endothelial cell; FLAP: 5-lipoxygenase activating protein; AA: arachidonic acid; BMPR2: bone morphogenetic protein receptor 2; BALF: bronchoalveolar lavage fluid; bFGF: basic fibroblast growth factor; BLTt: leukotriene B$_4$ receptor 1; BLT$_2$: leukotriene B4 receptor 2; CSL: transcriptional factor CBF1; COX: cyclooxygenase; CysLT: cysteinyl leukotriene; Dll4: delta-like 4; DAF-2DA: diaminofluorescein-2 diacetate; DMSO: dimethyl-sulfoxide; eNOS: endothelial nitric oxide synthase; LC-MS/MS: liquid chromatographic tandem mass spectrometric; LEC: lymphatic vascular endothelial cell; LTA$_4$: leukotriene A$_4$; LTA$_4$H: leukotriene A4 hydrolase; LTB$_4$: leukotriene B4; LTC$_4$: leukotriene C4; LTC4S: leukotriene C$_4$ synthase; LTD$_4$: leukotriene D$_4$; LTE$_4$: leukotriene E$_4$; LYVE-1: lymphatic vessel endothelial hyaluronan receptor; NICD: Notch intracellular domain; MAPK: mitogen-activated protein kinase; NO: nitric oxide; NOS: nitric oxide synthase; p5-LO: pSer271 5-LO; PGE2: prostaglandin E2; PGI$_2$: prostaglandin 1$_2$ (prostacyclin); SIP: sphingosine-1-phosphate; Sphkl: sphingosine kinase 1; VEGF: vascular endothelial growth factor; VEGFR2: vascular endothelial growth factor receptor 2; WT: wild-type.

"Active agent" and "therapeutic agent" means a compound, also referred to as a drug that exerts a preventive or therapeutic effect on a disease or disease condition. Active agent can refers not only to a single active agent but also to a combination of two or more different active agents.

"Alleviate" and "ameliorate" are equivalent to "treat" and refer to or mean a process by which the severity of a sign or symptom of a disorder is decreased. Importantly, a sign or symptom can be alleviated without being eliminated. Therapeutically effective dosages are expected to decrease the severity of, and so alleviate and ameliorate, a sign or symptom of disease.

"As-needed," in "as-needed administration," means that a formulation is administered to a patient when symptoms are observed, or when symptoms are expected to appear, or at any time that the patient and/or treating physician deems it appropriate to treat (therapeutically or prophylactically) undesirable symptoms (e.g., symptoms arising from a disease).

"Combination therapy" and "co-therapy" means the administration of a first active agent and at least a second, different active agent as part of a specific treatment regimen intended to provide the beneficial effect from the co-action of the at least two active agents. The beneficial effect of the combination may include, but is not limited to, pharmacokinetic or pharmacodynamic co-action resulting from the combination of therapeutic agents.

Administration of therapeutic agents in combination typically is carried out over a defined time period (usually minutes, hours, days or weeks depending upon the combination selected).

Combination therapy is not intended to encompass the administration of two or more different therapeutic agents as part of separate monotherapy regimens that incidentally and arbitrarily results in a combination therapy of the invention. Combination therapy includes administration of at least two different therapeutic agents in a sequential manner, wherein each therapeutic agent is administered at a different time, as well as administration of at least two different therapeutic agents in a substantially simultaneous manner.

Substantially simultaneous administration can be accomplished, for example, by administering to the subject a single capsule having a fixed ratio of each therapeutic agent or in separate capsules for each of the therapeutic agents. Sequential or substantially simultaneous administration of each therapeutic agent can be effected by any appropriate route, including, but not limited to, oral routes, intravenous routes, intramuscular routes, and direct absorption through mucous membrane tissues. The two different therapeutic agents can be administered by the same route or by different routes. For example, a first therapeutic agent of the combination selected may be administered by intravenous injection while the second therapeutic agent of the combination may be administered orally. Alternatively, for example, all therapeutic agents may be administered orally or all therapeutic agents may be administered by intravenous injection. The sequence in which the therapeutic agents are administered is not critical, unless otherwise stated. Combination therapy also includes the administration of the different therapeutic agents as described above in further combination with other biologically active ingredients and non-drug therapies (e.g., surgery or physical therapy). Where a combination therapy comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

"Compound" means a molecule and encompasses not only the specified molecular entity but, if the compound is an active agent or drug, also its pharmaceutically acceptable, pharmacologically active analogs, including, but not limited to, active metabolites, amides, conjugates, esters, hydrates, polymorphs, prodrugs, salts, solvates, and other such derivatives, analogs, including deuterated analogs and analogs containing radioactive atoms or other labeling moieties, and related compounds.

"Controlled release" refers to a drug-containing formulation or unit dose form thereof from which release of the drug is not immediate, i.e., with a controlled release formulation, administration does not result in immediate release of all of the drug administered into an absorption pool. The term is used interchangeably with "nonimmediate release" as defined in Remington: The Science and Practice of Pharmacy, Nineteenth Ed. (Easton, Pa.: Mack Publishing Company, 1995). In general, controlled release formulations include sustained release and delayed release formulations.

"Sustained release" and "extended release" means a drug formulation that provides for gradual release of a drug over an extended period of time, and typically, although not necessarily, results in substantially constant blood levels of a drug over an extended time period.

"Delayed release" refers to a drug formulation that, following administration to a patient, provides a measurable time delay before drug is released from the formulation into the patient's body.

"Dosage form" means any form of a pharmaceutical composition for administration to a subject (typically a human or animal of veterinary interest suffering from a disease or condition to be treated). "Dose" refers to an amount of active agent. "Unit dosage form" refers to a dosage form that contains a fixed amount of active agent. A single tablet or capsule is a unit dosage form. Multiple unit dosage forms can be administered to provide a therapeutically effective dose. A dosage form can include a combination of dosage forms.

"Effective amount" and "therapeutically effective amount" refers to a nontoxic but sufficient amount of an active agent to achieve a desired therapeutic effect.

Percentages and ratios used herein, unless otherwise indicated, are by weight.

"Pharmaceutically acceptable" means not biologically undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration.

"Pharmaceutically acceptable salts" mean derivatives of an active agent produced by making acid or base salts thereof. Examples of pharmaceutically acceptable salts include, but are not limited to, mineral or organic acid salts of basic residues such as amines, alkali or organic salts of acidic residues such as carboxylic acids, and the like. Pharmaceutically acceptable salts include the conventional non-toxic salts or the quaternary ammonium salts of the parent compound formed, for example, from non-toxic inorganic or organic acids.

Pharmaceutically acceptable salts include those formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Pharmaceutically acceptable salts include solvent addition forms (solvates) or crystal forms (polymorphs) as defined herein, of the same salt.

"Pharmacologically active" (or "active") as in a "pharmacologically active" derivative or analog, refers to a derivative or analog having the same type of pharmacological activity as the parent compound of approximately equivalent in degree.

"Preventing" and "prevent" means avoiding the onset of a clinically evident disease progression altogether or slowing the onset of a pre-clinically evident stage of a disease in individuals at risk. Prevention includes prophylactic treatment of those at risk of developing a disease.

"Sign" means an indication of disease and includes conditions that can be observed by a doctor, nurse, or other health care professional.

"Small molecule" as used herein refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". The small molecule can have a MW less than or equal to about 5 kDa. In other embodiments, the drug molecule has a MW less than or equal to about 1.5 kDa.

"Subject in need thereof refers to a human or other mammal suitable for treatment with an active agent. A subject in need thereof may have a disease or be at an increased risk, relative to the general population, of developing a disease.

"Symptom" means a sign or other indication of disease, illness, or injury. Symptoms may be felt or noticed by the individual experiencing them or by others, including by non-health-care professionals.

"Treating" and "treat" describes the management and care of a patient for the purpose of combating a disease, condition, or disorder and includes the administration of an active agent to alleviate the symptoms or complications of a disease, condition or disorder, or to eliminate the disease, condition or disorder.

Lymphedema, as used herein, is edema of a region or regions of the body due to lymphatic maldevelopment (primary lymphedema) or to obstruction, disruption or dysfunction (secondary or acquired lymphedema) of lymphatic vessels. Symptoms and signs may comprise varying degrees of brawny, fibrous, non-pitting edema in one or more regions of the body.

Primary lymphedemas are constitutional and relatively less common than the secondary forms. They vary in phenotype and patient age at presentation. The methods of the invention are applicable to these primary forms, although it will be understood by one of skill in the art that treatment may be more efficacious in some forms than others due to the differing disease etiologies. Primary forms of lymphedema include, without limitation Milroy's disease, Meige disease, (lymphedema praecox), lymphedema distichiasis, lymphedema tarda, etc., as well as other genetic syndromes having prominent lymphedema, such as Turner's syndrome and Hennekam syndrome.

For example, congenital lymphedema appears at birth or within months thereafter, and may be due to lymphatic aplasia or hypoplasia. Milroy's disease is an autosomal dominant familial form of congenital lymphedema attributed to flt4 gene mutations and associated with edema and, sometimes, diarrhea and/or hypoproteinemia due to a protein-losing enteropathy caused by intestinal lymphangiectasia. Lymphedema distichiasis is an autosomal dominant familial form of lymphedema praecox attributed to mutations in a transcription factor gene (FOXC2) and associated with extra eyelashes (distichiasis), and edema of legs, arms, and sometimes the face. Lymphedema tarda occurs after age 35. Both familial and sporadic forms exist; the genetic basis of both is unknown. Clinical findings are similar to those of lymphedema praecox but may be less severe. Hereditary lymphedema type II (Meige disease, lymphedema praecox) develops around puberty or shortly thereafter in most individuals. This is the most common type of primary lymphedema. In addition to lymphedema of the legs, other areas of the body such as the arms, face and larynx may be affected. Some individuals may develop yellow nails. Lymphedema is prominent in some other genetic syndromes, including Turner syndrome; yellow nail syndrome, characterized by pleural effusions, chronic lung disease, lymphedema and yellow nails; and Hennekam syndrome, a rare congenital syndrome of generalized lymphatic abnormality, facial anomalies, and intellectual disability. The methods and compositions of the invention may be used to treat any of these primary lymphedemas and their symptoms; in particular and without limitation, ubenimex administered as described herein may be used.

Secondary (acquired) lymphedema is far more common than primary. It is most commonly caused by surgery (especially lymph node dissection, typically for staging and treatment of cancers), radiation therapy (especially axillary or inguinal), trauma, lymphatic obstruction by a tumor, and, in developing countries, lymphatic filariasis. The methods and compositions of the invention may be used to treat any of these primary lymphedemas and their symptoms; in particular and without limitation, ubenimex administered as described herein may be used.

Ubenimex has been approved in Japan but not in Europe or the US for the treatment of cancer and has been reported to be a useful agent in the treatment of pulmonary arterial hypertension (PAH; see U.S. Pat. No. 9,233,089, incorporated herein by reference) but has not been approved for such use; those of skill in the art will appreciate upon contemplation of this disclosure that, while the ubenimex pharmaceutically acceptable salt(s) and dosage forms used to treat cancer in Japan or disclosed as useful in the treatment of PAH can be employed in the methods of the invention, such use is in patients suffering from lymphedema, who don't have PAH or a cancer for which ubenimex therapy is approved in the country of use. The methods and compositions of the invention are intended for the prevention and treatment of lymphedema.

In important embodiments, the invention will be practiced to treat patients with established secondary leukemia, typically contracted as a result of cancer therapy. It has been estimated that more than 15% of cancer survivors experience secondary lymphedema. Surgical removal of lymph nodes or therapeutic radiation of lymph nodes increases the risk of lymphedema. After axillary intervention, 15% to 30% of breast cancer survivors experience clinically relevant lymphedema, but other types of cancer and their associated treatments may cause secondary lymphedema as well. The incidences of lymphedema associated with other malignancies (cancers) were as follows: soft tissue sarcoma 30%, lower extremity melanoma 28%, gynecologic cancer 20%, genitourinary cancer 10%, and head and neck cancers 3%. Lymphedema may also result from increased lymph production in patients with chronic venous insufficiency, congestive heart failure, and other causes of venous hypertension. The methods of the invention are applicable to all such secondary lymphedema patients.

The cardinal sign of acquired lymphedema is soft-tissue edema, graded in 4 stages. The term "established lymphedema" may refer generically to any of stages 1-3 of the disease, including without limitation the more advanced stages of the disease, e.g. stage 2 and stage 3, where structural changes in affected tissue are observed. In stage 0, the affected region is physically normal, but lymphatic insufficiency can be demonstrated through clinical assessment. In stage 1, the edema is pitting, and the affected area often returns to normal after elevation of the affected limb (s). In stage 2, the edema is pitting, and chronic soft-tissue inflammation causes structural changes in the tissues that accompany the pitting edema. In stage 3, the edema is brawny and irreversible, largely because of chronic soft-tissue structural changes.

Treatment with the methods of the invention may be prophylactic, i.e., treatment commences before onset of stage 0 disease, usually (at least until greater clinical experience with the first approved drugs of this class are obtained) in cases where the individual is at risk of developing lymphedema due to medical procedures that confer such risk. Prophylactic treatment may also follow successful treatment of the disease: this is also referred to as "maintenance therapy" herein. Treatment itself is any administration of an LTB4 inhibitor as described herein, including but not limited to ubenimex therapy as described herein, and may commence at any time after the onset of stage 0 lymphedema, e.g. where treatment stabilizes or reverses patient condition to a non-symptomatic state. Treatment with the methods of the invention may commence following onset of stage 1 lymphedema. Treatment with the methods of the invention may commence following onset of stage 2 lymphedema. Treatment with the methods of the invention may commence following onset of stage 3 lymphedema.

The swelling that can accompany disease progression can be unilateral or bilateral, and may worsen when the weather is warm, before menstruation occurs, following physical exertion, and/or after the limb remains for a long time in a dependent position. It can affect any part of a limb (isolated proximal or distal) or the entire extremity, or the face, head and neck, trunk, breast or genitalia; it can restrict range of motion. Disability and emotional distress can be significant, especially when lymphedema results from medical or surgical treatment. Skin changes are common and include hyperkeratosis, hyperpigmentation, lichenification, verrucae, papillomas, and fungal infections. The methods of the invention include methods to treat any and all of these conditions and symptoms, including but not limited to by administration of ubenimex as described herein.

Lymphangitis or cellulitis may develop, for example, when bacteria traverse the skin barrier, which is abnormal in lymphedema. Lymphangitis is frequently streptococcal, causing erysipelas; sometimes it is staphylococcal. The affected limb becomes red and feels hot; red streaks may extend proximally from the point of entry, and lymphadenopathy may develop. Rarely, the skin breaks down. Rarely, long-standing lymphedema leads to lymphangiosarcoma (Stewart-Treves syndrome), usually in postmastectomy patients and in patients with filariasis. The methods of the invention include methods to treat any and all of these conditions and symptoms, including but not limited to by administration of ubenimex as described herein.

Without treatment, cellular overgrowth, adipose deposition and fibrosis promote the progressive anatomic distortion and loss of function of the affected areas. Additionally, impaired trafficking of antigen-presenting cells in lymph hampers local immune surveillance of the lymphedematous region(s) to the draining lymph nodes. Thus, there is chronic inflammation, infection, and hardening of the skin that, in turn, results in further lymph vessel damage and distortion of the shape of the affected body parts. Moreover, there is a high degree of dysfunction due to physical factors such as a decrease in joint mobility causing reduced amplitude of movements, increased leg weight, increased pain, and impaired ability to perform day-to-day tasks. The methods of the invention include methods to treat any and all of these conditions and symptoms, including but not limited to by administration of ubenimex as described herein.

Pathological skin changes associated with lymphedema include an increase in cellularity of layers of the skin, accumulation of glycoproteins, loss of elasticity, and subdermal increase in adipose layer. The methods of the invention include methods to treat any and all of these conditions and symptoms, including but not limited to by administration of ubenimex as described herein.

Those of skill will thus appreciate that the methods of the invention are applicable to the treatment and prevention of lymphedema including its signs and symptoms such as those associated with the following clinical indicia of lymphedema. A number of clinical indicia can be used to diagnose lymphedema and to monitor the effectiveness of therapy, including treatment with the compositions and methods of the present invention. The invention provides methods of determining efficacy of a lymphedema treatment in a subject in need thereof by (a) measuring an endpoint of a clinical indication in a patient, where the endpoint is measured after treatment has started, (b) comparing the endpoint of the clinical indication to a baseline or reference, where the baseline or reference is measured in the same subject or a similar subject population before treatment is begun, and (c) determining the efficacy of the lymphedema treatment based on the comparison step.

Analysis of clinical indicia may include measurement of dermal thickness; change of lymphedema volume of leg/arm/hand; change of stagnation of fluid at level of shoulder/trunk; change of extracellular fluid in arm; change of thickness and reflectivity of cutis and subcutis of arm/shoulder/trunk; change of elasticity of skin and subcutaneous tissue of arm; change of lymphatic architecture and function; change of venous circulation in arm/trunk; number of episodes of erysipelas.

When imaging is used to diagnose lymphedema or assess disease state or progression, the most common modality for diagnosis is indirect radionuclide lymphoscintigraphy. This procedure requires subcutaneous injection of an appropriate radiolabeled tracer, for example $^{99m}$Tc-antimony sulfide colloid or $^{99m}$Tc-labeled human serum albumin. Criteria for the diagnosis of lymphatic dysfunction include: (1) delayed, asymmetric or absent visualization of regional lymph nodes; (2) asymmetric visualization of lymphatic channels; (3) collateral lymphatic channels; (4) dermal backflow (5) interrupted vascular structures; and (6) visualization of the lymph nodes of the deep lymphatic system. The presence of "dermal back-flow" is considered abnormal. It is interpreted to represent the extravasation of lymph fluid from the lymphatics into the interstitium as a result of lymphatic and/or venous hypertension. Beyond lymphoscintigraphy, magnetic resonance imaging and computerized axial tomography have clinical utility. These imaging techniques permit objective documentation of the structural changes caused by lymphedema. Recent advances in the magnetic resonance approach have improved the visualization of lymphatic vascular anomalies in both nonenhanced and contrast-enhanced applications (see, for example, Pankaj et al. (2013) World J Surg Oncol. 2013; 11: 237). As an alternative, bioelectrical impedance has been used to detect and monitor upper limb lymphedema (see Ridner et al. (2009) Lymphat Res Biol. 7(1): 11-15), which uses characteristics of frequency-dependent current flow to quantify changes in extracellular fluid. In various embodiments, such technology is used to monitor the progress of therapy of a patient treated in accordance with the invention or to identify a patient that may benefit from such treatment.

The effectiveness of treatment by the methods of the invention will be evidenced by improvement in disease symptoms and pathology. Individuals being treated and medical practitioners may choose to evaluate success, monitor the course of treatment, adjust dosage and timing, etc. by any convenient indicia. It is anticipated that the invention will first find application in treatment of established lymphedema but as efficacy and safety are demonstrated in more and more patients, physicians will treat patients at earlier and earlier stages of the disease, with the safest agents, such as ubenimex is predicted to be, finding significant use, eventually, as a prophylaxis in most patients with a significant probability of developing lymphedema, with the acceptable probability for prophylactic treatment lowering as a drug is proved safe in more and more patients (i.e., the risks of therapy still are far outweighed by the benefits of preventing the disease even in patient populations at relatively low but still measurable risk of developing the disease).

In some embodiments of the invention, e.g., treatment of patients with established disease, improvements in the architecture of the skin provide a convenient method for assessing treatment success. For example, dermal thickness reflects the architectural changes in lymphedema. See, for example, Mellor et al., Breast J 2004; 10:496-503; Hacard et al. Skin Res Technol 2014; 20: 274-81, each herein specifically incorporated by reference. For example, dermal thickness may be measured with factory calibrated skinfold calipers, such as Lange skinfold calipers, Model EQ0014921. In some embodiments, a treatment provided herein is efficacious if, after a period of time from the onset of treatment (e.g., 2 weeks, 1 month, 2 months, 3 months, 4 months, 5 months, 6 months or longer), there is a decrease in dermal thickness of at least one affected region (e.g., limb) as compared to the dermal thickness of the at least one affected region prior to the onset of treatment. The decrease in dermal thickness observed with successful treatment may be a decrease of at least about 1 mm, at least about 2.5 mm, at least about 5 mm, at least about 7.5 mm, at least about 10 mm, and may be at least about 12.5 mm, at least about 15 mm, or more. Alternative measurements for determining a correction of pathologies of skin architecture may include, for example, dermal ultrasound, DEXA scanning, direct biopsy, visual inspection, etc. Dermal thickness and architecture, e.g. presence of hyperkeratosis, dermal collagen, and adipose deposition in an affected limb may be monitored.

In some embodiments, a change in the volume of the affected limb is measured as a measure of treatment success, i.e., the volume declines with successful treatment. Volume can be measured by any of a number of methods in the art, e.g. circumferential measurements, water displacement volumetry, etc. For example, an assessor may use a standardized tape measure for circumference measurements taken every 2-6 cm, and calculating the volume by, for example, the truncated cone method. Successful treatment may reduce, or decrease, the volume of lymphedematous body parts (both the fluid and tissue components). In some instances, volume is decreased 2-fold or more after treatment, i.e. as compared to the volume before treatment, for example, 2-fold or more, 3-fold or more, 4-fold or more, sometimes 5-fold or more, 10-fold or more, 15-fold or more, in some instances 20-fold or more, 50 fold- or more, etc. In other words, the volume is decreased by about 50 milliliters or more, 100 milliliters or more, 200 milliliters or more, 300 milliliters or more, 400 milliliters or more, 500 milliliters or more. In some instances, the volume is restored to normal volume, i.e. the volume prior to the onset of the lymphedema, e.g. the volume of the unaffected bilateral tissue.

Figure 6B:
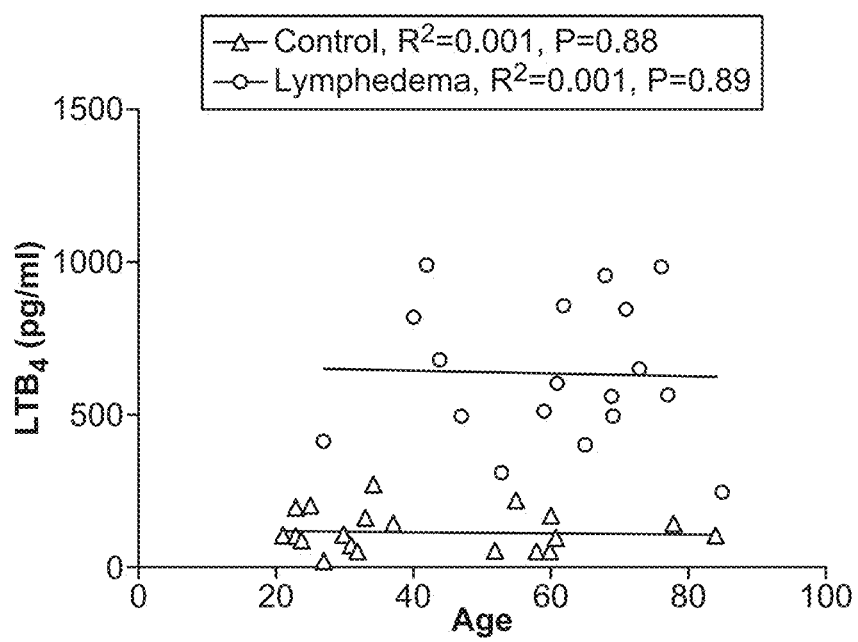
Figure 6B:
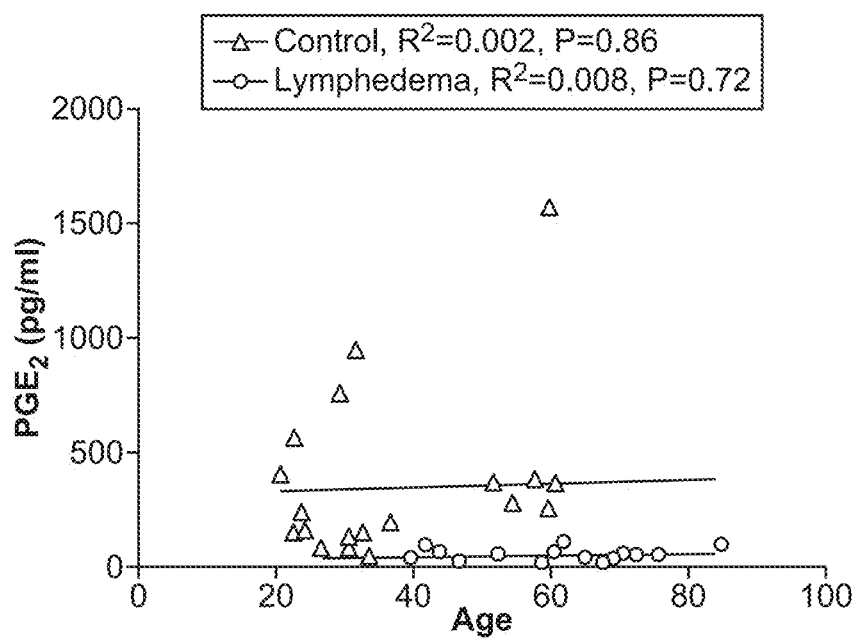

In some embodiments, the level of serum $LTB_4$ may be used for diagnosis, or selecting or stratifying patients for therapy, or for monitoring efficacy. A reference value of normal $LTB_4$ can be (depending on assay type and format and individual laboratory practices) up to 50 pg/mL or greater, up to 100 pg/mL or greater, up to 200 pg/mL or greater, up to about 250 pg/mL or greater, up to about 300 pg/mL. Individuals with lymphedema may have elevated baseline levels of serum $LTB_4$, for example as shown in FIG. 6, where the serum levels are up to about 1000 pg/ml or greater, and can range from about 500 pg/ml to about 1500 pg/ml. The treatment provided in the invention is efficacious if, after treatment has started, the endpoint $LTB_4$ level of the subject decreases from the baseline $LTB_4$ level. In other embodiments, the treatment provided in the invention is efficacious if, after treatment has started, the endpoint $LTB_4$ level is lower than the baseline $LTB_4$ level by 2-fold or more, 3-fold or more, 4-fold or more, 5-fold or more, 10-fold or more, 15-fold or more.

Patient Selection.

In another aspect, the present invention provides methods for selecting patients likely to benefit from the therapies of the invention, as well as methods for determining whether a patient is responding to such therapy. In some embodiments a patient is selected for treatment when a diagnosis of confirmed lymphedema is made, where the lymphedema may be stage 0, stage 1, stage 2 or stage 3. Diagnosis may be made on the basis of any of the clinical indicia described above.

In other embodiments, an individual at risk of developing lymphedema is treated prophylactically to prevent the development of lymphedema by the methods of the invention. In some such embodiments, the individual at risk of developing lymphedema has been treated for cancer. Such individuals can be stratified for risk of developing lymphedema by a medical professional. Cancers associated with a high degree of risk following treatment include, for example, breast cancer, soft tissue sarcoma, melanoma, ovarian cancer, prostate cancer, lymphoma, head and neck cancer. In some embodiments, the patient is not treated with ubenimex as a chemotherapeutic adjunct, e.g. a patient other than a leukemia patient in Japan or elsewhere, for example other than a patient in Japan or elsewhere receiving maintenance therapy of acute adult nonlymphocytic leukemia.

The present invention provides a variety of methods that enable the treating physician to treat patients individually, reflecting each patient's individual risk of developing lymphedema.

Thus, some patients, at low risk of developing lymphedema, may not be treated until symptoms manifest or persist for some period of time. Other patients, however, may be treated prophylactically, before symptoms appear or can be detected by clinicians (e.g. before Stage 0). These methods are further elaborated below.

Most individuals with lymphedema today and likely in the future will have it as a result of cancer therapy involving surgery and/or radiation that damages or destroys lymph nodes. For patients at a low risk of developing lymphedema associated with surgery, i.e., patients whose surgery involved only or less than about 4 lymph nodes with sentinel node technique, the treating physician may delay any treatment unless and until lymphedema symptoms manifest, i.e., the physician likely will not use the drug in a prophylactic mode in such patients unless and until safety and benefit has been demonstrated in greater numbers of patients. However, there is a much higher risk associated with nodal sampling of greater than 4 lymph nodes or with radiotherapy of lymph nodes, or both, so some patients receiving these procedures may well, in accordance with the invention, be treated in a prophylactic mode.

While actual patient data may need to be collected over years, it may well be that ubenimex therapy is sufficiently safe and efficacious that it will be routinely given as a prophylactic treatment to any person at sufficient risk of developing lymphedema. In the interim, the discussion below regarding timing of the initiation of the initiation of therapy is intended to provide non-limiting guidance to the physician as to how to use the drug safely until such actual experience is developed.

The risk of developing lymphedema, and timing of treatment, can be further stratified based on the treatment received by the individual. A low risk is associated with surgery only of less than about 4 lymph nodes with sentinel node technique. A much higher risk is associated with nodal sampling of greater than 4 lymph nodes; or with radiotherapy of lymph nodes, or both. Thus, in some embodiments a person having undergone nodal sampling of greater than 4 lymph nodes; or with radiotherapy of lymph nodes, or both is prophylactically treated with an effective dose of an LTB4 inhibitor according to the methods of the invention, or is treated after development of established lymphedema.

Where treatment is performed prophylactically after surgical treatment, initiation of treatment with an LTB4 inhibitor in accordance with the invention may be delayed for some period of time after surgery to ensure that the preventive treatment does not slow or delay wound healing. Treatment may commence immediately following surgical wound healing, or at a period of time following some or substantial surgical wound healing, e.g. after at least about 1 day, and more typically after about at least 3 days or more days, including about 1 week to 2 weeks, at which time wound healing is substantially complete in most patients, although again, prophylactic therapy may begin at any time prior to Stage 0, including after about 3 weeks post-surgery.

Where treatment is performed prophylactically in a patient treated without surgery, e.g. a patient treated with radiotherapy, chemotherapy, or a combination thereof, believed to put the patient at such risk for lymphedema that prophylactic therapy is required, the lymphedema prophylaxis may commence at any time during or following therapy, e.g. at the time of treatment, after about 1 day, about 3 days, about 1 week, about 2 weeks, about 3 weeks, or more. However, again, as such treatments are causing "wounds" requiring healing, the physician may defer the initiation of treatment precisely as described above to minimize any potential for the prophylactic therapy to interfere with wound healing.

Thus, as the animal model results provided herein demonstrate, reducing $LTB_4$ levels early in wound healing may delay that process. Accordingly, physicians desiring to use ubenimex or other $LTB_4$ inhibitor prophylactically to prevent lymphedema from developing may delay initiation of treatment until after wound-healing has begun (e.g., 1-3 days post-surgery) or even substantially completed (e.g., 7-14 days post-surgery) or, more practically, at any time prior to diagnosis of Stage 0 disease. Moreover, if the physician knows that the surgery is or may likely be followed by radiation therapy, particularly if that radiation therapy is to follow surgery closely in time or the surgery itself is not associated with a high risk of developing lymphedema, then treatment in accordance with the invention may be delayed until after radiation therapy has ceased (and wound healing has begun or is complete). As discussed, this is because the radiation damage is similar to a wound, and physicians may withhold prophylactic treatment as provided herein, at least in some patients, for a period of time sufficient for recovery from radiation damage to occur or at least get substantially underway (e.g. a few days to a few weeks after the last treatment, typically 1-2 weeks for full recovery).

While patients with established lymphedema can readily be diagnosed by visual means, and while cancer patients can be stratified regarding how likely they are to develop leukemia based on the treatments they receive, the invention provides other methods for diagnosing lymphedema and otherwise identifying patients likely to benefit from the treatment methods of the present invention.

As noted above, alternative methods of patient selection can utilize detection of elevated $LTB_4$ levels, e.g. in a cancer patient at risk of developing lymphedema. In these methods, a biological sample, which may be, for example and without limitation, a lymph, plasma, serum, blood, saliva, urine, etc. sample, and the level of $LTB_4$ in the sample is determined and compared to a control value. Individuals with elevated concentrations of $LTB_4$ relative to a normal control may be more likely to benefit from treatment by the methods of the invention. Depending on the application of the method, the control value may be determined from one or more normal individuals not suffering from lymphedema. The control value can also be determined from a sample previously obtained from the patient. Generally, higher (or elevated) levels of $LTB_4$ relative to a control value determined from a normal, non-diseased individual or population indicate that a subject may benefit from a preventive or therapeutic treatment method of the invention. Lower levels generally indicate that a patient is responding to therapy or, for a subject not on such therapy, that the therapeutic methods of the invention may not be as beneficial for that subject. In one embodiment, the methods of the invention include a step of obtaining a biological sample from a subject and determining the amount of $LTB_4$ in the sample prior to administering an effective dose of a leukotriene inhibitor.

For example, in some embodiments a higher or elevated level of $LTB_4$ in a blood sample, of at least 3-fold higher, at least 4-fold higher, at least 5-fold, at least about 10-fold higher, at least about 15-fold higher than the control value indicates that the patient is in need of treatment using a therapy of the invention or that the patient is likely to respond to a therapy of the invention. Standard methods for assessing $LTB_4$ levels are utilized. The method further comprises administering an effective amount of a $LTA_4H$ inhibitor of the invention to a patient determined to be likely to benefit from, in need of, or likely to respond to, a therapy of the invention, thereby treating or preventing lymphedema in the patient. It will be appreciated, however, that, at least initially after first regulatory approval, the vast majority of patients treated will have diagnosed lymphedema and so not need special assessment to be determined likely to benefit from treatment.

The development of secondary (acquired) lymphedema is associated with insufficient reparative lymphangiogenesis and lymphatic vessel remodeling. Lymphangiogenesis is a complex cellular process characterized by proliferation, migration, and differentiation of lymphatic endothelial cells. It is shown herein that LTB4 inhibits lymphangiogenesis. Therapeutic agents of interest for treatment of lymphedema include agents that inhibit the activity or synthesis of the leukotriene $LTB_4$. As shown herein, $LTB_4$ is correlated with development and maintenance of lymphedema. Its concentration in relevant biological samples, e.g. blood, plasma, lymph, etc. is increased during the development of lymphedema, and decreases in response to effective therapy. Without being limited by the theory, it is believed that $LTB_4$ induces lymphedema by multiple mechanisms that include inhibition of Notch signaling and sphingosine-1-phosphate signaling.

Therapies of the present invention may inhibit $LTB_4$ by inhibition of, for example, $LTA_4H$, which has an epoxide hydrolase activity that converts $LTA_4$ into $LTB_4$; by antagonizing an $LTB_4$ receptor, e.g. $LTB_4BLT1$ or $LTB_4BLT2$; by inhibiting 5-LO, or by inhibiting FLAP; by inhibiting both 5-LO and COX1/COX2. In some embodiments, an $LTB_4$ inhibitor does not exhibit dual inhibitory activity of both the 5-LO and COX1/COX2 pathways. In some embodiments, the LTB$_4$ inhibitor is not ketoprofen. In some embodiments, the LTB$_4$ inhibitor is ubenimex.

Therapeutic agents useful in the methods of the invention will also have the effect of partially or completely restoring the architecture of the tissue, i.e. skin, toward or to its condition pre-lymphedema. In other words, the architecture of the affected tissue will more closely resemble the architecture of normal, unaffected tissue, after treatment than before. Most notably, the dermis and subdermis return to a normal or more normal thickness, and inflammatory cell infiltrates and accumulated glycoproteins and collagen are reduced or absent. The architecture of the tissue may be assayed by any convenient means as described herein, e.g. skinfold thickness, biopsy, etc., if necessary or helpful to assess the efficacy of treatment or need to continue or alter therapy.

Therapeutic agents can serve as the active ingredient in pharmaceutical compositions formulated for the treatment of lymphedema, including a propensity for lymphedema. The compositions can also include various other agents to enhance delivery and efficacy. The compositions can also include various agents to enhance delivery and stability of the active ingredients.

In one embodiment, prevention or treatment of lymphedema in a subject is accomplished in accordance with the invention by administering a therapeutically effective amount of a leukotriene inhibitor compound that can inhibit LTA$_4$H, which results in decreased LTB$_4$ levels. Also, one can, in accordance with the invention, block binding of LTB$_4$ to BLT1 BLT2, which in turn results in decreased LTB$_4$ signaling, to treat lymphedema. Alternatively, one can, in accordance with the invention, block the activity of either or both 5-LO and/or FLAP, which in turn shuts down the conversion of AA to LTA$_4$, to treat lymphedema.

Methods Utilizing LTA4H Inhibitor

An LTA$_4$H inhibitor as referred to herein is a compound that inhibits an enzymatic function of LTA$_4$H, which enzymatic function includes both the aminopeptidase activity and the epoxide hydrolase activity. Preferably, the compound is a small molecule compound. LTA$_4$H inhibitors provided by the present invention to treat lymphedema include, without limitation, ubenimex (bestatin), (2S)-2-[[(2S,3R)-3-amino-2-hydroxy-4-phenylbutanoyl] amino]-4-methylpentanoic acid; SC57461A, LTA$_3$, SC22716, CTX4430, JNJ26993135, JNJ40929837, DG051, and analogs of any of the foregoing with LTA$_4$H inhibitory activity. See, for example, Shim and Paige (2012). Leukotriene A4 Hydrolase—An Evolving Therapeutic Target, Inflammatory Diseases—Immunopathology, Clinical and Pharmacological Bases, Dr Mahin Khatami (Ed.), ISBN: 978-953-307-911-0.

In various embodiments of the invention, ubenimex, including but not limited to ubenimex in the Bestatin 10 mg or 30 mg unit dosage forms that are commercially available, is administered to a patient with lymphedema. Alternative unit dosage forms may be formulated, e.g. about 50 mg unit dose, about 60 mg unit dose, about 70 mg unit dose, about 75 mg unit dose, about 80 mg unit dose, about 90 mg unit dose, about 100 mg unit dose, and may be up to about 125 mg unit dose, up to about 150 mg unit dose, up to about 175 mg unit dose, up to about 200 mg unit dose, up to about 250 mg unit dose. In some embodiments the patient has acquired lymphedema. In some such embodiments, the lymphedema has developed following radiation and/or surgery of cancer, e.g. breast cancer, sarcoma, melanoma, lymphoma, ovarian cancer, prostate cancer, etc.

In some embodiments, oral doses of ubenimex generally in the range of 10 mg to 180 mg per day re administered to a subject in need thereof to improve functioning and outcome in the prevention or treatment of lymphedema. In one embodiment, the daily dose is 10 mg. In another embodiment, the daily dose is 60 mg. In another embodiment, the daily dose is 90 mg. In another embodiment, the daily dose is 120 mg. In another embodiment, the daily dose is 180 mg. Thus, depending on the patient, the daily dose can be, for example and without limitation, 10 mg, 30 mg, 40 mg, 50 mg, 60 mg, 80 mg, 90 mg, 100 mg, 120 mg, 130 mg, 150 mg, and 180 mg. Unit dose forms with each of these amounts of ubenimex are provided by the invention; alternatively, a Bestatin unit dose form can also be used. In other embodiments, the daily dose is higher, up to 500 mg or more, e.g., such therapies may include, e.g. daily doses of 450 mg administered TID in 150 mg doses or daily doses of 500 mg administered BID in 250 mg doses.

The therapeutically effective dose of a LTA$_4$H inhibitor, including without limitation ubenimex or analog of ubenimex, or pharmaceutically acceptable salt thereof, thus can more generally be about 10-1500 mg/day, about 10-1000 mg/day, about 10-500 mg/day, about 50-500 mg/day, about 100-500 mg/day, or, in other embodiments, about 200-500 mg/day. A LTA$_4$H inhibitor (e.g., ubenimex or analog or ubenimex) or pharmaceutically acceptable salt thereof, can be administered to a subject at about 20 to 500 mg twice or three times a day, about 20-400 mg twice or three times a day, about 20-300 mg twice or three times a day, about 20-250 mg twice or three times a day, about 20-200 mg twice or three times a day, about 20-180 mg twice or three times a day, about 50-180 mg twice or three times a day. For example, a LTA$_4$H inhibitor (e.g., ubenimex or an analog or ubenimex) or pharmaceutically acceptable salt thereof, is administered at about 100-200 mg twice or three times a day.

Oral doses of ubenimex generally in the range of 10 mg to 500 mg per day are administered to a subject in need thereof in accordance with one embodiment of the invention to improve functioning and outcome in the prevention and treatment of lymphedema. In one embodiment, the daily dose is 10 mg. In another embodiment, the daily dose is 60 mg. In another embodiment, the daily dose is 90 mg. In another embodiment, the daily dose is 120 mg. In another embodiment, the daily dose is 180 mg. In another embodiment, the daily dose is less than 500 mg. Thus, depending on the patient, the daily dose can be, for example and without limitation, 10 mg, 30 mg, 40 mg, 50 mg, 60 mg, 80 mg, 90 mg, 100 mg, 120 mg, 130 mg, 150 mg, 180 mg, 200 mg, 225 mg, 250 mg, 275 mg, 300 mg, 325 mg, 350 mg, 375 mg, 400 mg, 425 mg, 450 mg, 475 mg, 500 mg or more. Unit dose forms with each of these amounts of ubenimex are provided by the invention; alternatively, a commercially available Bestatin unit dose form (marketed by Nippon Kayaku) can also be used. Generally continuous (or near continuous) daily dosing, administered once daily, twice daily, three time daily, every 6 hours, every 4 hours, and the like will be continued until treatment appears to no longer have a beneficial effect or until unacceptable side effects appear. Many patients will take the medication as prescribed in accordance with the invention for at least a week, at least a month, at least 2 months, at least 3 months, at least 4 months, at least 6 months, and at least a year or longer. Many patients will take the medication as prescribed in accordance with the invention for the rest of their lives. Preferably, the subject in need thereof is a human.

While a daily dose in the range provided above can be conveniently administered QD (daily), the present invention provides methods and unit dose forms suitable for other dosing schedules. For example and without limitation, BID (twice a day) and TID (three times a day) administration can also be used to achieve a beneficial therapeutic effect. In some embodiments, the ubenimex dose administered is 60 mg BID, 80 mg BID, 100 mg BID, 125 mg BID, 150 mg BID, 175 mg BID, 200 mg BID; 250 mg BID; or 60 mg TID, 80 mg TID, 100 mg TID, 125 mg TID, 150 mg TID, 175 mg TID, 200 mg TID.

Ubenimex analogs useful in the methods and pharmaceutical compositions of the invention include LTA$_4$H inhibitor compounds described in U.S. Pat. Nos. 4,185,156; 4,189,604; 4,370,318; and 4,474,764, each of which is incorporated herein by reference.

An LTA$_4$H inhibitor provided by the present invention to treat lymphedema is JNJ26993135, I-[4-(benzothiazol-2-yloxy)-benzyl]-piperidine-4-carboxylic acid. Oral doses of JNJ26993135 generally in the range of 50 mg to 500 mg per day are administered to a subject in need thereof in accordance with one embodiment of the invention to improve functioning and outcome in the treatment of lymphedema. In one embodiment, the daily dose is 50 mg. In another embodiment, the daily dose is 150 mg. In another embodiment, the daily dose is 300 mg. In another embodiment, the daily dose is 500 mg. Thus, depending on the patient, the daily dose can be, for example and without limitation, 50 mg, 60 mg, 100 mg, 120 mg, 150 mg, 240 mg, 300 mg, 400 mg, and 500 mg. Unit dose forms with each of these amounts of JNJ26993135 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject in need thereof is a human. While a daily dose in the range provided above can be conveniently administered QD, the present invention provides methods and unit dose forms suitable for other dosing schedules. For example and without limitation, BID and TID administration can also be used to achieve a beneficial therapeutic effect.

JNJ26993135 analogs useful in the methods and pharmaceutical compositions of the invention include the LTA$_4$H inhibitor compounds described in US Patent Application Publication Nos. 20080194630A1; 20050043379A1 and 20050043378A1, each of which is incorporated herein by reference.

An LTA$_4$H inhibitor provided by the present invention to treat lymphedema is JNJ40929837. Oral doses of JNJ40929837 generally in the range of 10 mg to 500 mg per day are administered to a subject in need thereof in accordance with one embodiment of the invention to improve functioning and outcome in the treatment of lymphedema. In one embodiment, the daily dose is 50 mg. In another embodiment, the daily dose is 100 mg. Thus, depending on the patient, the daily dose can be, for example and without limitation, 10 mg, 20 mg, 30 mg, 40 mg, 50 mg, 60 mg, 70 mg, 80 mg, 100 mg, 150 mg, 200 mg, or 500 mg. Unit dose forms with each of these amounts of JNJ40929837 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject in need thereof is a human. While a daily dose in the range provided above can be conveniently administered QD, the present invention provides methods and unit dose forms suitable for other dosing schedules. For example and without limitation, BID and TID administration can also be used to achieve a beneficial therapeutic effect.

An LTA$_4$H inhibitor provided by the present invention to treat lymphedema is DG051, 4-[(2S)-2-{[4-(4-chlorophenoxy)phenoxy]methyl}-1-pyrrolidinyl]butanoic acid. Oral doses of DG051 generally in the range of 50 mg to 300 mg per day are administered to a subject in need thereof in accordance with one embodiment of the invention to improve functioning and outcome in the treatment of lymphedema. In one embodiment, the daily dose is 50 mg. In another embodiment, the daily dose is 150 mg. In another embodiment, the daily dose is 300 mg. Thus, depending on the patient, DG051 can be administered, for example and without limitation, 50 mg, 100 mg, 150 mg, 200 mg, 250 mg and 300 mg per day. Unit dose forms with each of these amounts of DG051 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject in need thereof is a human. While a daily dose in the range provided above can be conveniently administered QD, the present invention provides methods and unit dose forms suitable for other dosing schedules. For example and without limitation, BID and TID administration can also be used to achieve a beneficial therapeutic effect.

DG051 analogs useful in the methods and pharmaceutical compositions of the invention include the LTA$_4$H inhibitor compounds described in U.S. Pat. No. 7,402,684; J Med Chem. 2010 Jan. 28; 53(2):573-85; Bio-org Med Chem Lett. 2009 Nov. 15; 19(22):6275-9, each of which is incorporated herein by reference.

An LTA$_4$H inhibitor provided by the present invention to treat lymphedema is CTX-4430, also named EP-501, or an analog or pharmaceutically acceptable salt thereof (see Khim et al., 2008, Bioorg. & Med. Chem. Ltrs. 18:3895-3898, the contents of which are incorporated herein by reference). The drug is a highly potent, orally bioavailable LTA$_4$H Inhibitor with the human dose projected to be less than 100 mg once daily. Oral doses of CTX-4430 generally in the range of 10 mg to 100 mg per day are administered to the subject in need thereof in accordance with one embodiment of the invention to improve functioning and outcome in the treatment of lymphedema. In one embodiment, the daily dose is 10 mg. In another embodiment, the daily dose is 50 mg. In another embodiment, the daily dose is 100 mg. Thus, depending on the patient, the daily dose can be, for example and without limitation, 10 mg, 20 mg, 30 mg, 40 mg, 50 mg, 60 mg, 70 mg, 80 mg, 90 mg and 100 mg. Unit dose forms with each of these amounts of CTX-4430 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. Preferably, the subject is a human.

B. Methods Utilizing BLT1/BLT2 Antagonist.

In one embodiment of the invention, the BLT1/BLT2 antagonist employed to treat lymphedema is LY293111, 2-[2-propyl-3-[3-[2-ethyl-4-(4-fluorophenyl)-5-hydroxyphenoxy]-propoxy]phenoxy]benzoic acid. LY293111 is a competitive BLT1 antagonist resulting in selective inhibition of the LTB$_4$ pathway.

In humans, oral doses of LY293111 generally in the range of 50 mg to 2000 mg per day are administered in accordance with one embodiment of the invention to improve functioning and outcome in the treatment of lymphedema. In one embodiment, the daily dose is 50 mg. In another embodiment, the daily dose is 500 mg. In another embodiment, the daily dose is 1000 mg. In another embodiment, the daily dose is 1500 mg. In another embodiment, the daily dose is 2000 mg. Thus, depending on the patient, the daily dose can be, for example and without limitation, 50 mg, 100 mg, 200 mg, 300 mg, 400 mg, 500 mg, 600 mg, 700 mg, 800 mg, 900 mg, 1000 mg, 1200 mg, 1500 mg, 1600 mg, 1700 mg, 1800 mg and 2000 mg. Unit dose forms with each of these amounts of LY293111 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered QD, the present invention provides methods and unit dose forms suitable for other dosing schedules. For example and without limitation, BID and TID administration can also be used to achieve a beneficial therapeutic effect.

LY293111 analogs useful in the methods and pharmaceutical compositions of the invention include the BLT1/BLT2 antagonist compounds described in Proceedings of the American Society for Clinical Oncology (2002) 21; 1(ABs 343) (LY293111 for Cancer); SCRIP World Pharmaceutical News 1997, 2272 (13), U.S. Pat. No. 6,235,785, and US Patent Application Publication Nos. 20020013370 and 20020010213, each of which is incorporated herein by reference.

In one embodiment of the invention, the BLT1/BLT2 antagonist is ONO4057, 5-[2-(2-carboxyethyl)-3-[6-(4-methoxyphenyl)-5E-hexenyl]oxyphenoxy]valeric acid. In humans, oral doses of ONO4057 generally in the range of 50 mg to 600 mg per day are administered in accordance with one embodiment of the invention to improve functioning and outcome in the treatment of lymphedema. In one embodiment, the daily dose is 50 mg. In another embodiment, the daily dose is 100 mg. In another embodiment, the daily dose is 300 mg. In another embodiment, the daily dose is 600 mg. Thus, depending on the patient, the daily dose can be, for example and without limitation, 50 mg, 60 mg, 70 mg, 80 mg, 90 mg, 100 mg, 150 mg, 200 mg, 250 mg, 300 mg, 400 mg, 500 mg, and 600 mg. Unit dose forms with each of these amounts of ONO4057 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered QD, the present invention provides methods and unit dose forms suitable for other dosing schedules. For example and without limitation, BID and TID administration can also be used to achieve a beneficial therapeutic effect.

ONO4057 analogs useful in the methods and pharmaceutical compositions of the invention include the BLT1/BLT2 antagonist compounds described in European Patent Application Publication No. 405116A, incorporated herein by reference.

In one embodiment of the invention, the BLT1/BLT2 antagonist is CP195543, (+)-2-(3-benzyl-4-hydroxy-chroman-7-yl)-4-trifluoromethyl-benzoic acid. In humans, oral doses of CP195543 generally in the range of 20 mg to 200 mg per day are administered in accordance with one embodiment of the invention to improve functioning and outcome in the treatment of lymphedema. In one embodiment, CP195543 is administered in doses of 5 mg four times per day. In another embodiment, CP195543 is administered 25 mg four times per day. In another embodiment, CP195543 is administered 50 mg four times per day. Thus, depending on the patient, CP195543 can be administered, for example and without limitation, 5 mg, 10 mg, 15 mg, 20 mg, 25 mg, 30 mg, 35 mg, 40 mg, 45 mg, and 50 mg four times per day. Unit dose forms with each of these amounts of CP195543 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered four times per day, the present invention provides methods and unit dose forms suitable for other dosing schedules. For example and without limitation, QD, BID, and TID administration can also be used to achieve a beneficial therapeutic effect.

CP195543 analogs useful in the methods and pharmaceutical compositions of the invention include the BLT1/BLT2 antagonist compounds described in PCT Patent Application Publication No. WO9811085, Journal of Pharmacology and Experimental Therapy, 1998, 285: 945-54, each of which is incorporated herein by reference.

In one embodiment of the invention, the BLT1/BLT2 antagonist employed to treat lymphedema is CGS25019C, 4-(5-(4-(aminoiminomethyl)phenoxy)pentoxy)-3-methoxy-N,N-bis(1-methylethyl) 2-butanedioate. In humans, oral doses of CGS25019C generally in the range of 60 mg to 600 mg per day are administered in accordance with one embodiment of the invention to improve functioning and outcome in the treatment of lymphedema. In one embodiment, the daily dose is 60 mg. In another embodiment, the daily dose is 300 mg. In another embodiment, the daily dose is 600 mg. Thus, depending on the patient, CGS25019C can be administered, for example and without limitation, 60 mg, 120 mg, 180 mg, 240 mg, 300 mg, 360 mg, 420 mg, 480 mg, 540 mg and 600 mg per day. Unit dose forms with each of these amounts of CGS25019C are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered QD, the present invention provides methods and unit dose forms suitable for other dosing schedules. For example and without limitation, BID and TID administration can also be used to achieve a beneficial therapeutic effect.

CGS25019C analogs useful in the methods and pharmaceutical compositions of the invention include the BLT1/BLT2 antagonist compounds described in ACS Meeting 1994, 207th; San Diego (MEDI003); International Congress of the Inflammation Research Association 1994; White Haven(Abs W23), each of which is incorporated herein by reference.

In one embodiment of the invention, the BLT1/BLT2 antagonist employed to treat lymphedema is Biomed 101, 7-[3-(4-acetyl-3-methoxy-2-propylphenoxy)propoxy]-3,4-dihydro-8-propyl-2H-1-benzopyran-2-carboxylic acid. In humans, oral doses of Biomed 101 generally in the range of 25 mg to 300 mg three times per day (TID) are administered in accordance with one embodiment of the invention to improve functioning and outcome in the treatment of lymphedema. In one embodiment, the daily dose is 25 mg three times per day. In another embodiment, the daily dose is 150 mg three times per day. In another embodiment, the daily dose is 300 mg three times per day. Thus, depending on the patient, Biomed 101 can be administered, for example and without limitation, 25 mg, 50 mg, 75 mg, 100 mg, 125 mg, 150 mg, 175 mg, 200 mg, 225 mg, 250 mg and 300 mg three times per day. Unit dose forms with each of these amounts of Biomed 101 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered TID, the present invention provides methods and unit dose forms suitable for other dosing schedules. For example and without limitation, QD and BID administration can also be used to achieve a beneficial therapeutic effect.

Biomed 101 analogs useful in the methods and pharmaceutical compositions of the invention include the BLT1/BLT2 antagonist compounds described in U.S. Pat. Nos. 5,532,383; 5,516,917; 5,439,937; 5,310,951; 5,124,350, PCT Patent Application Publication No. WO1995006702 and European Patent Application Publication No. 0593478, each of which is incorporated herein by reference.

In one embodiment of the invention, the BLT1/BLT2 antagonist employed to treat lymphedema is BIIL284BS, ethane; ethyl(NE)-N-[[4-[[3-[[4-[2-(4-hydroxyphenyl)propan-2-yl]phenoxy]methyl]phenyl]methoxy]anilino]methylidene]carbamate. In humans, oral doses of BIIL284BS generally in the range of 5 mg to 75 mg per day are administered in accordance with one embodiment of the invention to improve functioning and outcome in the treatment of lymphedema. In one embodiment, the daily dose is 5 mg. In another embodiment, the daily dose is 25 mg per day. In another embodiment, the daily dose is 75 mg per day. Thus, depending on the patient, BIIL284BS can be administered, for example and without limitation, 5 mg, 10 mg, 15 mg, 20 mg, 25 mg, 30 mg, 35 mg, 40 mg, 50 mg, 60 mg, 70 mg and 75 mg per day. Unit dose forms with each of these amounts of BIIL284BS are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered QD, the present invention provides methods and unit dose forms suitable for other dosing schedules. For example and without limitation, BID and TID administration can also be used to achieve a beneficial therapeutic effect.

BIIL284BS analogs useful in the methods and pharmaceutical compositions of the invention include the compounds with BLT1/BLT2 antagonist activity described in U.S. Pat. No. 6,576,669, incorporated herein by reference.

C. Methods Utilizing 5-LO/FLAP Inhibitors

A 5-LO inhibitor refers to any member of the class of small molecules that block the dioxygenation function of 5-lipoxygenase.

Thus, in various embodiments of the invention, the 5-LO inhibitor employed to treat lymphedema is zileuton (trade name ZYFLO), 1-[1-(1-benzothiophen-2-yl)ethyl]-1-hydroxyurea. In humans, oral doses of zileuton generally in the range of 300 mg to 1200 mg two times per day (BID) are administered in accordance with one embodiment of the invention to improve functioning and outcome in the treatment lymphedema. In one embodiment, the daily dose is 300 mg BID. In another embodiment, the daily dose is 600 mg BID. In another embodiment, the daily dose is 1200 mg BID. Thus, depending on the patient, zileuton can be administered, for example and without limitation, 300 mg, 600 mg, 900 mg and 1200 mg BID. Unit dose forms with each of these amounts of zileuton are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered BID, the present invention provides methods and unit dose forms suitable for other dosing schedules. For example and without limitation, QD and TID administration can also be used to achieve a beneficial therapeutic effect.

Zileuton analogs useful in the methods and pharmaceutical compositions of the invention include the compounds with 5-LO inhibitory activity described in U.S. Pat. Nos. 7,371,874; 7,368,575; 6,077,850; 6,034,256; 6,028,072; 6,020,347; 5,935,990; 5,886,015; 5,783,586; 5,776,932; 5,714,488; 5,688,822; 5,665,749; 5,635,514; 5,532,382; 5,514,703; 5,512,581; 5,403,939; 5,356,921; 5,292,900; 5,266,705; 5,229,516; 4,873,259; 4,822,809; PCT Patent Application Nos. 1999067208; 1999026923; 1999025685; 1997012866; 1996038418; 1996038442; 1996036617; 1996003388; 1995002507; 199534552; 1995026346; 1995024192; and 1995002574; European Patent Nos. 0557787; 0888307; 0828718; 0772594; 0772606; and 0765318, each of which is incorporated herein by reference.

In one embodiment of the invention, the 5-LO/FLAP inhibitor employed to treat lymphedema is MK0633, 4-(4-Fluorophenyl)-7-[[[5-[(1 S)-1-hydroxy-1-(trifluoromethyl)propyl]-1,3,4-oxadiazol-2-yl]amino]methyl]-2H-1-benzopyran-2-one. In humans, oral doses of MK0633 generally in the range of 10 mg to 100 mg per day are administered in accordance with one embodiment of the invention to improve functioning and outcome in the treatment of lymphedema. In one embodiment, the daily dose is 10 mg. In another embodiment, the daily dose is 50 mg per day. In another embodiment, the daily dose is 100 mg per day. Thus, depending on the patient, MK0633 can be administered, for example and without limitation, 10 mg, 20 mg, 30 mg, 40 mg, 50 mg, 60 mg, 70 mg, 80 mg, 90 mg, and 100 mg per day. Unit dose forms with each of these amounts of MK0633 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered QD, the present invention provides methods and unit dose forms suitable for other dosing schedules. For example and without limitation, BID and TID administration can also be used to achieve a beneficial therapeutic effect.

MK0633 analogs useful in the methods and pharmaceutical compositions of the invention include the compounds with 5-LO/FLAP inhibitory activity described in PCT Patent Application Publication No. WO1998003484; U.S. Pat. Nos. 5,861,419; 6,001,843; 6,040,450; 6,040,319; 6,071,936; 6,127,545; 6,204,387; 6,252,116 and 6,369,275; and Bioorg Med Chem. 2012 Jun. 15; 20(12):3728-41, each of which is incorporated herein by reference.

In one embodiment of the invention, the 5-LO inhibitor employed to treat lymphedema is ZD2138, 6-((3-Fluoro-5-(4-methoxy-3,4,5,6-tetrahydro-2H-pyran-4-yl)phenoxy) methyl)-1-methylquinol-2-one. In humans, oral doses of ZD2138 generally in the range of 25 mg to 400 mg per day are administered in accordance with one embodiment of the invention to improve functioning and outcome in the treatment of lymphedema. In one embodiment, the daily dose is 25 mg. In another embodiment, the daily dose is 200 mg per day. In another embodiment, the daily dose is 400 mg per day. Thus, depending on the patient, ZD2138 can be administered, for example and without limitation, 25 mg, 50 mg, 100 mg, 150 mg, 200 mg, 250 mg, 300 mg, 350 mg, and 400 mg per day. Unit dose forms with each of these amounts of ZD2138 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered QD, the present invention provides methods and unit dose forms suitable for other dosing schedules. For example and without limitation, BID and TID administration can also be used to achieve a beneficial therapeutic effect.

ZD2138 analogs useful in the methods and pharmaceutical compositions of the invention include compounds with 5-LO inhibitory described in U.S. Pat. Nos. 5,401,751; 5,236,919 and 5,134,148; and European Patent No 466452, each of which is incorporated herein by reference.

In one embodiment of the invention, the 5-LO inhibitor employed to treat lymphedema is VIA2291, 1-[(2R)-4-[5-[(4-fluorophenyl)methyl]thiophen-2-yl]but-3-yn-2-yl]-1-hydroxyurea. VIA29911, also named Atreleuton or ABT761. In humans, oral doses of VIA2291 generally in the range of 25 mg to 200 mg per day are administered in accordance with one embodiment of the invention to improve functioning and outcome in the treatment of lymphedema. In one embodiment, the daily dose is 25 mg. In another embodiment, the daily dose is 100 mg per day. In another embodiment, the daily dose is 200 mg per day. Thus, depending on the patient, VIA2291 can be administered, for example and without limitation, 25 mg, 50 mg, 75 mg, 100 mg, 125 mg, 150 mg, 175 mg and 200 mg per day. Unit dose forms with each of these amounts of VIA2291 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives.

While a daily dose in the range provided above can be conveniently administered QD, the present invention provides methods and unit dose forms suitable for other dosing schedules. For example and without limitation, BID and TID administration can also be used to achieve a beneficial therapeutic effect.

VIA2291 analogs useful in the methods and pharmaceutical compositions of the invention include the compounds with 5-LO inhibitory activity described in U.S. Pat. Nos. 7,544,684; 7,470,687; 7,135,471; 5,616,596; 5,516,789; 5,288,751 and 5,288,743, each of which is incorporated herein by reference.

D. Methods Utilizing FLAP Inhibitors

A FLAP inhibitor refers to any compound of the class of small molecules that inhibit the binding of FLAP to AA.

In one embodiment of the invention, the FLAP inhibitor employed to treat lymphedema is DG031, (R)-2-[4-(quinolin-2-yl-methoxy)phenyl]-2-cyclopentyl acetic acid. DG031, formerly named BAY X1005 or Veliflapon. In humans, oral doses of DG031 generally in the range of 100 mg to 750 mg per day are administered in accordance with one embodiment of the invention to improve functioning and outcome in the treatment of lymphedema. In one embodiment, the daily dose is 100 mg. In another embodiment, the daily dose is 500 mg. In another embodiment, the daily dose is 750 mg. Thus, depending on the patient, DG031 can be administered, for example and without limitation, 100 mg, 150 mg, 200 mg, 250 mg, 300 mg, 350 mg, 400 mg, 450 mg, 500 mg, 550 mg, 600 mg, 650 mg, 700 mg and 750 mg per day. Unit dose forms with each of these amounts of DG031 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered QD, the present invention provides methods and unit dose forms suitable for other dosing schedules. For example and without limitation, BID and TID administration can also be used to achieve a beneficial therapeutic effect.

DG031 analogs useful in the methods and pharmaceutical compositions of the invention include the compounds with FLAP inhibitor activity described in U.S. Pat. Nos. 5,473,076; 5,306,820 and 4,970,215; European Patent No. 344519; and German Patent No. 19880531, each of which is incorporated herein by reference.

In various embodiments of the invention, the FLAP inhibitor employed to treat lymphedema is MK886, 3-[3-butylsulfanyl-1-[(4-chlorophenyl)methyl]-5-propan-2-yl-indol-2-yl]-2,2-dimethyl-propanoic acid. MK886, also named as L663536, In humans, oral doses of MK886 generally in the range of 100 mg to 750 mg per day are administered in accordance with one embodiment of the invention to improve functioning and outcome in the treatment of lymphedema. In one embodiment, the daily dose is 100 mg. In another embodiment, the daily dose is 250 mg. In another embodiment, the daily dose is 750 mg. Thus, depending on the patient, MK886 can be administered, for example and without limitation, 100 mg, 150 mg, 200 mg, 250 mg, 300 mg, 350 mg, 400 mg, 450 mg, 500 mg, 550 mg, 600 mg, 700 mg and 750 mg per day. Unit dose forms with each of these amounts of MK886 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered QD, the present invention provides methods and unit dose forms suitable for other dosing schedules. For example and without limitation, BID and TID administration can also be used to achieve a beneficial therapeutic effect.

MK886 analogs useful in the methods and pharmaceutical compositions of the invention include the compounds with FLAP inhibitor activity described in U.S. Pat. Nos. 7,629,467 and 5,081,138; US Patent Application Publication Nos. 20110003815; 20100298343; 201000190761; 20100168076; 20100152185; 20090258885; 20090197883; and 20060211677; and European Patent No. 419049, each of which is incorporated herein by reference.

In one embodiment of the invention, the FLAP inhibitor employed to treat lymphedema is MK591, 3-[3-tert-butyl-sulfanyl-1-[(4-chlorophenyl)methyl]-5-(quinolin-2-yl-methoxy)indol-2-yl]-2,2-dimethylpropanoate. In humans, oral doses of MK591 generally in the range of 12.5 mg to 100 mg two times per day are administered in accordance with one embodiment of the invention to improve functioning and outcome in the treatment of lymphedema. In one embodiment, the daily dose is 12.5 mg BID. In another embodiment, the daily dose is 50 mg BID. In another embodiment, the daily dose is 100 mg BID. Thus, depending on the patient, MK591 can be administered, for example and without limitation, 12.5 mg, 25 mg, 37.5 mg, 50 mg, 62.5 mg, 75 mg, 87.5 mg, and 100 mg BID. Unit dose forms with each of these amounts of MK591 are provided by the invention. Generally continuous (or near continuous) daily dosing will be continued until treatment appears to no longer have a beneficial effect or until unacceptable side effects appear. Many patients will take the medication for at least a week, at least a month, and at least a year or longer. Many patients will take the medication for the rest of their lives. While a daily dose in the range provided above can be conveniently administered BID, the present invention provides methods and unit dose forms suitable for other dosing schedules. For example and without limitation, QD and TID administration can also be used to achieve a beneficial therapeutic effect.

MK591 analogs useful in the methods and pharmaceutical compositions of the invention include the compounds described in European Patent Application No. 419049; U.S. Pat. Nos. 7,563,790; 7,470,687; 7,312,328; 7,141,572; 7,135,471; 7,129,241; 5,459,150; 5,380,850; 5,272,145; 5,254,521; 5,254,567; 5,204,344; and PCT Patent Application Publication Nos. 1994013293A2; 1993010115A1, each of which is incorporated herein by reference.

Any compound of the above classes of compounds (sections A-D above) can be formulated as provided herein for use in the methods of the invention. In addition to active agents, such therapeutic compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose water, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The therapeutic compositions, also referred to herein as pharmaceutical compositions, can be administered for prophylactic and/or therapeutic treatments as described herein. For previously untested compositions, toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, and intrathecal methods.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations suitable for enteral administration, such as, for example, administration topically (e.g., as solutions, lotions, creams, paste, emulsions, suspensions, etc.), orally, rectally, vaginally, or by inhalation, include capsules, liquid solutions, emulsions, suspensions, and elixirs. For example, if prepared for topical applications, the compositions may comprise a biocompatible organic solvent, e.g. an isopropyl ester such as isopropyl myristate and isopropyl palmitate; a polar lipid, e.g. lecithin, phosphatidylcholine, etc., a surfactant, e.g. docusate sodium, docusate sodium benzoate, docusate calcium, tween 80, polysorbate 80; water; and/or urea (present at a concentration of about 5 to 20% by mass of the final composition). In some instances, a topical formulation will comprise an enhancer for skin penetration, such as SEPA 09. Examples of topical formulations may be found in, e.g. U.S. Pat. Nos. 5,654,337, 5,093,133, 5,210,099, 3,957, 971, 5,016,652, the complete disclosures of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The therapeutic methods of the invention may be combined with one or more additional therapies for the treatment of lymphedema. Prior to the present invention, few pharmacologic therapies have been found to be effective in the treatment of lymphedema. Case reports have suggested, however, that chronic lymphedematous changes (eg, elephantiasis nostra verrucosa [ENV]) can be treated with oral and topical retinoids. These therapies are thought to help normalize keratinization and decrease inflammatory and fibrotic changes.

Topical emollients and keratolytics, such as ammonium lactate, urea, and salicylic acid, have been recommended to improve secondary epidermal changes.

Patients experiencing recurrent lymphangitis or cellulitis may require long-term, prophylactic treatment with antimicrobial agents such as penicillin, cephalexin, or erythromycin.

Filariasis has been treated with the anthelmintic agents diethylcarbamazine and albendazole.

Mobilizing fluid may utilize elevation and compression, exercise, massage, pressure bandages, intermittent pneumatic compression, drainage of lymphatics, complex decongestive therapy, and the like. Surgical soft-tissue reduction, lymphatic reanastomoses, and formation of drainage channels may also be included in a therapeutic program.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Leukotriene $B_4$ Interference with Sphigosine-1-phosphate and Notch Signaling after Lymphatic Injury Contributes to the Pathogenesis of Lymphedema Lymphedema is a significant global health problem with no effective pharmacological therapies. Of note, recent investigations suggest a central role for inflammation in this disease. Here, we used a murine model of acquired lymphedema to define the contribution of specific immunity in the evolution of lymphatic insufficiency and to address how inflammation causes disease. We found that in lymphedematous states, increases in leukotriene B4 (LTB4), acting through its G-protein-coupled receptor (BLT1), blocked lymphangiogenesis through the attenuation of sphingosine-1-phosphate (S1P) and Notch signaling. Therapeutic targeting of either LTB4 biosynthesis or LTB4 signaling through BLT1 reversed structural tissue changes and improved lymphatic function. This study demonstrates LTB4 as a therapeutic target for diseases characterized by lymphatic vascular insufficiency.

Figure 4A:
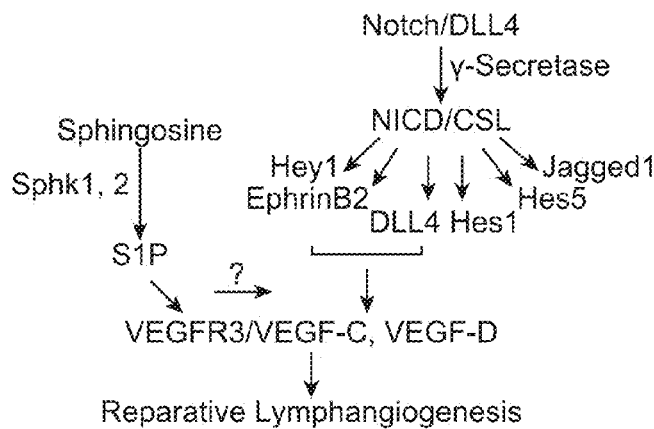
FIG. 4A-4Q: $LTB_4$ blocks in vitro lymphangiogenesis by inhibiting S1P and Notch signaling.

Ketoprofen, a nonsteroidal anti-inflammatory drug (NSAID), reversed murine experimental lymphedema. Ketoprofen is an inhibitor of cyclooxygenase (COX), and also inhibits 5-lipoxygenase (5-LO). This dual inhibitory property suggests that the efficacy of ketoprofen in experimental lymphedema might be mediated by its capacity to inhibit either or both of these pathways of arachidonic acid metabolism (FIG. 4a).

5-LO oxygenates arachidonic acid to yield an unstable intermediate, $LTA_4$. $LTA_4$ is quickly converted by $LTA_4$ hydrolase ($LTA_4H$) to $LTB_4$ or, alternatively by $LTC_4$ synthase ($LTC_4S$) to the cysteinyl LTs (CysLTs): $LTC_4$, $LTD_4$, and $LTE_{411}$. The signaling mediators responsible for the favorable impact of ketoprofen in lymphedema have not been identified. In this context, S1P and Notch1 are two promising candidate pathways that have been strongly implicated in reparative lymphangiogenesis. The purpose of this study was to investigate the mechanism of action of ketoprofen in experimental lymphedema. Here, we used a murine model of acquired lymphedema, induced by ablation of the major lymphatic conduits in the tail. This model, with its cutaneous inflammatory changes, closely simulates the biological characteristics of acquired human lymphedema.

Figure 1B:
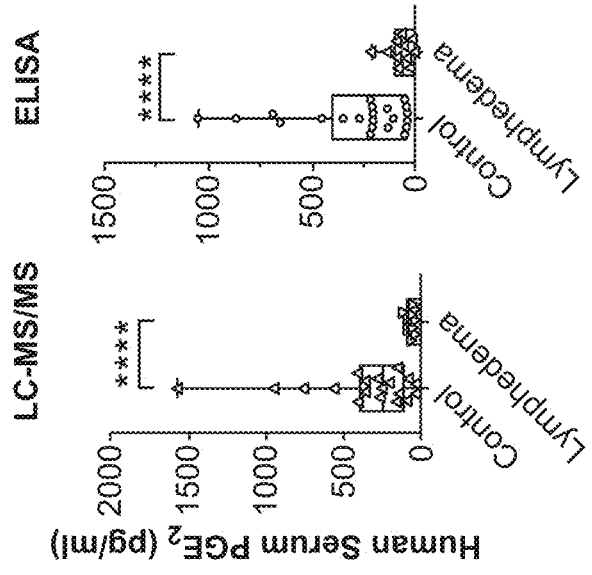
Figure 1C:
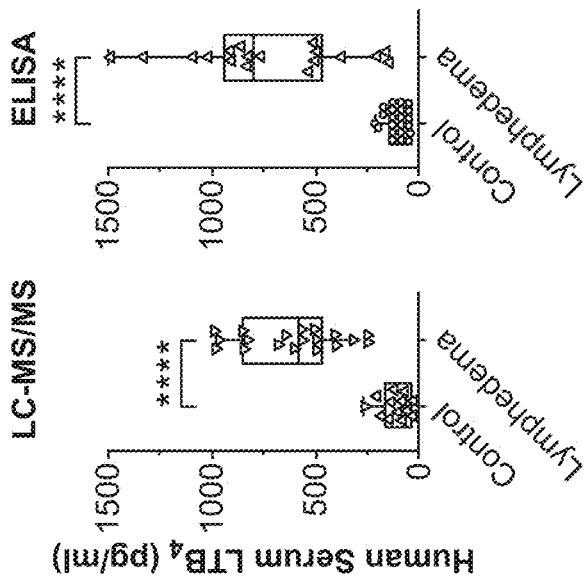

5-LO/LTB4 signaling is increased in human and mouse lymphedema. Given our recent discovery that the 5-LO metabolite, $LTB_4$, causes blood vascular endothelial cell (BEC) apoptosis, and informed by the knowledge that the COX1/COX2 metabolite prostaglandin E2 (PGE2) actually promotes lymphangiogenesis, we hypothesized that the beneficial effect of ketoprofen might be due to suppression of $LTB_4$ synthesis (FIG. 1a). Circulating $LTB_4$ levels were significantly elevated in lymphedema patients compared to healthy controls, whereas PGE2 was decreased in clinical disease (FIG. 1b,c; FIG. 6, Table 1). We examined lymphedematous mice for evidence of 5-LO activation. The murine model of acquired lymphedema is induced by microsurgical ablation of the major lymphatic conduits in the tail. Elevated $LTB_4$ signaling in lymphedema was measured in neutrophils, macrophages and blood endothelial cells, for example by immunofluorescent images of human skin samples stained with 5-LO, or assays of $LTB_4$ concentration increase during lymphedema development as determined by ELISA. mRNA transcripts of the cognate $LTB_4$ receptors, BLT1, BLT2 (Ltb4r1, Ltb4r2), were increased during the development of lymphedema; while those of the $PGE_2$ receptors, EP1, EP2 (Etger1, Etger2), were stable, as measured by qRT-PCR. Notably, the control levels of $LTB_4$ in human serum ranged were not more than about 250 pg/ml, when measured by either MS/MS or ELISA, while the serum from lymphedematous patients showed elevated levels of from 500 to over 1000 pg/ml.

Figure 1D:
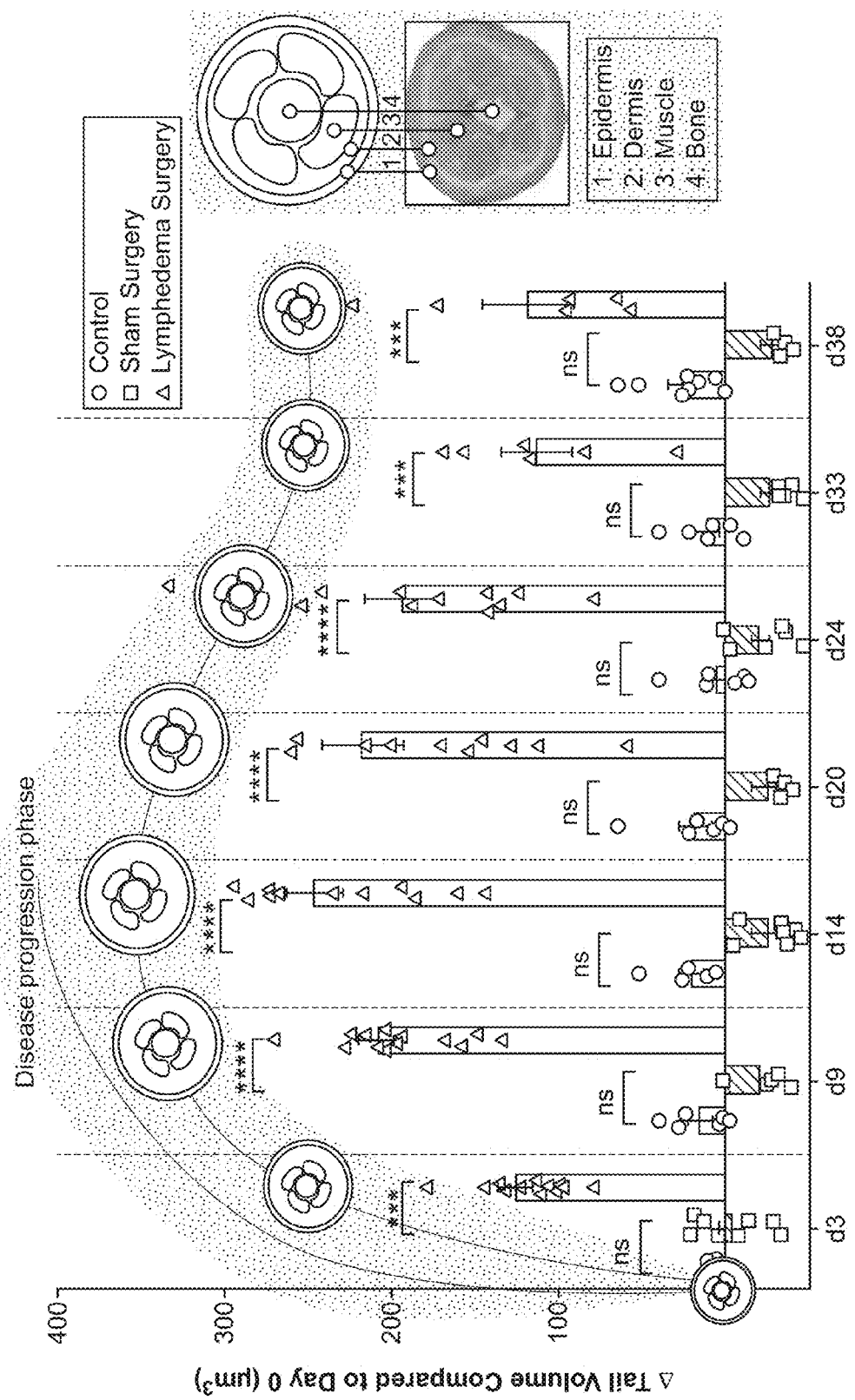
Figures 1I, 1J:
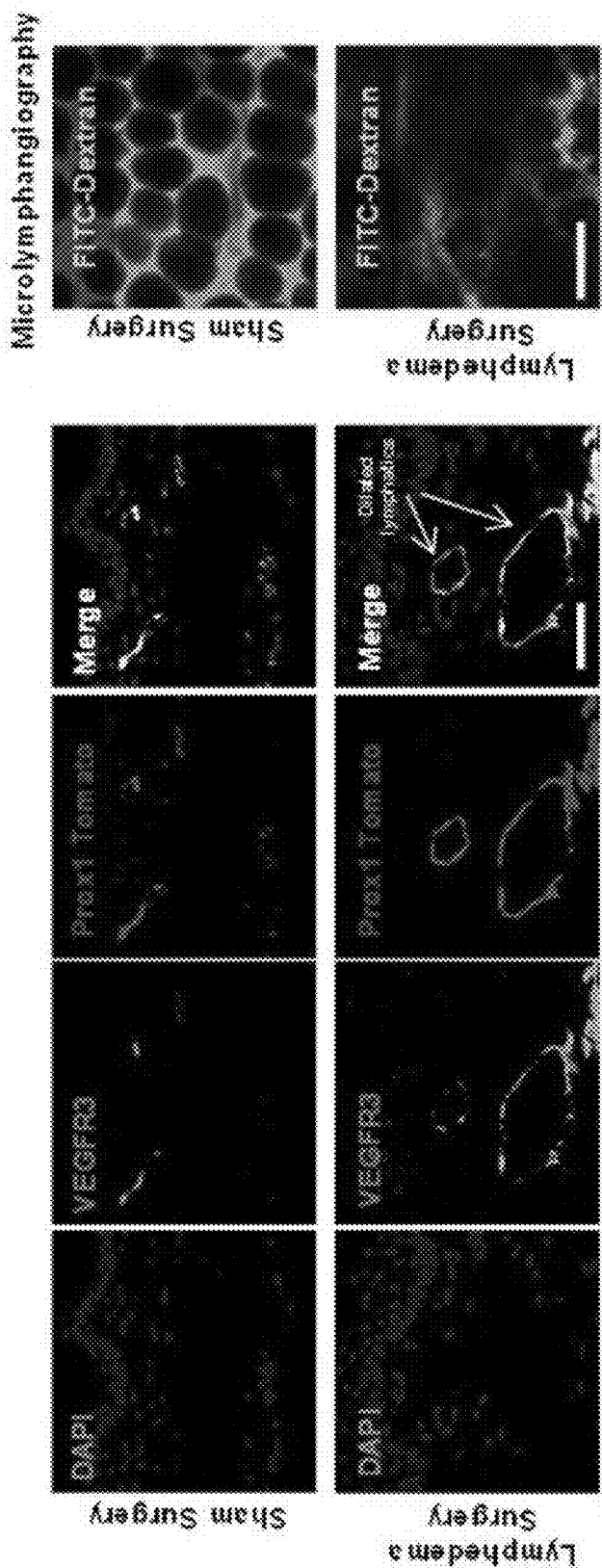

Following lymphatic ablation, tail edema progresses, peaks at d14 and partially resolves through cutaneous healing (FIG. 1d-f). In lymphedema, 5-LO was expressed in lymphedematous skin in myeloperoxidase$^+$ (MPO$^+$) neutrophils, CD68$^+$ macrophages and blood vessels. Enhanced $LTB_4$ and reduced PGE2 biosynthesis were documented in these mice with dilated lymphatics and abnormal lymph flow, in association with increased transcription of the cognate $LTB_4$ receptor BLT1, BLT2 (Ltb4r1, Ltb4r2) but stable PGE2 receptor expression (FIG. 1g-j; and Supplemental data not shown). Prox1-Cre-ER-tdTomato reporter mice demonstrated increased lymphatic endothelial $LTA_4H$ and decreased COX2 and mPGES-1 tissue expression, suggesting that dilated lymphatics, like inflammatory and blood vascular cells, produce LTB4 in disease (Supplemental data not shown). Cumulatively, these findings demonstrate that abrogation of $LTB_4$ explains the efficacy of ketoprofen in lymphedema.

Blocking Late, but not Early, $LTB_4$ Signaling Ameliorates Experimental Lymphedema.

To further investigate whether reduced $LTB_4$ synthesis underlies the mechanism of action of ketoprofen in the treatment of lymphedema, we compared the efficacy of ketoprofen, ibuprofen (inhibitor of COX1/COX2 only), zileuton (5-LO inhibitor), bestatin ($LTA_4H$ inhibitor), Ly293111 (BLT1 antagonist), montelukast (antagonist of CysLTs) and shRNA specifically targeting Ltb4r1 (FIG. 2a). Ketoprofen, zileuton and bestatin therapies, initiated on d3, each effectively reduced serum $LTB_4$ levels as assessed on d24; shLtb4r1 lentivirus efficiently decreased Ltb4r1 tissue levels (Supplemental data not shown). Tail swelling was significantly reduced in $LTB_4$-targeted groups, but not in the ibuprofen and montelukast groups; the therapeutic benefit was associated with resolution of disease-related dermal thickening and a conserved epidermal/dermal junction (FIG. 2b-j and Supplemental data not shown). By contrast, ibuprofen treatment resulted in unresolved edema, irregular epidermal/dermal junction and a 2- to 3-fold expansion of the subdermal tissue between cartilage and dermis. Blocking $LTB_4$ biosynthesis diminished tissue edema, increased expression of lymphangiogenic genes and improved lymphatic function (Supplemental data not shown).

To assess whether more established disease could be reversed using this approach, two delayed bestatin-dosing regimens were tested, with therapy initiated 9d or 14d post-surgically; both delayed therapies were effective (Supplemental data not shown). To determine whether congenital absence of Alox5 or Ltb4r1 would attenuate lymphedema, we examined Alox5$^{-/-}$ and Ltb4r1$^{-/-}$ mice. Unexpectedly, both of these experimental groups developed tail edema and skin necrosis after both lymphatic ablation and sham surgery. Here, the pathology did not exhibit characteristics of lymphedema but, rather, showed heightened inflammation, ischemia, and tissue necrosis, consistent with poor wound repair (FIG. 2k,l and Supplemental data not shown). Notably, prior studies found that $LTB_4$ was required for neutrophil recruitment in response to sterile skin wounding and that blocking $LTB_4$ with bestatin resulted in significantly larger skin lesions on day 1 post-wounding.

We evaluated the changes in expression of 168 angiogenesis- and inflammation-related genes pertinent to wound healing in Alox5$^{-/-}$ mice after sham or lymphedema surgery and noted significant down regulation of key angiogenic genes in association with up-regulation of inflammatory mediators (Supplemental data not shown). To further verify that $LTB_4$ signaling is important for wound healing in this early post-operative period, local shLtb4r1 lentiviral injection, bestatin, and Ly293111 therapies were administered prior to sham and lymphedema surgery. With this dosing schedule, $LTB_4$ antagonism was not beneficial, but instead we observed limited normal angiogenic responses while increasing inflammatory gene transcripts (FIG. 2m-r and Supplemental data not shown). Collectively, these data confirmed that $LTB_4$ signaling is important early in surgical wound repair but subsequently plays a distinct, critical role in the later evolution of lymphedema (Supplemental data not shown).

$LTB_4$ Blocks In Vitro Lymphangiogenesis in a BLT1-Dependent Manner.

The development of secondary lymphedema is associated with insufficient reparative lymphangiogenesis and lymphatic remodeling. To investigate whether $LTB_4$ affects lymphangiogenesis in vitro, we cultured human LECs (HLECs) with a physiologically relevant concentration of $LTB_4$ and examined the ability of HLECs to form capillary-like network structures on Matrigel. Administration of VEGF-C, a promoter of lymphangiogenesis, served as a positive control. In HLECs, $LTB_4$ decreased tube area, while blocking BLT1 with the antagonist U75302 or shRNA normalized tube formation (FIG. 3a and Supplemental data not shown). $LTB_4$ inhibited HLEC migration, preventing them from forming sprouts in the 3D-fibrin-gel assay. Antagonizing BLT1 permitted HLECs to migrate normally and exhibit regular sprout-like structures (FIG. 3b-d). The quantification of these assays is summarized in FIG. 3e-h. LTB4 blocked lymphangiogenesis in a concentration-dependent manner (FIG. 3 i-l and Supplemental data not shown). Because $LTB_4$ causes BEC death, we assessed $LTB_4$-mediated HLEC apoptosis. $LTB_4$ induced LEC apoptosis in a concentration-dependent manner (Supplemental data not shown).

These results demonstrate that $LTB_4$ inhibits HLEC in vitro lymphangiogenic activity by blocking the migration, differentiation, and sprouting of these cells and by directly inducing apoptosis. Matrigel plug assays were performed to investigate whether $LTB_4$ has in vivo anti-lymphangiogenic activity. Immunofluorescent staining of LEC markers LYVE1 and VEGFR3 revealed that $LTB_4$ attenuated lymphatic vessel formation and inhibited the VEGFR3 expression of HLECs in vivo, whereas blocking $LTB_4$ signaling restored lymphatic vessel growth (Supplemental data not shown).

$LTB_4$ Blocks In Vitro Lymphangiogenesis by Inhibiting S1P and Notch Signaling.

Figure 4B:
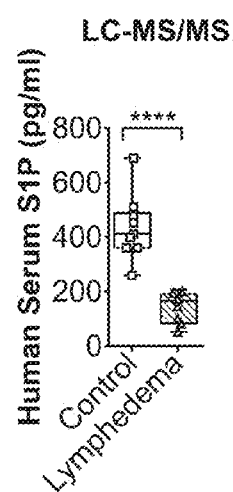
Figure 4C:
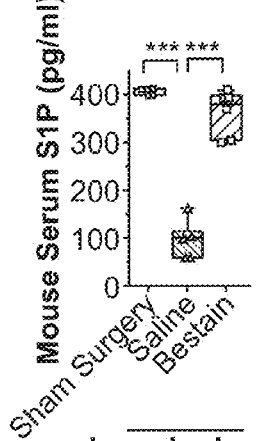
Figure 4D:
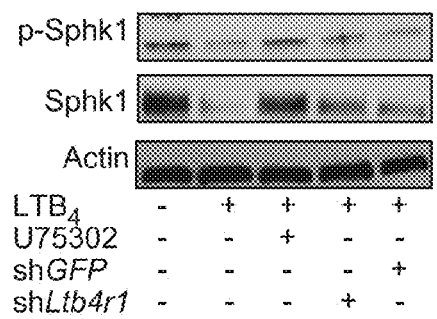
(FIG. 4D) Western blot analysis detecting p-SphK1 and total SphK1 in HLECs treated with 400 nM $LTB_4$, 10 µM U75302+$LTB_4$ or shLtb4r1 expressing lentivirus+$LTB_4$. n=3.
Figure 4E:
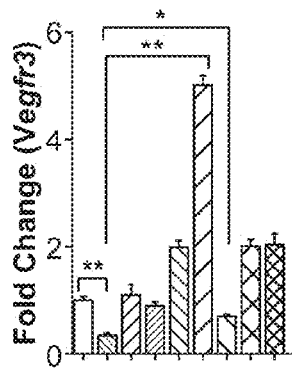
(FIG. 4E-4G) qRT-PCR analysis measured the relative transcription of Vegfr3 (FIG. 4E), Vegfc (FIG. 4F) and Vegfd (FIG. 4G) in HLECs following the treatment of $LTB_4$, U75302+$LTB_4$, shLtb4r1+$LTB_4$, $LTB_4$+100 ng/ml S1P, 100 ng/ml S1P, shS1pr1 expressing lentivirus+S1P, shDll4 expressing lentivirus+S1P or 25 µM DAPT+S1P.
Figure 4F:
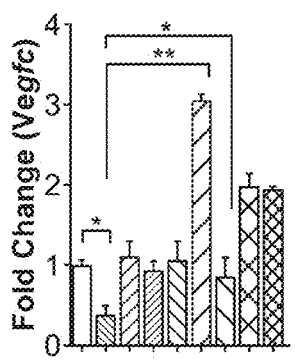
Figure 4G:
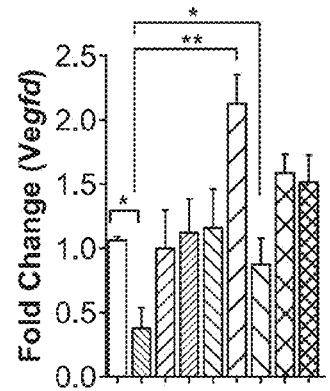

Because the inhibitory effects of $LTB_4$ on lymphangiogenesis have not previously been described, we next investigated pathways putatively altered by this lipid mediator. S1P was evaluated because it is pro-lymphangiogenic and critical for normal embryonic lymphatic patterning, and because its vasoprotective properties are inhibited by $LTB_4$. Given the requirement for Notch signaling in lymphatic development and reparative lymphangiogenesis after postnatal injury, as well as emerging results described below, we also investigated the possibility that $LTB_4$ impairs lymphangiogenesis through inhibition of Notch signaling pathways (FIG. 4a). Circulating S1P was significantly decreased in human and mouse lymphedema (FIG. 4b,c). Cutaneous expression of Sphk1 and eNOS (another enzyme helping to maintain functional lymphatic integrity in concert with S1P28,29) was reduced in the lymphatics after surgery, in association with increased S1pr1; bestatin therapy initiated 3d after surgery restored S1P and S1pr1 levels and normalized Sphk1 and eNOS expression in mice (Supplemental data not shown). HLECs cultured with exogenous $LTB_4$ showed diminished p-Sphk1 which was restored by blockade of BLT1 (FIG. 4d). These data provide evidence for aberrant S1P signaling in lymphedema and that S1P signaling can be normalized by antagonizing $LTB_4$.

Figure 4H:
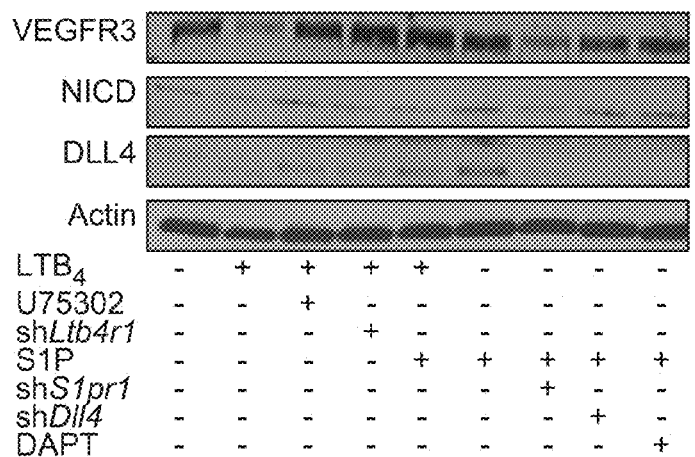
(FIG. 4H) Western blot detecting VEGFR3, DLL4, NICD in HLECs under the same treatments as e, f, g. n=3.

Next, the effect of $LTB_4$ on the levels of lymphangiogenic factors was assessed. $LTB_4$ treatment of HLECs reduced VEGFR3 expression and Vegfc, Vegfd transcription. By contrast, exogenous S1P increased the expression of these factors and partially normalized their down modulation induced by $LTB_4$. Silencing S1pr1 inhibited Vegfr3, Vegfc and Vegfd, but not to the same extent as $LTB_4$, suggesting that $LTB_4$ also inhibited lymphangiogenesis through S1P-independent pathways (FIG. 4e-h; Supplemental data not shown). For this reason, we elected to also investigate the impact of a high $LTB_4$ milieu on Notch signaling in LECs. The effects of Notch signaling on VEGFs in HLECs were assessed by co-culturing cells with shDll4 and DAPT, both of which inhibited Vegfr3, Vegfc, Vegfd transcription, an effect normalized by S1P (FIG. 4e-h; Supplemental data not shown). S1P increased levels of cleaved Notch (NICD) and DLL4 in HLECs and reversed the inhibition of shDll4 and DAPT. By contrast, $LTB_4$ and shS1pr1 decreased NICD and DLL4 expression, suggesting that S1P promotes, while $LTB_4$ blocks, Notch activation (FIG. 4h; Supplemental data not shown).

Figure 4I:
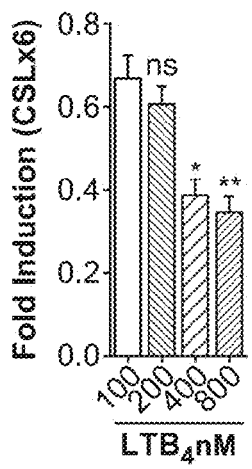
(FIG. 4I) Luciferase activity of HLECs co-transfected with Notch reporter plasmid pG13-11-CSL and pRL-SV40. HLECs were treated with 100 nm, 200 nm, 400 nm or 800 nm $LTB_4$ for 24 h before measurements.
Figure 4J:
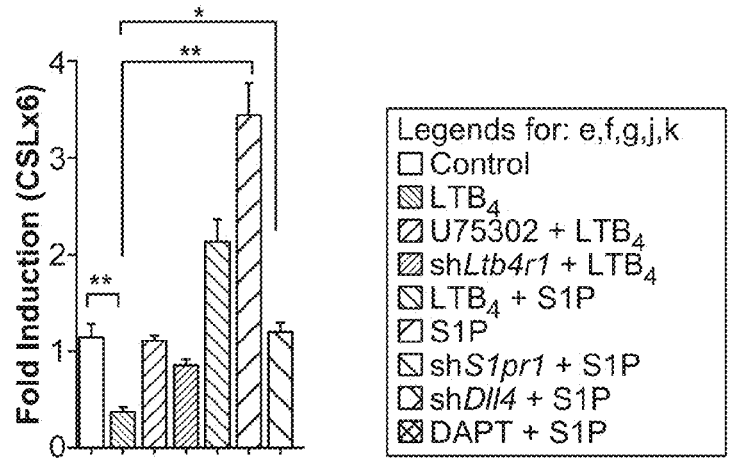
(FIG. 4J) CSL reporter assay.
Figure 4K:
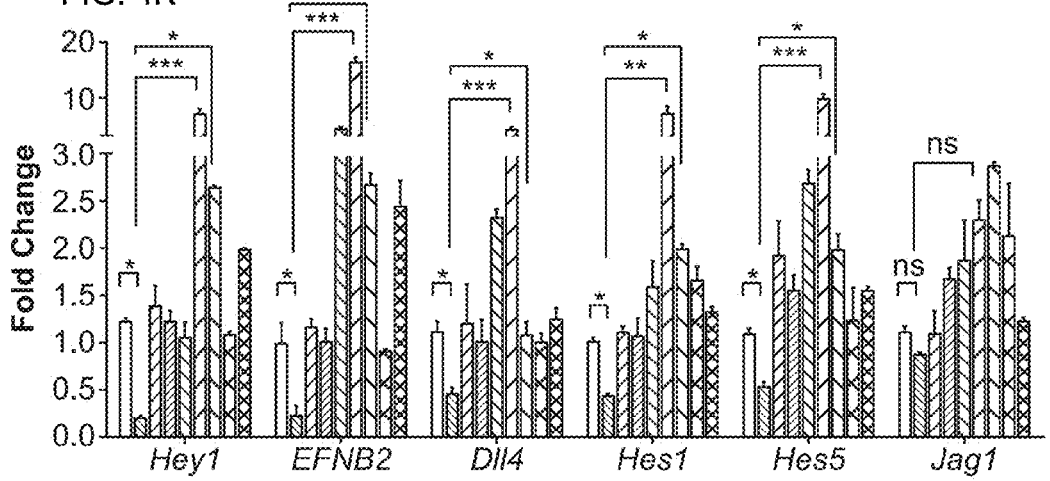
(FIG. 4K) Relative transcriptional levels of Hey1, EFNB2, Dll4, Hes1, Hes5 and Jag1 in HLECs.
Figure 4L:
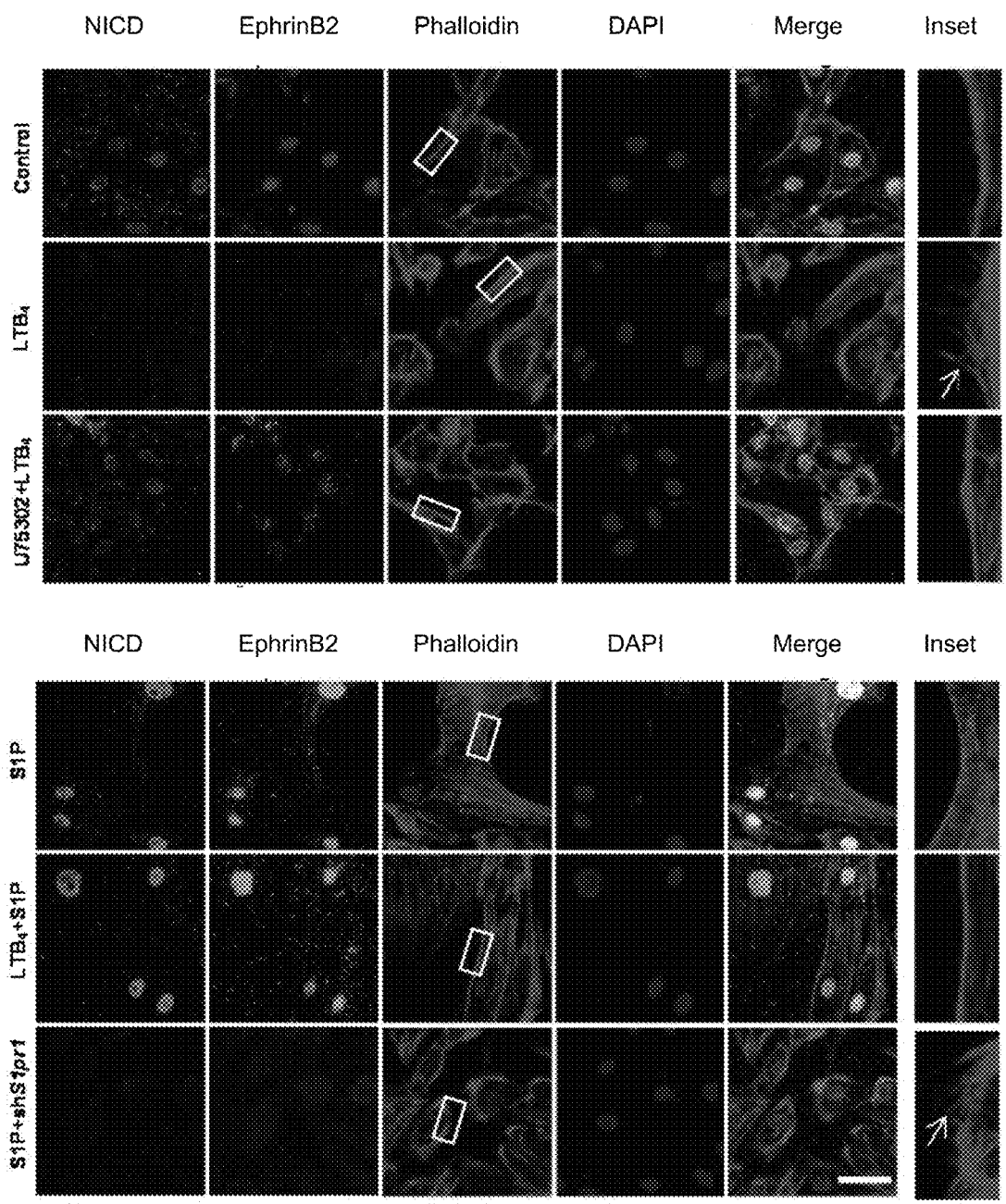
(FIG. 4L) Representative immunofluorescent staining of HLECs, NICD, EphrinB2 and phalloidin. Insets showing the area inside the white box; DAPI stains nuclei; scale bar, 20 µm; white arrows indicate filopodia; n=5.
Figure 4M:
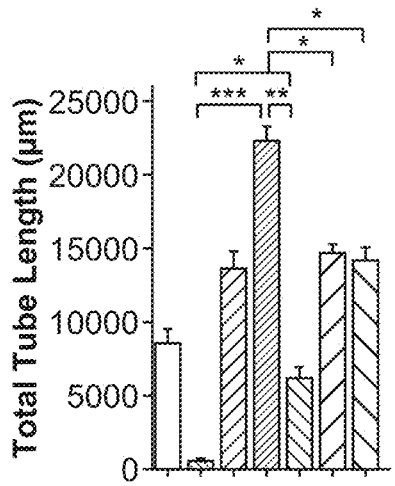
(FIG. 4M-4P) Quantifications of the inhibitory effects of $LTB_4$ on HLEC lymphangiogenesis through attenuation of S1P/Notch signaling measured by tube formation assay (FIG. 4M), trans-well migration assay (-FIG. 4N), wound healing assay (FIG. 4O) and sprouting assay (FIG. 4P).
Figure 4N:
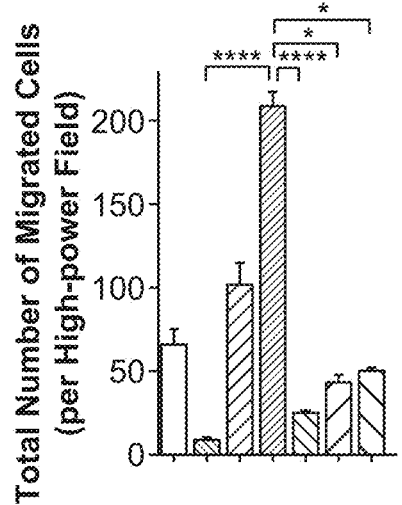
Figure 4O:
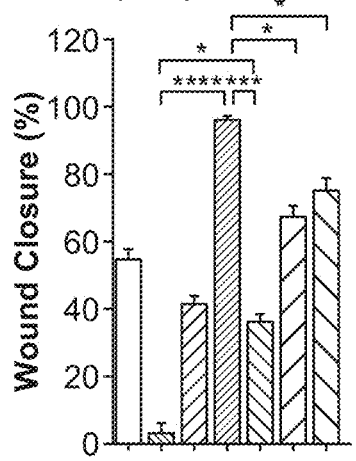
Figure 4P:
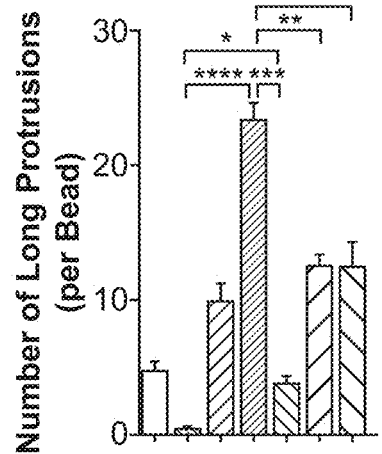

To confirm this relationship, we employed an assay utilizing an engineered CSL reporter. $LTB_4$ inhibited Notch transcriptional activity in a dose dependent fashion, with a >50% reduction of reporter activity with the presence of physiologic (400 nM) levels of $LTB_4$; S1P increased the reporter activity 3-fold from base line, reversed the inhibition from shDll4 and DAPT treatments, and partially overcame the negative effect of $LTB_4$ (indicating that $LTB_4$ inhibits CSL transcription through inhibition of S1P; FIG. 4i,j and Supplemental data not shown). By contrast, shS1pr1 did not reduce reporter activity to the level of the $LTB_4$ group, suggesting an S1P-independent inhibition of Notch signaling by $LTB_4$. PCR measurements of Notch-targeted genes: Hey1, EFNB2, Dll4, Hes1, Hes5 and Jag1 corroborated the reporter assay results (FIG. 4k; Supplemental data not shown). Because Notch signaling is strongly associated with the endothelial stalk-cell phenotype, and NICD nuclear localization is an established approach for determining the activation of Notch, NICD and filopodia histology of HLECs was evaluated. $LTB_4$- and shS1pr1-treated cells revealed increased filopodia and less nuclear-localized NICD and EphrinB2, suggesting a down-regulation of Notch activation (FIG. 4l). By contrast, S1P-treated HLECs displayed a unified stalk-cell shape and enhanced nuclear localization. These in vitro data collectively demonstrate that $LTB_4$ inhibits Notch both directly and indirectly (through a Notch-S1P interaction).

Figure 4Q:
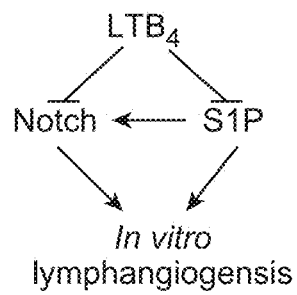

To prove that $LTB_4$ blocks lymphangiogenesis through inhibition of S1P and Notch pathways, we evaluated $LTB_4$-impaired HLEC lymphangiogenesis in the presence of S1P, shS1pr1, shDll4 or DAPT. Addition of shS1pr1 to S1P culture partially inhibited lymphangiogenesis when compared with that of S1P-treated cells; shDll4 or DAPT treatment did not abrogate lymphangiogenesis entirely, indicating that Notch and S1P signaling are independently sufficient to preserve lymphangiogenesis (FIG. 4m-p and Supplemental data not shown). S1P restored the abnormal HLEC migration, differentiation, sprouting, and vessel formation caused by $LTB_4$ and improved HLEC lymphangiogenesis in shDll4 or DAPT-treated cultures; these findings are also consistent with $LTB_4$ attenuation of HLEC lymphangiogenesis through S1P and Notch pathways. Collectively, these in vitro and in vivo data demonstrate that $LTB_4$ directly inhibits the key regulators of lymphangiogenesis (S1P and Notch) while also suggesting a novel role for S1P in promoting Notch signaling in LECs (schematized in FIG. 4q).

Notch and S1P signaling are required for reparative lymphangiogenesis and lymphedema resolution.

Figure 5A:
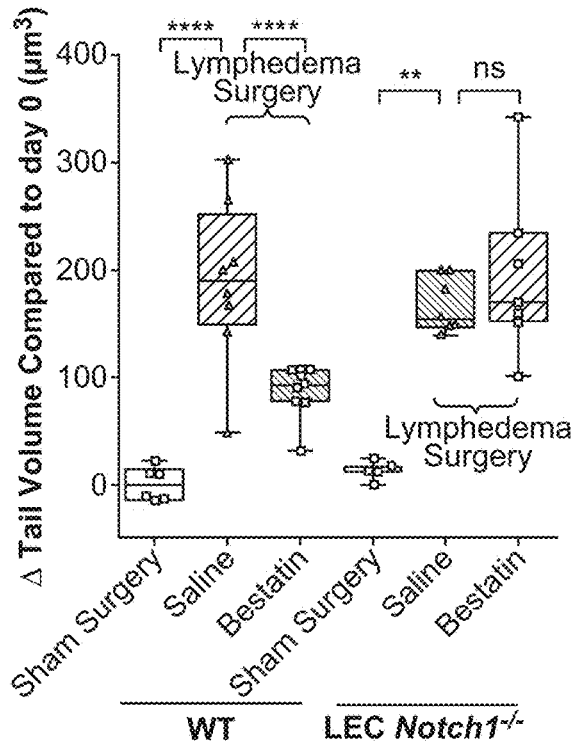
Figure 5B:
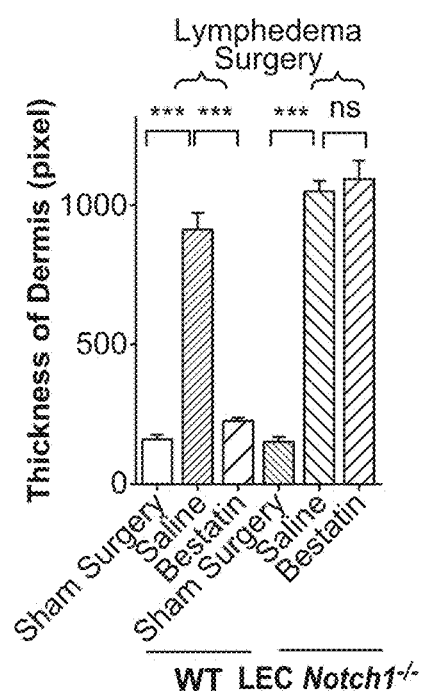
Figure 5C:
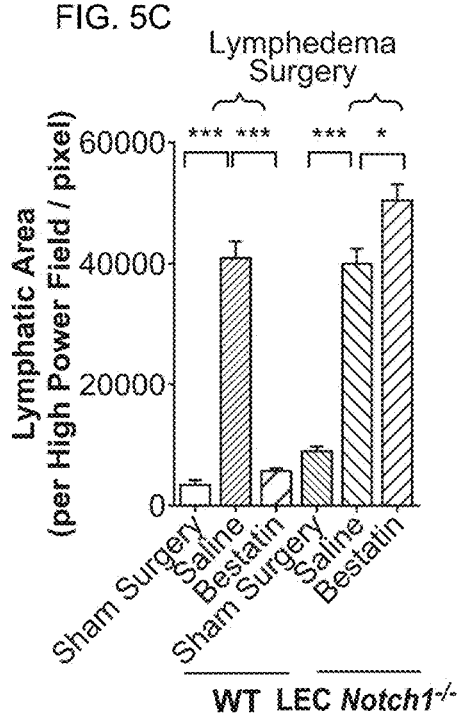

To assess the functional importance of Notch and S1P signaling in lymphatic health, we evaluated NICD nuclear expression in mouse lymphedema, and found that the decreased NICD nuclear accumulation observed in disease was restored by bestatin; a result consistent with an association between Notch signaling and disease resolution (Supplemental data not shown). To specifically attribute diminished lymphatic Notch signaling to $LTB_4$-related lymphedema pathogenesis, we generated Prox1-specific Notch1-deficient mice (LEC Notch1$^{-/-}$) (Supplemental data not shown). LEC Notch1$^{-/-}$ mice demonstrated abnormally dilated lymphatics compared to WT littermates (but without significant changes in tail volume). LEC Notch1$^{-/-}$ mice developed lymphedema refractory to bestatin-therapy; tail pathology being notable for the presence of fewer lymphatic valves (FIG. 5a-c and Supplemental data not shown). Blocking $LTB_4$ production induced tissue Vegfr3, Vegfc and Vegfd transcription in WT group but not in the LEC Notch1−/− lymphedema group (FIG. 5d).

Figure 5F:
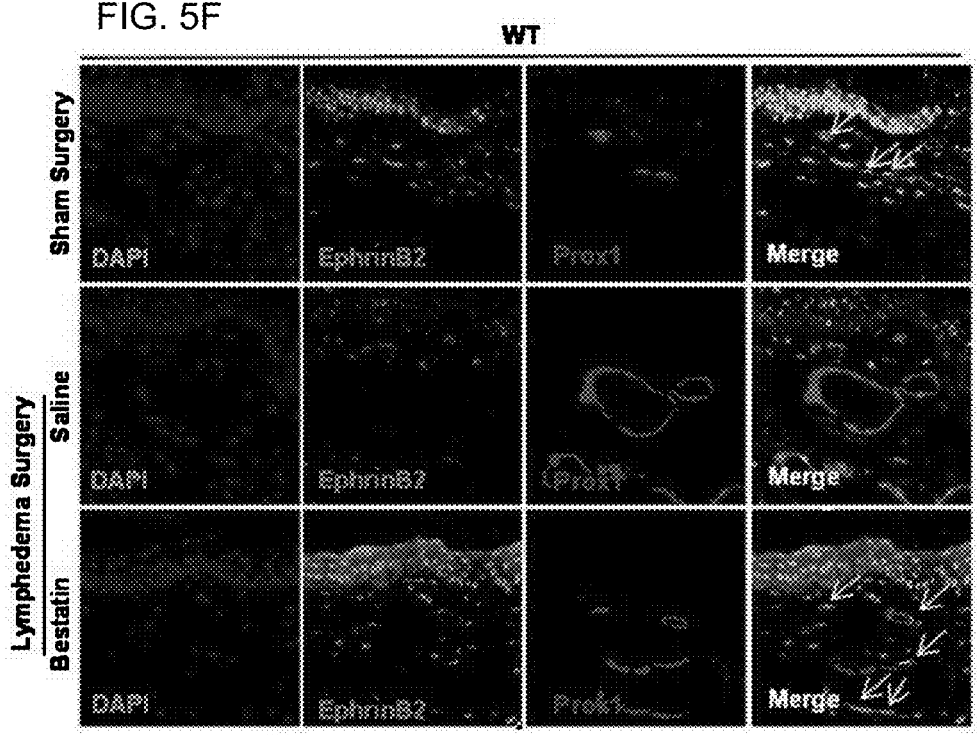
Figure 5G:
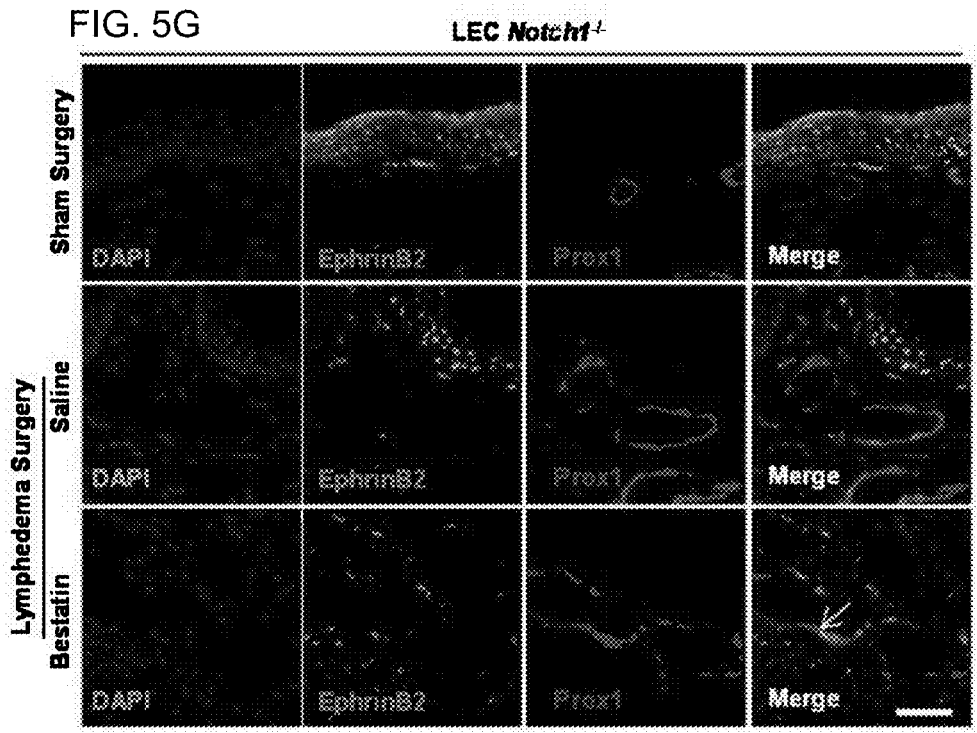

Because reduced expression of Hey1 and EphrinB2 were noted in the diseased lymphatics and were normalized with bestatin therapy, we examined the changes in these two transcriptional factors in the LEC Notch1−/− mice and found that $LTB_4$ antagonism did not restore expression (FIG. 5e-g; Supplemental data not shown). Mural smooth muscle coverage around collecting lymphatics was not restituted by bestatin-therapy in the LEC Notch1−/− mice as it was in WTs (Supplemental data not shown). Addition of DAPT to bestatin-therapy abrogated the therapeutic benefit of bestatin in lymphedema (Supplemental data not shown). Collectively, these in vivo results demonstrate that Notch signaling is required for reversing lymphedema through $LTB_4$ blockade.

Figure 5J:
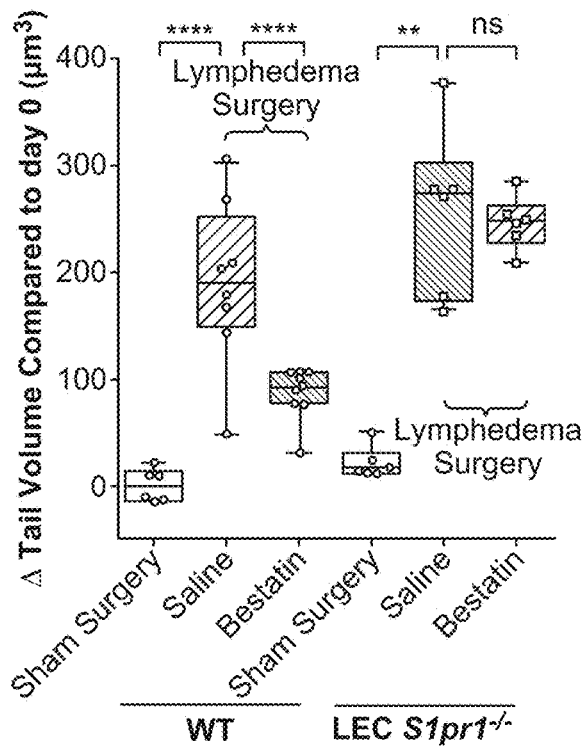
Figure 5J:
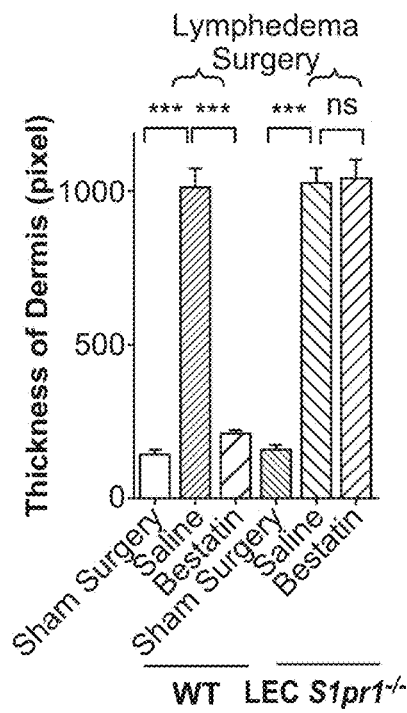
Figure 5J:
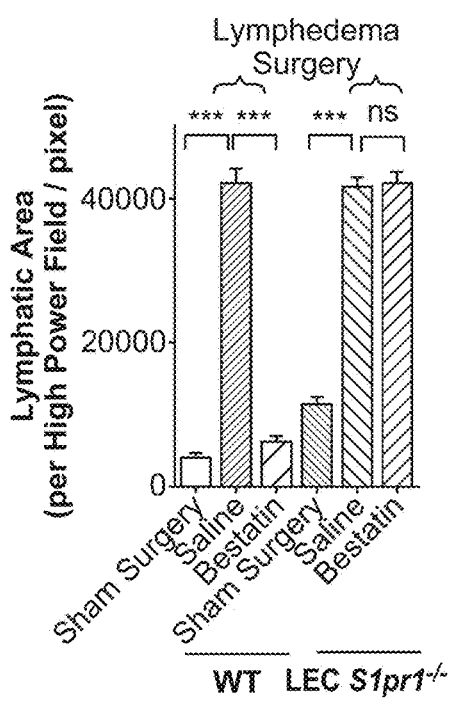

Finally, to verify that lymphatic S1P signaling is required for resolving lymphedema by $LTB_4$ antagonism, we generated Prox1-specific-S1pr1-deficient mice (LEC S1pr1$^{-/-}$) (Supplemental data not shown). Similar to LEC Notch1$^{-/-}$ mice, bestatin treatment failed to reverse lymphedema, as assessed by tail volume, dermal thickness and lymphatic dilation (FIG. 5h-j and Supplemental data not shown); lymphatic Sphk1 and eNOS expression remaining low after bestatin treatment (Supplemental data not shown). In summary, data from the LEC S1pr1$^{-/-}$ mice indicate that lymphatic S1P signaling, like Notch signaling, is important for restoring lymphatic health after injury.

There is currently no approved pharmacotherapy for lymphedema. While inflammation is an established disease, rational pharmacologic targets have been elusive because of the poorly understood underlying pathogenesis. Leukotrienes are important mediators, implicated in a variety of pathologic and protective inflammatory responses. Here, we provide the first evidence for a novel role of $LTB_4$ in experimental and clinical lymphedema. We discovered that $LTB_4$ impaired reparative lymphangiogenesis and sustained the lymphatic insufficiency by disrupting LEC S1P-Notch signaling. Blocking $LTB_4$ signaling after early wound healing effectively reduced tissue inflammation and reversed evidence of disease.

In a seemingly paradoxical series of findings, $Alox5^{-/-}$ and $Ltb4r1^{-/-}$ mice were not protected after tail surgery, with signs of impaired wound healing and enhanced inflammation around the incision site, thus revealing the Janus face of $LTB_4$-mediated effects. $LTB_4$ was a key pathological mediator of experimental lymphedema, but, in addition, early $LTB_4$ signaling was required for proper physiological wound closure. These findings are consistent with a recent study showing that $LTB_4$ has a role in rearranging the collagenous dermal fiber network around wound sites and in forming tight wound seals. Furthermore, $LTB_4$ recruitment of neutrophils is required for proper wound healing in the first 24 hrs. Targeting $LTB_4$ during this early time period blocked normal angiogenic responses and promoted inflammation. If $LTB_4$ antagonism becomes actionable as a treatment to prevent lymphedema after surgical cancer therapy, delaying treatment may be prudent to allow proper wound healing.

S1P is a pro-angiogenic and pro-lymphangiogenic lysophospholipid that serves as an intrinsic vascular stability mediator. Lymphatic Sphk-deficient mice display altered initial lymphatic vessel morphology and junctional VE-cadherin patterning, suggesting that S1P signals are critical to lymphatic development. In our study, $LTB_4$ blocked the expression and activation of Sphk1 in HLECs (main source of S1P pool in the lymph). $LTB_4$ was elevated in the peripheral circulation in both human and murine lymphedema, and may have exerted its inhibitory effects on Sphk systemically.

S1P concentration is normally low in lymphoid tissues and abundant in blood and lymph fluid; an S1P gradient regulates normal lymphocyte egress from lymph nodes. The disruption of this S1P gradient by $LTB_4$ could also affect how lymphocytes exit lymph nodes and thereby contribute to the dysregulated immunity of lymphedema. Because abrogation of S1P signaling did not fully inhibit reparative lymphangiogenesis in vitro, we sought to determine whether a parallel signaling pathway could be implicated; Notch seemed a good candidate, given its established pleiotropic effects in lymphatic development. While Notch signaling is required to suppress lymphatic cellular identity within developing venous structures, embryonic-conditional, LEC specific-Notch1 deletion leads to defective lymphatic vessels, immature lymphoid tissues, and reduced lymphatic valves. Inhibition of Notch pathways during postnatal lymphatic development and wound healing decreases lymphatic density, sprouting, and tip-cell morphology, resulting in reduced cutaneous lymphangiogenesis, compromised mural cell coverage, defective valvular function, and reduced lymphatic regeneration. Collectively, these findings show role for this pathway in postnatal lymphatic repair.

Here, we demonstrated that $LTB_4$ directly inhibited Notch signaling in HLECs. $LTB_4$ down-regulated the protein expression of NICD and DLL4, reduced the CSL reporter activity, diminished Hey1, EFNB2 transcripts, and induced the HLEC tip cell phenotype associated with Notch inhibition in vitro. In lymphedema, decreased Notch signaling, as manifested by low NICD nuclear localization and low Hey1 and EphrinB2 lymphatic expression, was associated with elevated LTB4 production. LEC $Notch1^{-/-}$ mice developed lymphedema that was resistant to the therapeutic effects of $LTB_4$-antagonism, indicating that the Notch pathway is required for the restoration of a normal lymphatic circulation through repair, whereas $LTB_4$ inhibits physiological lymphangiogenesis by interfering with lymphatic Notch signaling. On the basis of our current data, we conclude that Notch signaling, in concert with S1P, is essential for effective repair after lymphatic injury, and that $LTB_4$ antagonism provides a therapy for a disease currently in need of medical therapeutics.

Animal Model

Mice. All animal procedures were approved by Stanford Administrative Panel on Laboratory Animal Care (APLAC). Mice, including wild-type (WT)(C57BL/6J,000664), Notch1loxp/loxp (Notch1tm2Rko/GridJ, 006951), S1pr1$^{loxp/loxp}$ (B6.129S6(FVB)-S1pr1tm2.1Rlp/J, 019141), Alox5-/-(B6; 129S2-Alox5tm1Fun/J, 002263), $LTB_4r1$-/- (B6.129S4-Ltb4r1tm1Adl/J, 008102), tdTomato reporter mice (B6.Cg Gt(ROSA)26Sortm14(CAG-tdTomato)Hze/J, 007914) were purchased from The Jackson Laboratory. The Prox1-Cre-ER mouse (Prox1tm3(cre/ERT2)Gco/J, available from The Jackson Laboratory, 022075) was a gift from Dr. Guillermo C Oliver.

To generate lymphatic endothelial specific tdTomato reporter mice (Prox1-Cre-ER-tdTomato), Prox1-Cre-ER mice were crossed with tdTomato mice. To create lymphatic endothelial cell specific Notch1 or S1pr1 conditional knockouts, Prox1-Cre-ER mice were crossed with Notch1loxp/loxp or S1pr1loxp/loxp mice. Mice with Prox1-Cre-ER and both target alleles floxed by Prox1-Cre-ER/Notch1$^{loxp/loxp}$ or Prox1-Cre-ER/S1pr1$^{loxp/loxp}$ were considered to be either lymphatic endothelial cell-specific Notch1 knockout (LEC Notch1-/-) or S1pr1 knockout (LEC S1pr1$^{-/-}$), respectively. Mice expressing Prox1-Cre-ER were used as WT controls. Tamoxifen at a dose of 5 mg per day was given to the transgenic mice (6 weeks old) for 3 consecutive days to induce Cre recombinase expression. These mice then were subjected to the surgical intervention two weeks after tamoxifen injection. Cre-mediated gene knockout efficiency was evaluated by enumerating Notch1- or S1PR1-expressing lymphatic endothelial cells or by qRT-PCR measurements of Notch1 or S1pr1 transcripts in the lymphatic endothelial cells, sorted by flow cytometry.

Surgical induction of experimental lymphatic vascular insufficiency. Acquired lymphedema was surgically induced in the tails of female C57BL/6J mice through the thermal ablation of lymphatic trunks, using a protocol that has been previously developed and optimized. Briefly, a full-thickness circumferential incision of the skin was made 16 mm distal to the base of the mouse tail under anesthesia. Lymphatic trunks were ablated through controlled, limited cautery application under the surgical microscope. For surgical controls (sham animals), the skin incision alone was performed without lymphatic cautery. Normal controls did not undergo any surgical manipulation.

All small molecule drugs were administered through daily intraperitoneal injection. The dosing regimen for each individual drug was as follows: ketoprofen, 5 mg/kg; zileuton, 60 mg/kg; ibuprofen, 5 mg/kg; bestatin, 4 mg/kg; Ly293111, 1 mg/kg; montelukast, 20 mg/kg and DAPT, 30 mg/kg.

Tail volume quantitation. Tail-volume measurements at each designated time were quantified by observers blinded to the treatment status of the subjects. Tail volumes were calculated through a digital photographic technique pre-operatively, and post-operatively (d3, d9, d14, d20, and d24), using an Olympus D520 Zoom digital camera at SHQ resolution at a fixed distance from the subject (37 cm), as previously described. Tail volumes were derived from the measurement of the tail diameter using the truncated cone approximation. Microlymphangiography was performed by injecting FITC-dextran (size: 2000 kDa) subcutaneously into mouse tails on post-surgery d24. Images were taken 20 minutes after injection.

Quantification of LTB4, PGE2 and S1P with LC-MS/MS. Briefly, LTB4, PGE2 and S1P were separated from serum with an ACE reverse phase C18 HPLC column. Formic acid 0.5% in 5 mM NH4Ac (A) and formic acid 0.5% in acetonitrile/water (9/1) (B) were used as the mobile phase. Lipids were detected with positive multiple reaction monitor (MRM) scanning at 335.16/194.80 m/z for LTB4, 351.20/189.50 m/z for PGE2 and 330.20/264.40 m/z for S1P using a Sciex API-4000 MS/MS combined with a Shimazu 20A HPLC system. The internal standard of this method was Carbutamide. The quantification limit was 1 ng/ml. The calibration range was 1-2000 ng/ml. The accuracy of the standards and control samples ranged from 88.7% to 120%.

Lentivirus-based RNAi. Lentiviral transduction particles expressing specific shRNA sequence in MISSION® pLKO.1-CMV-tGFP vector were purchased from Sigma-Aldrich. Two clones (NM_181657.3-2522s21c1 and NM_181657.3-2961s21c1) were tested for efficiency in silencing Ltb4r1. NM_019074.2-2149s21c1 and NM_019074.2-2276s21c1 were used to silence Dll4. Silencing S1pr1 was tested using NM_007901.4-1631s21c1 and NM_007901.4-576s21c1. MISSION@ pLKO.1-CMV-tGFP non-target shRNA control transduction particles containing shRNA sequence targeting tGFP were used as control viral particles in all experiments. Gene expression after knockdown was quantified by qRT-PCR.

For the in vivo shLtb4r1 lentivirus transduction experiment, approximately $5 \times 10^6$ TU/ml lentivirus was injected into the mouse tail 2 cm distal to the surgical site 7d before surgery (in the pre-treatment group) or 3d after the surgery (in the treatment group). Viral particles were mixed with Lipofectamine 2,000 (5% final vol/vol, Invitrogen) before injection, to increase transduction efficiency. qRT-PCR, immunofluorescence and fluorescence in situ hybridization were used to evaluate the silencing efficiency in the mouse tail skin 24d after surgery.

Fluorescence in situ hybridization. Fluorescence in situ hybridization (FISH) was used to monitor the silencing efficiency of local lentiviral shLtb4r1 administration. In brief, single-colored FISH testing was performed on 5-gm frozen sections of tail-tissue collected on d24 after surgery using DIG-tagged RNA probes against Ltb4r1 (Exiqon). The probes were diluted with hybridization solution (H7782, Sigma-Aldrich) and incubated with tissue samples (after antigen retrieval) overnight at 37° C. On the following morning, stringency wash was performed by washing the slides with pre-warmed 45° C. 1×SSC solution three times (S6639, Sigma-Aldrich) and at room temperature 2×SSC one time. The slides were then stained using a DIG immunofluorescence staining protocol. Fluorescent images were acquired by Zeiss 710 confocal microscopy and analyzed with ImageJ software.

Tube formation assay. Matrigel (BD Matrigel Basement Membrane Matrix Growth Factor Reduced, Phenol Red Free) was thawed on ice overnight, dispersed into 48-well plates (100 µl per well) and allowed to polymerize for 30 minutes at 37° C. Serum starved HLECs were seeded on the Matrigel at a density of $1 \times 10^4$ cells per well. Images of four representative fields were taken 10 hrs later. ImageJ software was used to determine total cellular cord length.

Migration assay. Cellular migration was evaluated using a modified Boyden chamber assay. Briefly, $2 \times 10^4$ serum-starved HLECs in 250 µl serum free medium were seeded in the upper chamber of the trans-well. 750 µl of serum free ECM containing various drugs was placed in the lower chamber. Ten hours later, migrated cells were stained with a modified Giemsa solution (Sigma-Aldrich) for quantification.

Wound healing assay. $6 \times 10^5$ HLECs were seeded on an Easy Slide (Millipore) the day before the experiment and allowed to form a fully confluent monolayer, and then cells were serum starved for 12 hrs. A 200 µl pipet tip was used to scratch a straight line across the middle of the cell monolayer. Cell debris was removed through PBS washing. Images were taken immediately after the scratch and the same windows were imaged again 12 hrs later. The rate of cell migration was calculated as the average percent wound closure from at least 5 independent experiments using ImageJ software.

Fibrin gel sprouting assay. HLECs were first coated overnight onto the Cytodex-3 beads with an approximate concentration of 400 cells per bead. On the following day, the microbeads were transferred to 2.0 mg/ml fibrinogen solution containing 0.15 units/ml of aprotinin. Later, 0.625 units/ml thrombin was added to the mixture to gelatinize the fibrin gel. Endothelial sprouts (vessel outgrowth) were observed within 3 days of culture using phase micrographic images and quantified as number of vessels per bead.

Matrigel plug assay. SCID mice (NOD.Cg-Prkdcscid I/2rgtm1Wjl/SzJ, The Jackson Laboratory) of 4-6 weeks of age were used for Matrigel plug injection. Two 250 µl Matrigel plugs were subcutaneously injected into the dorsal surface of the mice. Plugs were recovered with the adjacent subcutaneous tissue 14d later. Tissue was then embedded in paraffin and sectioned for staining.

pG13-6-CSL luciferase assay. CSL reporter activity was determined as described previously. HLECs ($5.0 \times 10^5$) were electrophoresed and transfected with both 1 µg CSL luciferase reporter (pG13-11-CSL) and 10 ng Renilla luciferase pRL-SV40 (Promega) using Nucleofactor (Lonza). Luciferase and Renilla activity were then determined with Dual-Luciferase® Reporter Assay System (Promega) and Berthold dual-injection illuminometer.

Western Blot HLECs were lysed with RIPA buffer containing protease and phosphatase inhibitors. Lysates were sonicated briefly and centrifuged. The supernatant was collected and protein concentration was determined by BCA assay. 60 pg of protein were resolved on a 10% SDS-PAGE gel, transferred to a nitrocellulose membrane, blocked with 5% milk and probed with one of the following antibodies: anti-Sphk1 (3297,Cell Signaling); antip-Sphk1(SP1641, ECM Biosciences); anti-NICD (ab8925,Abcam), anti-VEGFR3 (AF743,R&D); anti-DLL4 (ab7280, Abcam). Actin was used to normalize the total protein. Immunofluorescence Immunofluorescence staining was performed using the following primary antibodies: anti-5-LO (3289, Cell Signaling); anti-MPO (ab45977, Abcam); Anti-CD68 (ab22506, Abcam); anti-Prox1(ab101851, Abcam); anti-NICD (ab8925, Abcam), anti-EphrinB2 (AF496,R&D); anti-VEGFR3 (AF743,R&D); anti-Hey1(ab22614, Abcam); Alexa-Fluor-555 Phalloidin (8953,Cell Signaling); anti-DIG (11093274910, Sigma-Aldrich). Negative controls with isotype IgG were run in parallel. Images were acquired by Zeiss 710 confocal microscopy and analyzed using ImageJ software.

Quantitative RT-PCR. Quantitative PCR (qRT-PCR) was performed using FastStart SYBR Green (Roche) on a Lightcycler 480. mRNA expression relative to GAPDH mRNA levels were calculated using the delta-delta threshold cycle (ΔΔCT) method. PCR microarrays were purchased from Qiagen: RT2 Profiler PCR Array 384-Well Format, Mouse Angiogenesis PAMM-024ZA) and VEGF Signaling (330231 PAMM-091ZA). Primers used for qRT-PCR are: Ltb4r1: (SEQ ID NO:1) GGCTTCGTGGTCAAGCTACT; (SEQ ID NO:2) GGTACAGAAGTGGGTCAGGC; Ltb4r2: (SEQ ID NO:3) GGTCAATCTCCTACAGGCGG; (SEQ ID NO:4) TGTCTTTCTCCGTCTTGCCC; S1 pr1: (SEQ ID NO:5) GCGCTCAGAGACTTCGTCTT; (SEQ ID NO:6) GCCTGGGGTGGTATTTCTCC; Dll4: (SEQ ID NO:7) GCAAGCAGGTTTCAGTAGCG; (SEQ ID NO:8) CGC-CTTCTCAAAAACTCCGC; Jag1: (SEQ ID NO:9) CCTTTGCAGCTCAGAACCAC; (SEQ ID NO:10) TCCCAGGGGAAAAAGCCTATC; Hey1: (SEQ ID NO:11) CGTGAGTGGGATCAGTGTGC; (SEQ ID NO:12) CTCGATGATGCCTCTCCGTC; EFNB2: (SEQ ID NO:13) CAGGTCCTCGTGGAGCATC; (SEQ ID NO:14) AGCAGTTCTTGCTCAGGACG; Hes1: (SEQ ID NO:15) CTGGTGCTGATAACAGCGGA; (SEQ ID NO:16) GTTT-GTCCGGTGTCGTGTTG; Hes5: (SEQ ID NO:17) ACCT-GAAACACAGCAAAGCC; (SEQ ID NO:18) CCACATC-CAGAGGAACGAGC; Tie2: (SEQ ID NO:19) GGCTCAGGCATTCCAGAACAG; (SEQ ID NO:20) CTGTTGGGAGGACAGTGTGG; ANGPT1: (SEQ ID NO:21) CTCAGACTGCAGAGCAGACC; (SEQ ID NO:22) TCCTCCCTTTAGCAAAACACC; Vefgr3: (SEQ ID NO:23) TCCATATCCTGCAGGGGACA; (SEQ ID NO:24) CCGGGCCTTGATGTACTTGT; Vegfc: (SEQ ID NO:25) CTTGTCTCTGGCGTGTTCCC; (SEQ ID NO:26) CCCCACATCTGTAGACGGA; Vegfd: (SEQ ID NO:27) AAGATTGTGTGTGAGGCAGTGA; (SEQ ID NO:28) GCTGAGCGTGAGTCCATACT; Lyve1: (SEQ ID NO:29) CACTAGGCACCCAGTCCAAG; (SEQ ID NO:30) GTT-GCGGGTGTTTGAGTGTC.

Statistical methods. GraphPad Prism® version 5.0c was used for statistical analysis. Differences between two groups at a single time point were compared using the Mann-Whitney test. For comparisons between multiple experimental groups at a single time point, the Kruskall-Wallis test followed by the Dunn's multiple comparisons test for post hoc analyses were used. Pearson correlation test was used to calculate linear regression. All analyses were considered statistically significant at $P<0.05$.

Example 2

Studies of Efficacy in Treatment of Lymphedema with Ubenimex

A study is conducted for treatment of patients with acquired lymphedema of the lower extremities with ubenimex. In this study, ubenimex is evaluated over a 6-month treatment period to determine the effect on dermal thickness and other efficacy measures in patients with secondary leg lymphedema. The efficacy, safety and tolerability of ubenimex in this patient population is characterized.

Adult male and female subjects are enrolled with a confirmed diagnosis of Stage II or greater secondary leg lymphedema, based on a positive lymphoscintigraphy (LSG) study of the affected leg. At least 20 individuals are enrolled in each of the treatment and placebo arm of the trial.

Individuals are given oral 150 mg ubenimex three times daily for a total daily dose of 450 mg. The drug and placebo are provided in a capsule form.

Efficacy assessments include skin thickness (as measured by skinfold calipers), leg volume (as measured by standardized tape measure), bioimpedance (as measured by the SFB7 (ImpediMed) to measure 4-limb bioimpedance to determine extracellular fluid volume), and skin biopsy results (as measured by 6-mm skin punch biopsy samples to assess skin thickness and architecture (e.g., presence of hyperkeratosis, dermal collagen, and adipose deposition).

Additional efficacy measurements include a leg lymphedema quality-of-life (LYMQoL) questionnaire designed to assess the effects of leg lymphedema on quality of life with respect to symptoms, body image/appearance, function, and mood; measurement of blood concentrations of ubenimex to characterize the steady-state PK of ubenimex pre-dose and at 0.5, 1.5, 2.5, 3.5, 6, and 8 hours after morning dosing; and measurement of blood concentrations of the metabolite (2S, 3R)-3-amino-2-hydroxy-4-phenylbutyric acid [abbreviated as (2S,3R)-AHPA]; and measurement of plasma $LTB_4$ levels using the ex vivo $LTB_4$ stimulation assay (Lin et al., 2013) predose and at 0.5, 1.5, 2.5, 3.5, 6, and 8 hours after morning dosing to gauge the degree of peripheral inhibition of $LTA_4H$ (PD measure).

It is expected that the trial will show a statistically significant difference between the ubenimex and placebo treatment arms using the protocol described herein as evidenced by clinical indicia described above. A significant difference in dermal thickness of the leg may be up to about 2 mm, up to about 5 mm, up to about 7.5 mm, up to about 10 mm, or more.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

What is claimed:

1. A method for the treatment of lymphedema in a human patient, the method comprising:
   administering to the patient (2S)-2-[[(2S,3R)-3-amino-2-hydroxy-4-phenylbutanoyl]amino]-4-methylpentanoic acid in an amount effective to prevent or reduce lymphedema symptoms restore architecture of lymphedematous tissue in acquired lymphedema.

2. The method of claim 1, wherein dermal thickness of lymphedematous tissue is reduced by at least about 2 mm following treatment.

3. The method of claim 1, wherein the patient has lymphedema at stage 0, 1, 2 or 3.

4. The method of claim 1, wherein the effective amount is about 10-1500 mg/day.

5. The method of claim 1, wherein the effective amount is about 10-500 mg/day.

6. The method of claim 1, wherein (2S)-2-[[(2S,3R)-3-amino-2-hydroxy-4-phenylbutanoyllamino]-4-methylpentanoic acid is administered twice daily.

7. The method of claim 1, wherein (2S)-2-[[(2S,3R)-3-amino-2-hydroxy-4-phenylbutanoyllamino]-4-methylpentanoic acid is administered three times daily.

8. A method for the treatment of lymphedema in a human patient, the method comprising:
   administering to the patient (2S)-2-[[(2S,3R)-3-amino-2-hydroxy-4-phenylbutanoyl]amino]-4-methylpentanoic acid at a dose of about 10-500 mg/day to restore architecture of lymphedematous tissue in acquired lymphedema.

9. The method of claim 1, wherein the method further comprises administering an effective amount of a second therapeutic agent.

10. The method of claim 9, wherein the second therapeutic agent is a diuretic.

11. The method of claim 1, wherein administration of (2S)-2-[[(2S,3R)-3-amino-2-hydroxy-4-phenylbutanoyl]amino]-4-methylpentanoic acid is commenced following surgical wound healing.

12. The method of claim 8, wherein administration of (2S)-2-[[(2S,3R)-3-amino-2-hydroxy-4-phenylbutanoyl]amino]-4-methylpentanoic acid is commenced following surgical wound healing.

* * * * *

SEQUENCE LISTING

<160> NUMBER OF SEQ ID NOS: 30

<210> SEQ ID NO 1
<211> LENGTH: 20
<212> TYPE: DNA

```
<213> ORGANISM: Artificial Sequence
<220> FEATURE:
<223> OTHER INFORMATION: Synthetic Primer

<400> SEQUENCE: 1
ggcttcgtgg tcaagctact                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
ggtacagaag tgggtcaggc                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
ggtcaatctc ctacaggcgg                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
tgtctttctc cgtcttgccc                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
gcgctcagag acttcgtctt                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gcctggggtg gtatttctcc                                                  20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
gcaagcaggt ttcagtagcg                                                  20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
cgccttctca aaaactccgc                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
cctttgcagc tcagaaccac                                                    20

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
tcccagggga aaaagcctat c                                                  21

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
cgtgagtggg atcagtgtgc                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
ctcgatgatg cctctccgtc                                                    20

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
caggtcctcg tggagcatc                                                     19

<210> SEQ ID NO 14
<211> LENGTH: 20
<212> TYPE: DNA
<213> ORGANISM: Artificial Sequence
<220> FEATURE:

```
<223> OTHER INFORMATION: Synthetic Primer

<400> SEQUENCE: 14
agcagttctt gctcaggacg                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
ctggtgctga taacagcgga                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
gtttgtccgg tgtcgtgttg                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
acctgaaaca cagcaaagcc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
ccacatccag aggaacgagc                                              20

<210> SEQ ID NO 19
<211> LENGTH: 21
<212> TYPE: DNA
<213> ORGANISM: Artificial Sequence
<220> FEATURE:
<223> OTHER INFORMATION: Synthetic Primer

<400> SEQUENCE: 19
ggctcaggca ttccagaaca g                                            21

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
ctgttgggag gacagtgtgg                                              20
```

```
<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
ctcagactgc agagcagacc                                                    20

<210> SEQ ID NO 22
<211> LENGTH: 21
<212> TYPE: DNA
<213> ORGANISM: Artificial Sequence
<220> FEATURE:
<223> OTHER INFORMATION: Synthetic Primer

<400> SEQUENCE: 22
tcctcccttt agcaaaacac c                                                  21

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
tccatatcct gcaggggaca                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
ccgggccttg atgtacttgt                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
cttgtctctg gcgtgttccc                                                    20

<210> SEQ ID NO 26
<211> LENGTH: 19
<212> TYPE: DNA
<213> ORGANISM: Artificial Sequence
<220> FEATURE:
<223> OTHER INFORMATION: Synthetic Primer

<400> SEQUENCE: 26
ccccacatct gtagacgga                                                     19

<210> SEQ ID NO 27
<211> LENGTH: 22
<212> TYPE: DNA
<213> ORGANISM: Artificial Sequence
<220> FEATURE:
<223> OTHER INFORMATION: Synthetic Primer
```

```
<400> SEQUENCE: 27
aagattgtgt gtgaggcagt ga                                              22

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer

<400> SEQUENCE: 28
gctgagcgtg agtccatact                                                 20

<210> SEQ ID NO 29
<211> LENGTH: 20
<212> TYPE: DNA
<213> ORGANISM: Artificial Sequence
<220> FEATURE:
<223> OTHER INFORMATION: Synthetic Primer

<400> SEQUENCE: 29
cactaggcac ccagtccaag                                                 20

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer

<400> SEQUENCE: 30
gttgcgggtg tttgagtgtc                                                 20
```